US007282489B2

(12) United States Patent
Levy et al.

(10) Patent No.: US 7,282,489 B2
(45) Date of Patent: Oct. 16, 2007

(54) COMPOSITIONS AND METHODS FOR PERFORMING REVERSE GENE THERAPY

(75) Inventors: Robert J. Levy, Merion Station, PA (US); Denise Y. Burton, Bensalem, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 377 days.

(21) Appl. No.: 10/422,551

(22) Filed: Jul. 31, 2003

(65) Prior Publication Data
US 2004/0087528 A1 May 6, 2004

Related U.S. Application Data

(63) Continuation-in-part of application No. 09/487,851, filed on Jan. 19, 2000, now Pat. No. 6,852,704.

(51) Int. Cl.
A61K 48/00 (2006.01)
(52) U.S. Cl. ...................... 514/44; 435/320.1; 435/455
(58) Field of Classification Search .................... None
See application file for complete search history.

(56) References Cited

U.S. PATENT DOCUMENTS

| 4,160,452 A | 7/1979 | Theeuwes |
| 4,256,108 A | 3/1981 | Theeuwes |
| 4,265,874 A | 5/1981 | Bonsen |
| 5,034,506 A | 7/1991 | Summerton |
| 6,207,383 B1 | 3/2001 | Keating |
| 6,852,704 B1 * | 2/2005 | Levy et al. .................... 514/44 |

OTHER PUBLICATIONS

Staba et al, Gene Ther 1998;5:293-300.*
Arai et al, PNAS 1997;94:13862-7.*
Liu et al, J Biol Chem 2001;276:34379-87.*
Orkin et al. NIH Report, Dec. 1995.*
Weerapura et al, J Physiol 2002:540:15-27.*
Anderson, Hum Gene Ther 2002;13:1261-2.*
Boucher et al, J Clin Invest Feb. 1999; 103:441-5.*
Peterson, Statement of Amy Patterson M.D., Feb. 2000.*
Boucher, et al., J. Clin. Invest., 103:441-445, (1999).
Okuyama, T., et al., Gene Ther., 8:1047-53, (1998).
Vinyals, et al., Gene Ther., 6:22-33, (1999).
Kagan, et al., "The dominant negative LQT2 mutation A561V reduces wild-type HERG expression," J. of Biol. Chem., 275:11241-8, (2000).
Eck, et al., "Gene-based Therapy," Goodman & Gilman's The Pharmacological Basis of Therapeutics-Ninth Edition, McGraw-Hill:77-101 (1996).
Anderson et al., 1995, J. Biomed. Mater. Res. 29:1473-1475.
Anderson et al., 1995, Tissue Eng. 1:323-326.
Antman, 1996, Am. J. Cardiol. 78:67-72.
Arenal et al., 1999, Circulation 99:2771-2778.
Bello et al., 1985, J. Biomol. Struct. Dyn. 2:899-913.
Biben et al., 1996, Develop. Biol. 173:200-212.
Brauner et al., 1997, J. Thorac Cardiovasc Surg 114:923-933.
Buchanan et al., 1993, J. Cardiovasc. Pharmacol. 33:10-14.
Chen et al., 1995, Human Gene Therapy 6:917-926.
Chiquet et al., 1996, Biochem. Cell Biol. 74:737-744.
Chubet et al., 1996, Biotechniques 20:136-141.
Cochrane et al., 1996, Drug Ther. Bull. 34:41-45.
Copertino et al., 1997, Proc. Natl. Acad. Sci. USA 94:1846-1851.
Cosio et al., 1996, Pacing Clin. Electrophysiol. 19:965-975.
Cosio et al., 1993, Lancet 341:1189-1193.
Cosio et al., 1996, Arch. Mal. Coeur Vaiss. 1:75-81.
Couffinhal et al., 1997, Hum. Gene Ther. 8: 929-934.
Cox et al., 1993, Ann. Thorac. Surg. 56:814-823.
Cox et al., 1995, J. Thorac. Cardiovasc. Surg. 110:485-495.
Desai et al., 1996, Pharm. Res. 13:1838-1845.
Desai et al., 1997, Pharm. Res. 14:1568-1573.
Fei et al., 1997, Circ. Res. 80:242-252.
Field, Science 239:1029-1033.
Frame, 1996, Cardiol. Clin. 14:471-481.
Franz et al., 1997, Cardiovascular Research 35:560-566.
Froissart et al., 1998, Clin. Gen. 53:362-368.
Gibson et al., 1995, In: Molecular Interventions and Local Drug Delivery in Cardiovascular Disease, Edelman, Ed., W.B. Saunders Co., Ltd., London, UK, pp. 327-352.
Gottsauner-Wolf et al., 1997, Am. Heart J. 133:329-334.
Guzman et al., 1996, Circulation 94:1441-1448.
Hammond et al., 1997, Analyt. Chem. 69:1192-1196.
Huang et al., 1995, Nature 378:292-295.
Humphrey et al., 1997, Adv. Drug Delivery Rev. 24: 87-108.
Hunter et al., 1995, J. Biol. Chem. 270:173-178.
Jain et al., 1991, Anal. Biochem. 199:119-124.
Kaab et al., 1998, Circulation 98:1383-1393.
Kaplan et al., 1998, Biochem. Pharmacol. 55:373-382.
Kim et al., 1998, J. Clin. Invest. 101:1821-1826.
King et al., 1997, J. Biol. Chem. 272:28518-28522.
Labhasetwar et al., 1994, J. Cardiovasc. Pharm. 24:826-840.
Labhasetwar et al., 1995, Clin. Pharmacokinet. 29:1-5.
Labhasetwar et al., 1995, Proc. Natl. Acad. Sci. USA 92:2612-2616.
Labhasetwar et al., 1997, Adv. Drug Del. Rev. 24:109-120.
Labhasetwar et al., 1997, Adv. Drug. Del. Rev. 24:63-85.
Labhasetwar et al., 1998, J. Cardiovasc. Pharmacol. 31:449-455.
Lasic (1997), In: Gene Delivery, Lipsows, Ed., CRC Press, Boca Raton, Florida, pp. 33-37 and 56-61.
Levy et al., 1995, J. Controlled Release 36:137-147.
Levy et al., 1996, Drug Delivery 3:137-142.
Martin et al., 1995, Nature 375:691-694.
Martinez-Fong et al., 1994, Hepatology 20:1602-1608.

(Continued)

Primary Examiner—Q. Janice Li
(74) Attorney, Agent, or Firm—Dann, Dorfman, Herrell & Skillman, P.C.; Robert C. Netter; Kathleen D. Rigaut

(57) ABSTRACT

The invention relates to compositions and methods for reverse gene therapy, wherein a gene therapy vector encoding a gene product (e.g. a protein) which is usually only expressed in cells of an abnormal tissue is delivered to a cell of an animal afflicted with a disease or disorder to alleviate the disease or disorder. In one embodiment, a plasmid vector encoding HERG (A561V) protein is delivered to a cell of an animal afflicted with re-entrant atrial flutter-mediated cardiac arrhythmia.

9 Claims, 18 Drawing Sheets

OTHER PUBLICATIONS

Mason et al., 1998, Gene Therapy 5:1098-1104.
McDonald et al., 1997, Nature 388:289-292.
Milano et al., 1994, Proc. Natl. Acad. Sci. USA 91: 10109-10113.
Miyamoto et al., 1998, J. Cell. Physiol. 177:58-67.
Nakao et al., 1998, Am. J. Pathol. 152:1237-1245.
Natale et al., 1996, Am. J. Cardiol. 78:1431-1433.
Nielsen et al., 1991, Science 254: 1497.
Nishina et al., 1997, Nature 385:350-353.
Priori et al., 1997, PACE 29:2052-2057.
Radler et al., 1997, Science 275:810-814.
Ranger et al., 1998, Nature 392:186-190.
Rauch et al., 1998, Am. J. Med. Gen. 78:322-331.
Robbins, 1997, Trends Cardiovasc. Med. 7:185-191.
Robbins and Ghivizzani, 1998, Pharmacol. Ther. 80:35-47.
Roden et al., 1996, Annu. Rev. Med. 47:135-48.
Rodefeld et al., 1996, J. Thorac. Cardiovasc. Surg. 112:898-907.
Sanguinetti et al., 1995, Cell 81:299-307.
Sanguinetti et al., 1996, Nature 384:80-83.
Sanguinetti et al., 1996, Proc. Natl. Acad. Sci. USA. 93:2208-2212.
Schneider et al., 1998, FEBS Letters 429:269-273.
Schwendeman et al., 1995, Pharm. Res. 12:790-795.
Shelness et al., 1994, J. Biol. Chem. 269:9310-9318.
Sintov et al., 1997, Int. J. Pharm. 146:55-62.
Solway et al., 1995, J. Biol. Chem. 270:13460-13469.
Song et al., 1997, J. Controlled Release 45:177-192.
Subramanian et al., 1995, Cell Growth Differ. 6: 131-137.
Villa et al., 1995, Circ. Res. 76:505-513.
Waldo, 1994, Clin. Cardiol. 17:1121-1126, 1994.
Wang et al., 1997, Current Op. Cardio. 12:310-320.
Wells et al., 1979, Circulation 60:665-673.
Wolfert et al., 1996, Gene Therapy 3:269-273.
Wolfert et al., 1996, Human Gene Therapy 7:2123-33.
Wood et al., 1995, In: Molecular Interventions and Local Drug Delivery in Cardiovascular Disease, Edelman, Ed., W.B. Saunders Co., LTD, London, UK, pp. 399-471.
Zhou et al., 1999, J. of Biol. Chem. 274:31123-31126.
Bradley et al, J Clin Invest Mar. 1999; 102;889-96.
Mazhari, Cir Res 2002:90:842-3.
Alton et al. "Cationic lipid-mediated CFTR gene transfer to the lungs and nose of patients with cystic fibrosis: a double-blind . . . ," pp. 947-654 vol. 353, 1999.

* cited by examiner

Inhibition of Atrial Flutter with
Controlled Release Ibutilide: Epicardial Wire Results

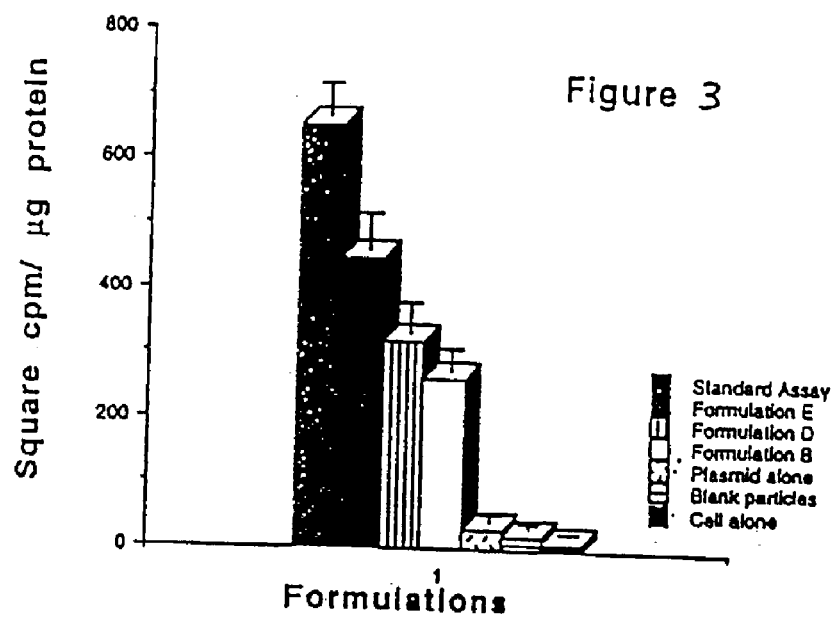
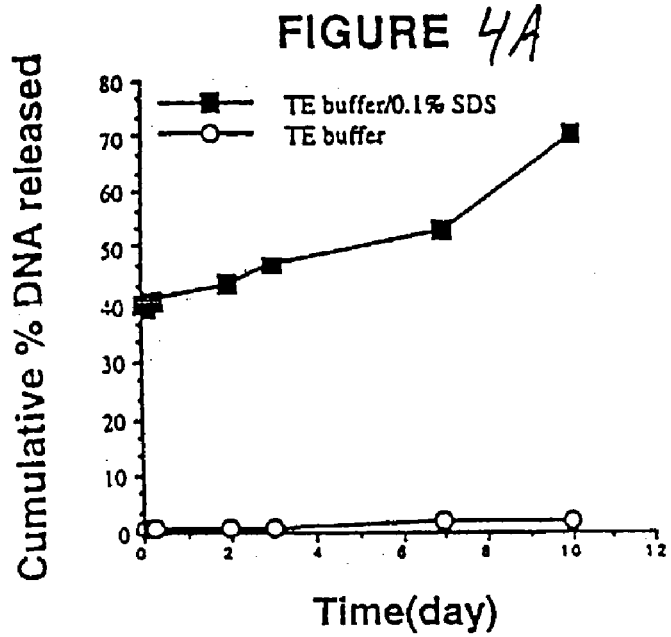

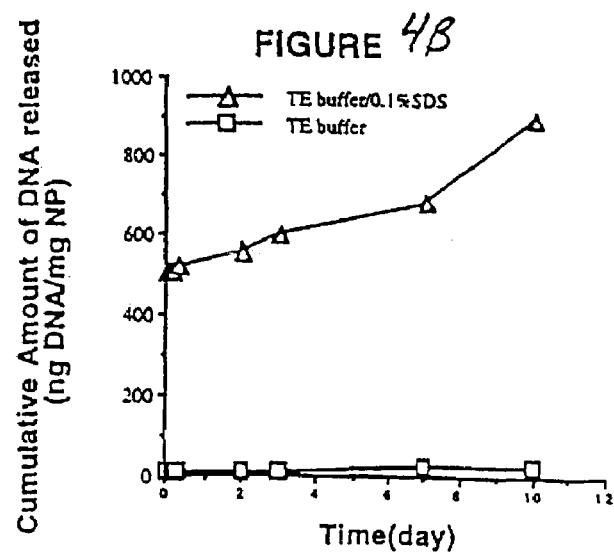
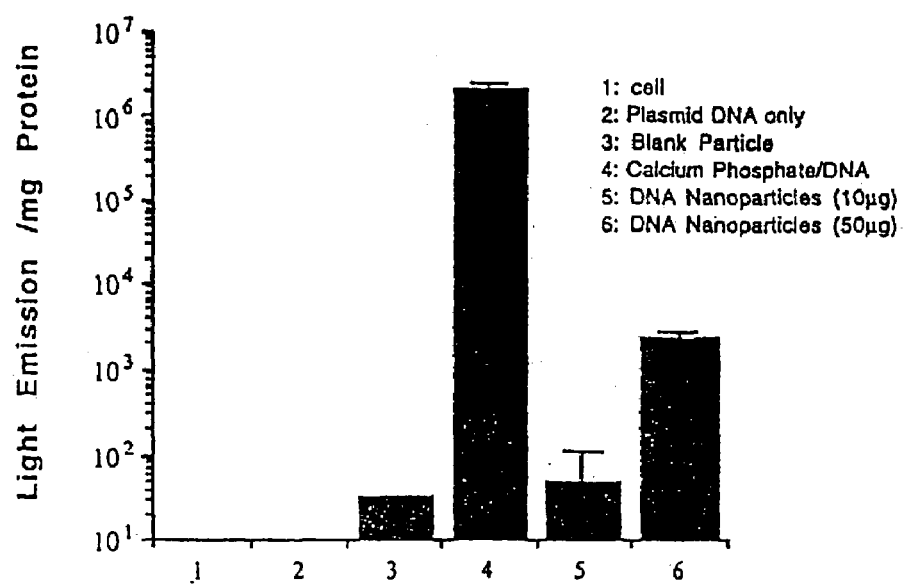
Figure 4C
PLL-PLGA-DNA Nanoparticles Transfection
1: cell
2: Plasmid DNA only
3: Blank Particle
4: Calcium Phosphate/DNA
5: DNA Nanoparticles (10μg)
6: DNA Nanoparticles (50μg)

DNA Transfection to Striated Muscle from Sustained Release Suture

Atrial Myocardial Gene Transfer from Controlled Release Polymer Coated Suture (Alkaline Phosphatase Reporter Data)

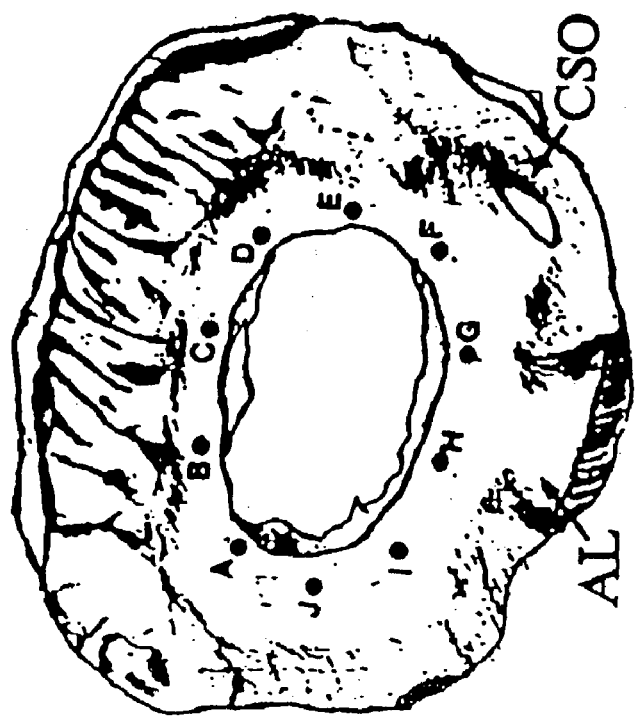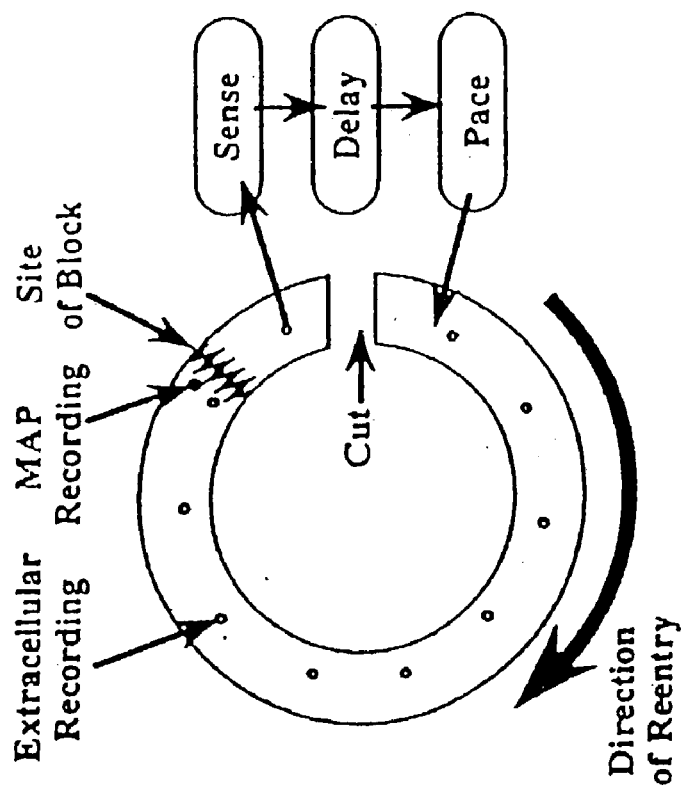
Figure 9

Figure 11
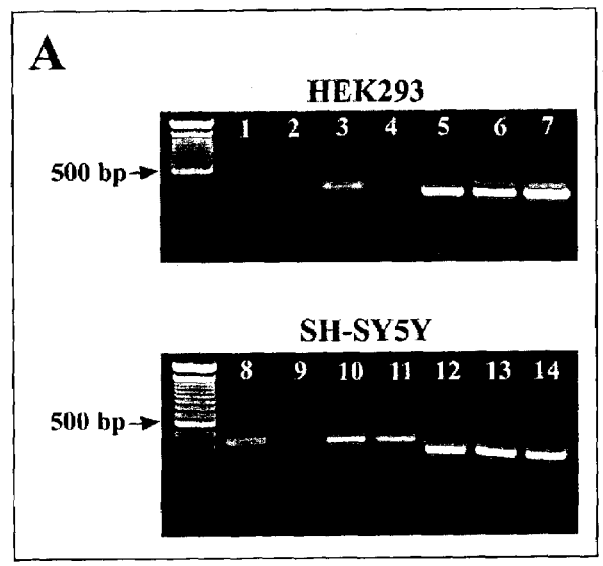
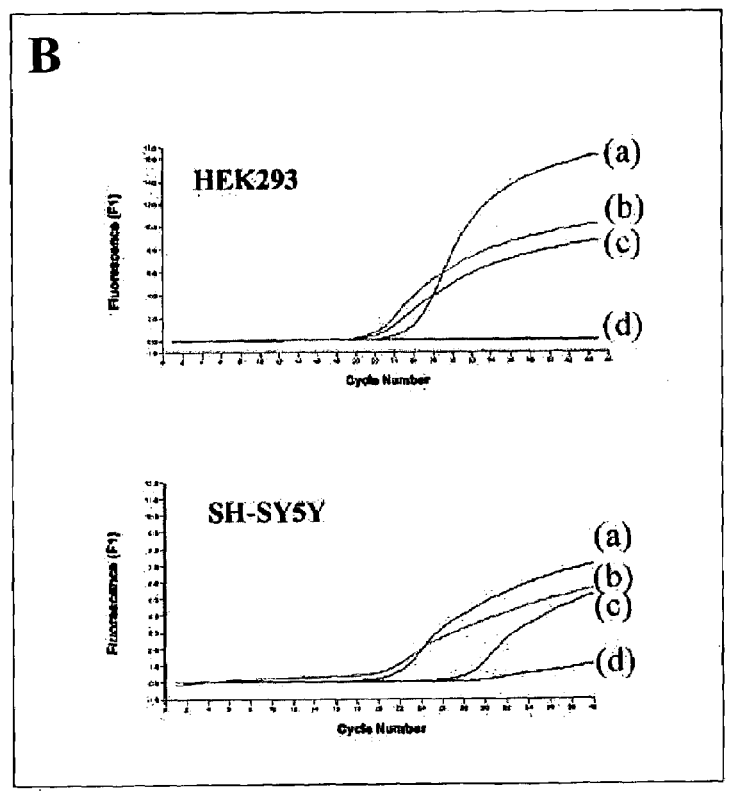

Figure 15
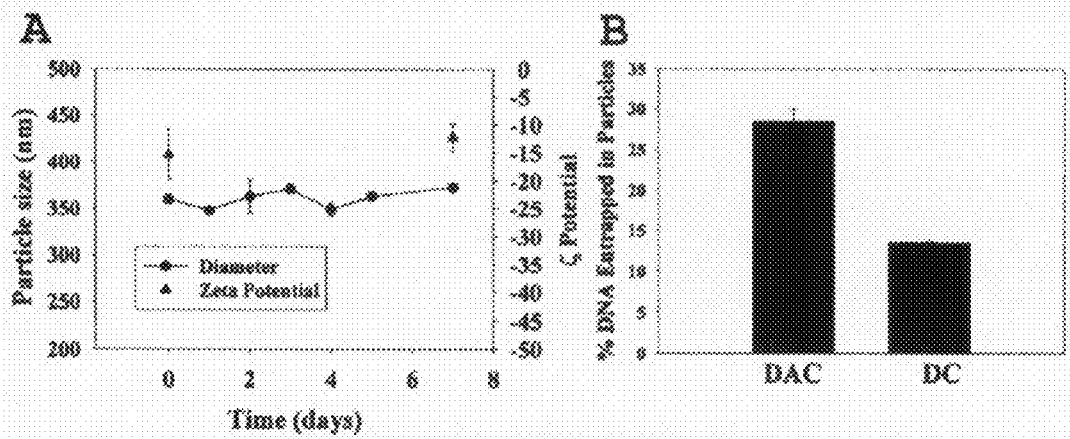
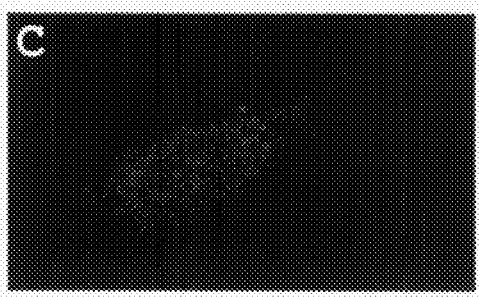
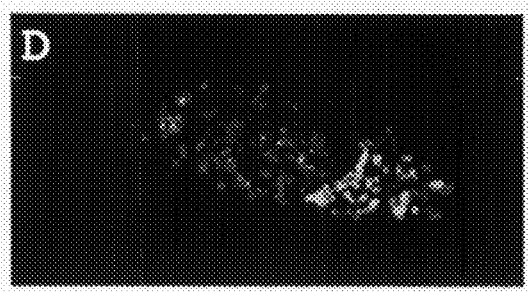 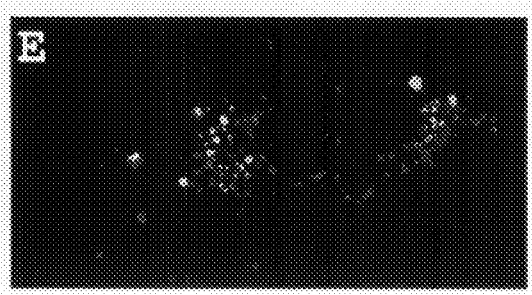
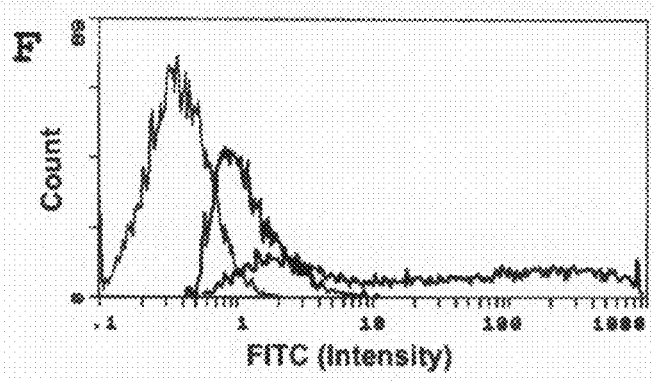

Figure 16
A
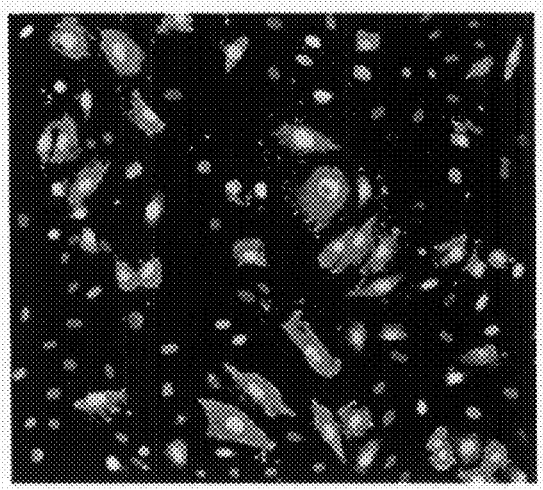
B
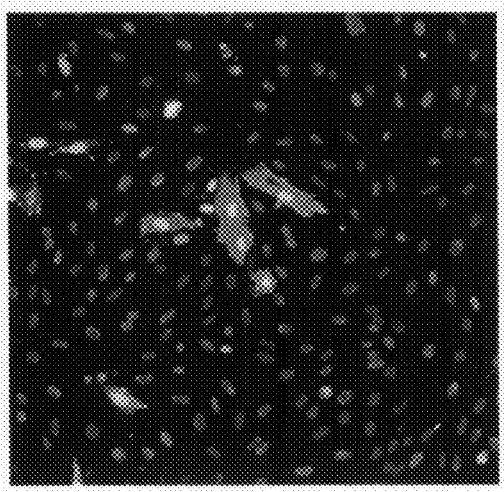
C
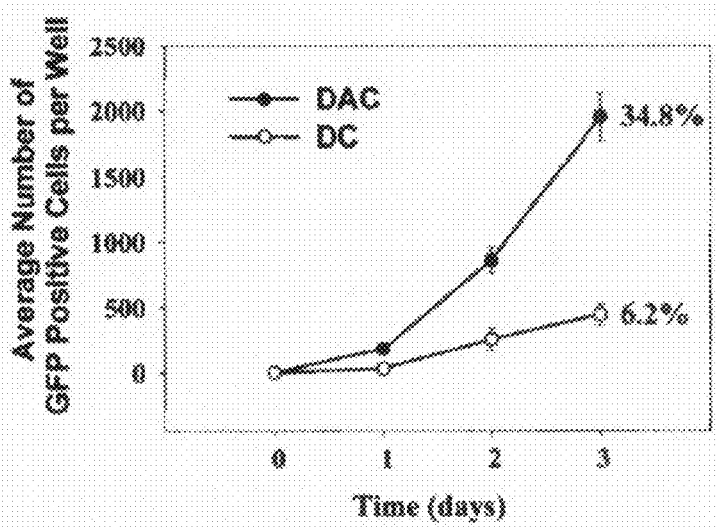
D
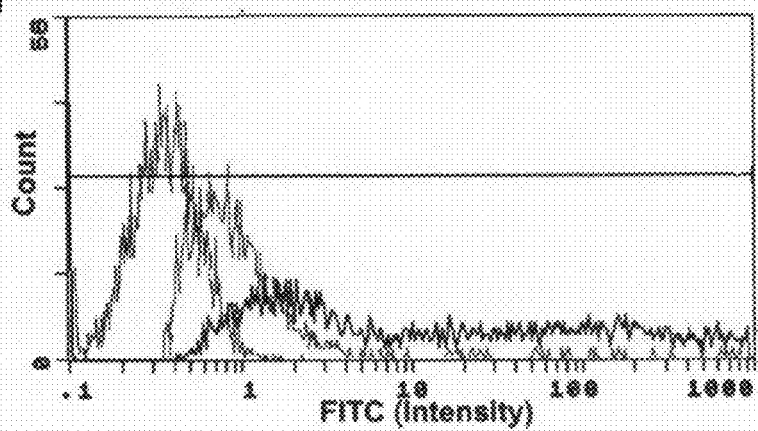

Figure 17
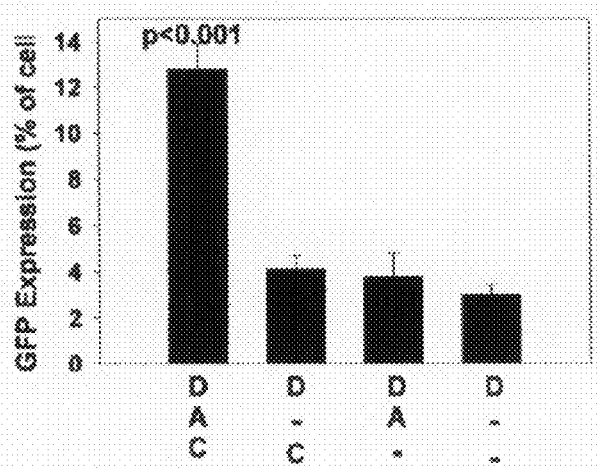
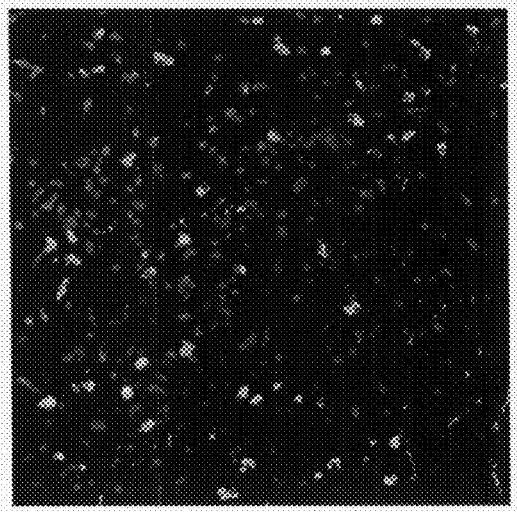
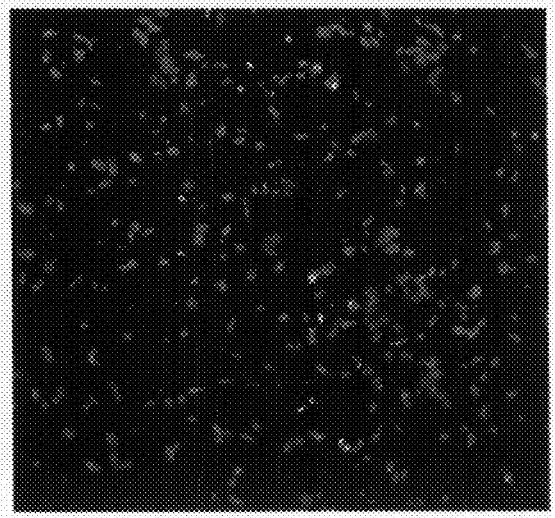

MAP duration elongation –

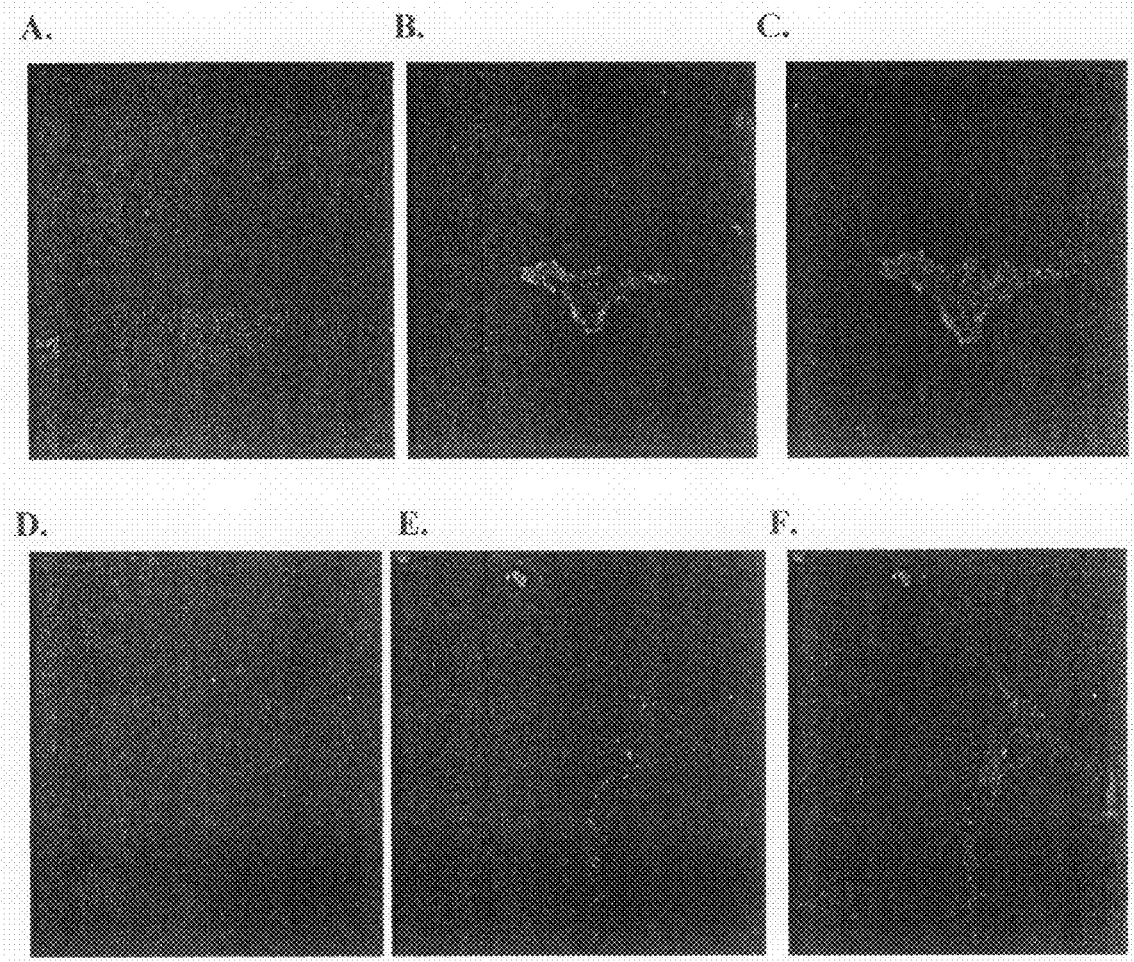

Figure 20. hMiRP1 and Q9E are membrane localized in Rat Mesenchymal Stem Cells

Confocal microscopy of rat mesenchymal stem cells (RMSC) transfected with Q9E. (A). GFP expression (B). Q9E-FLAG tagged ©. Merged image of A and B. Blue fluorescence indicates DAPI staining of nucleus.
Confocal microscopy of rat mesenchymal stem cells (RMSC) transfected with MiRP1. (D). GFP expression (E). MiRP1-FLAG tagged (F). Merged image of A and B. Blue fluorescence indicates DAPI staining of nucleus.

COMPOSITIONS AND METHODS FOR PERFORMING REVERSE GENE THERAPY

This application is a continuation-in-part application of U.S. patent application Ser. No. 09/487,851, filed Jan. 19, 2000, now U.S. Pat. No. 6,852, 704; and also claims priority to U.S. Provisional 60/374,840 filed Apr. 24, 2002, the entire disclosures of each being incorporated by reference herein.

STATEMENT REGARDING FEDERALLY SUPPORTED RESEARCH AND DEVELOPMENT

Pursuant to 35 U.S.C. §202(c) it is acknowledged that the U.S. Government has certain rights in the invention described herein, which was made in part with funds from the National Heart, Lung and Blood Institute, Grant number HL41663.

FIELD OF THE INVENTION

The present invention relates to the fields of medicine and gene therapy. More specifically, the present invention relates to an adaptation of gene therapy to the field of tissue engineering. In particular, the invention concerns the use of cells that can generate tissue in vivo ("progenitor cells") as the means for effecting so-called reverse gene therapy (RGT), an approach generally described in PCT application WO 200041731 A1.

BACKGROUND OF THE INVENTION

Re-entrant atrial flutter is a disease condition which affects many individuals. Electrophysiologic mapping techniques have lead to an enhanced understanding re-entrant atrial arrhythmias, and these advances have led to attempts to develop ablation procedures which destructively block conduction in myocardial regions involved in re-entry (Natale et al., 1996, Am. J. Cardiol. 78:1431-1433; Frame et al., 1996, Pacing Clin. Electrophysiol. 19:965-975; Cosio et al., 1996, Arch. Mal. Coeur Vaiss. 1:75-81; Cox et al., 1995, J. Thorac. Cardiovasc. Surg. 110:485-495; Cox et al., 1993, Ann. Thorac. Surg. 56:814-823; Cox et al., 1996, J. Thorac. Cardiovasc. Surg. 112:898-907).

Atrial fibrillation and atrial flutter are emerging as major clinical and public health problems for a number of reasons. The high incidence of atrial arrhythmias in the increasingly-aged population has resulted in the number of patients afflicted with atrial fibrillation or atrial flutter increasing into the millions (Prystowsky et al., 1996, Circulation 93:1262-1277; Anderson et al., 1996, Am. J. Cardiol. 78:17-21; Camm et al., 1996, Am. J. Cardiol. 78:3-11). In addition, atrial fibrillation and atrial flutter have been noted to occur very commonly following cardiac surgery, especially following coronary artery bypass surgery (Cox, 1993, Ann. Thorac. Surg. 56:405-409; Balaji et al., 1994, Am. J. Cardiol. 73:828-829; Balaji et al., 1994, J. Am. Coll. Cardiol. 23:1209-1215; Gandhi et al., 1996, Ann. Thorac. Surg. 61:1299-1309).

A number of mechanisms have been investigated to explain atrial arrhythmias, and are the basis for the conventional therapeutic approach. Re-entrant phenomena are thought to most often be the basis for atrial flutter (Gandhi et al., 1996, Ann. Thorac. Surg. 61:1666-1678; Frame et al., 1986, Circ. Res. 58:495-511; Frame et al., 1987, Circulation 5:1155-1175; Boyden et al., 1989, Circulation 79:406-416; Cosio et al., 1993, Lancet 341:1189-1193). Medications that slow atrial conduction or block down conduction through the AV-node have been useful for treatment of atrial arrhythmias (Waldo, 1994, Clin. Cardiol. 17:1121-1126, 1994; Wells et al., 1979, Circulation 60:665-673; Antman, 1996, Am. J. Cardiol. 78:67-72; Cochrane et al., 1996, Drug Ther. Bull. 34:41-45; Roden et al., 1996, Annu. Rev. Med. 47:135-48). Atrial fibrillation is believed often to result from a coalescence of multiple wavelets of impulse conduction (Moe, 1962, Arch. Int. Pharmacodyn. 1-2:183-188; Waldo, 1990, Circulation 81:1142-1143), and recent investigations have suggested that conditioned fibrillating atrium begets further atrial fibrillation (Salmon et al., 1985, Circulation 72(Suppl III):111-250; Morillo et al., 1995, Circulation 91:1588-1595; Wijffels et al., 1995, Circulation 92:1954-1968).

Gene Therapy

Gene therapy is generally understood to refer to techniques designed to deliver nucleic acids, including antisense DNA and RNA, ribozymes, viral fragments and functionally active therapeutic genes into targeted cells (Culver, 1994, *Gene Therapy: A Handbook for Physicians*, Mary Ann Liebert, Inc., New York, N.Y.). Such nucleic acids may themselves be therapeutic, as for example antisense DNAs that inhibit mRNA translation, or they may encode, for example, therapeutic proteins that promote, inhibit, augment, or replace cellular functions.

Virus vectors are among the most efficient gene therapy vectors which have been demonstrated. However, virus vectors sometimes elicit an immune response in the gene therapy host, which can inhibit the therapeutic benefit provided by the vector. Furthermore, use of retrovirus vectors can result in integration of the nucleic acid of the vector into the genome of the host, potentially causing harmful mutations. 'Naked' nucleic acid vectors, such as linear DNA vectors and plasmids, do not generally induce an immune response or integrate into the host genome, but are taken up and expressed by host cells less effectively than virus vectors.

Among the shortcomings of current gene therapy strategies, including both ex vivo and in vivo gene therapy methods, is a dearth of appropriate nucleic acids for delivery to diseased or otherwise abnormal cells. Gene therapy methods have typically involved delivery of either a nucleic acid which is or which encodes a normal (i.e. wild type) component of a cell of the type to which the nucleic acid is delivered, an antisense oligonucleotide which inhibits or prevents transcription or translation of a nucleic acid in the diseased or abnormal cells, or a ribozyme which specifically cleaves a nucleic in the diseased or abnormal cells. Although these nucleic acids may be effective in certain instances, a serious need remains for additional nucleic acids and compositions comprising the same which, when delivered to diseased or abnormal cells, alleviate, prevent, or reverse the disease or abnormality.

BRIEF SUMMARY OF THE INVENTION

The invention relates to a method of alleviating a disease or disorder in an affected animal cell. The method comprises locally delivering to the cell a reverse gene therapy vector comprising a promoter operably linked with a nucleic acid encoding a therapeutic gene product which is usually only expressed in cells of an abnormal tissue that is not afflicted with the disease or disorder. Delivery of the reverse gene therapy vector to the affected cell alleviates the disease or disorder.

In one aspect of this method, the therapeutic gene product is a protein, such as one selected from the group consisting of a defective HERG protein, a mutated subunit of HERG, Q9E-hMirp1, an apoptosis-inducing protein, transcription factor E2F1, tenascin C, bone morphogenic protein, a protein involved in synthesis of a glycosaminoglycan, a dominant negative mutant receptor protein, transcription factor NF-ATc, and a degradation resistant collagen protein. Preferably, the protein is either a defective subunit of the HERG protein, Q9E-hMirp1, or HERG (A561V) protein.

In another aspect of the method, the reverse gene therapy vector is selected from the group consisting of naked DNA, a plasmid, a condensed nucleic acid, and a virus vector comprising a nucleic acid. The reverse gene therapy vector may, for example, be a virus vector, such as an adenovirus vector, or a condensed nucleic acid. When a condensed nucleic acid reverse gene therapy vector is used, it may comprise a DNA molecule and a polycationic condensing agent.

In still another aspect of the method, the reverse gene therapy vector is a plasmid.

The polycationic condensing agent used in the method of the invention may, for example, be selected from the group consisting of poly-L-lysine and $Ca^{2+}$ ions. The promoter may be any promoter, including a constitutive promoter such as a CMV promoter or a tissue-specific promoter such as a cardiac tissue-specific promoter (e.g. the ANF promoter, the α-MyHC promoter, or the wild type HERG promoter).

The reverse gene therapy vector used in the method of the invention may further comprise a pharmacological agent-sensitive enhancer, such as a phorbol ester-sensitive enhancer. The reverse gene therapy vector may also, or alternatively, further comprise a Cre-recombinase-sensitive site.

According to the method of the invention, the reverse gene therapy vector may be delivered to the cell in a sustained-release manner. Such delivery methods may, for example, comprise delivering the reverse gene therapy vector to the cell in a form selected from a particle comprising the vector, a microparticle comprising the particle, a nanoparticle comprising the vector, an implantable device having a surface coated with a matrix comprising the vector, or a bulk material comprising the vector. The implantable device may, for example, comprise an electrode located in close proximity to a myocardial tissue of the animal, such as right atrial myocardium.

In one embodiment of the method of the invention, the cell is located outside the body of the animal. The cell may, for example, be a cultured cell, such as a cultured cell which is subsequently returned to the body of the animal from which the cell was obtained or is subsequently returned to the body of a second animal other than the animal from which the cell was obtained.

In another embodiment of the method of the invention, the cell is located inside the body of the animal. For example, the cell may be located in a cardiac tissue of the animal, such as a myocardial cell (e.g. a right atrial myocardium cell). The animal may be one which is afflicted with re-entry atrial flutter, in which event the therapeutic gene product is preferably a defective HERG protein, such as HERG (A561V) protein. Also preferably, the protein is operably linked with a cardiac tissue-specific promoter, such as one selected from the group consisting of the ANF promoter and the α-MyHC promoter.

The invention also relates to a reverse gene therapy vector for alleviating a disease or disorder in an affected cell. The vector comprises a promoter operably linked with a nucleic acid encoding a therapeutic gene product which is normally only expressed in cells of an abnormal tissue that is not afflicted with the disease or disorder. Delivery of the vector to the affected cell alleviates the disease or disorder.

In one aspect, the therapeutic gene product is a protein, such as one selected from the group consisting of a defective HERG protein, a subunit of HERG, Q9E-hMirp1, an apoptosis-inducing protein, transcription factor E2F1, tenascin C, bone morphogenic protein, a protein involved in synthesis of a glycosaminoglycan, a dominant negative mutant receptor protein, transcription factor NF-ATc, and a degradation resistant collagen protein. When the protein is a defective HERG protein, it is preferably HERG (A561V) protein or Q9E-hMirp1.

In another aspect of the reverse gene therapy vector of the invention, the vector is selected from the group consisting of naked DNA, a plasmid, a condensed nucleic acid, and a virus vector comprising a nucleic acid. In one embodiment, the vector is a virus vector such as an adenovirus vector. In another embodiment, the vector is a condensed nucleic acid, such as one comprising a DNA molecule and a polycationic condensing agent. In still another embodiment, the gene therapy vector is a plasmid.

The polycationic condensing agent of the reverse gene therapy vector of the invention may, for example, be selected from the group consisting of poly-L-lysine and $Ca^{2+}$ ions.

The promoter used in t he reverse gene therapy vector of the invention, may be substantially any promoter, including a constitutive promoter such as a CMV promoter or a tissue-specific promoter such as a cardiac tissue-specific promoter (e.g. the ANF promoter, the α-MyHC promoter, and the wild type HERG promoter).

The reverse gene therapy vector of the invention may further comprise a pharmacological agent-sensitive enhancer, such as a phorbol ester-sensitive enhancer. The reverse gene therapy vector may also, or alternatively, comprising a Cre-recombinase-sensitive site.

The invention also includes a particle, a microparticle, or a nanoparticle comprising the reverse gene therapy vector of the invention.

The invention further includes an implantable device comprising the reverse gene therapy vector of the invention, such as one having a surface coated with a matrix comprising the reverse gene therapy vector.

The present invention expands upon previously described RGT methods and provides the means for cell-based delivery and tissue engineering.

In yet another aspect of the invention, the method involves providing a plurality of progenitor cells, at least some of which comprise a disease-related polynucleotide, such that cells of the plurality express the polynucleotide; and introducing an effective amount of the plurality at the diseased site.

In a preferred embodiment, tissue develops at the diseased site which exhibits a phenotype imparted by the polynucleotide. In a more preferred embodiment, the phenotype counters or masks an effect of the disease at the diseased site.

In another preferred embodiment, the plurality of progenitor cells is made up of pluripotent embryonic stem cells, neuronal stem cells, hematopoietic stem cells, or skin stem cells.

In an even more preferred embodiment, the progenitor cells are mesenchymal stem cells or cells that have differentiated from mesenchymal stem cells. Mesenchymal stem cells expressing wt hMirp1 and the Q9E-hMirp1 and methods of use thereof are also encompassed by the present invention.

BRIEF DESCRIPTION OF THE DRAWINGS

FIG. 3 is a bar graph which indicates luciferase activity in type 293 cells transformed using DNA-containing PLGA copolymer microparticles, as described herein.

FIG. 4, comprising FIGS. 4A, 4B, and 4C is a trio of graphs which indicate properties of DNA-containing PLGA copolymer nanoparticles, as described herein. FIGS. 4A and 4B are graphs which indicate the amount of DNA released from these nanoparticles when they were incubated in vitro in TE buffer which did or did not contain SDS. FIG. 4C is a bar graph which indicates luciferase activity in type 293 cells transformed using DNA-containing PLGA copolymer nanoparticles.

FIG. 9 is a diagram which depicts placement of electrodes in the vicinity of the tricuspid annulus of a dog, as described herein.

FIG. 11: Over-expression of hMiRP1 and Q9E-hMiRP1 in stably transfected HEK293 and SH-SY5Y cell lines as shown by RT-PCR. (A). A composite gel stained with ethidium bromide. HEK293 cells results with: Lane (1) negative control (water)(2) derived from RNA from untransfected cells, or from (3) hMiRP1 and (4) Q9E-hMiRP1 transfected cells. Lanes (5-7), GAPDH controls for respective samples. SH-SY5Y cell results: Lane (8) untransfected cells, (9) negative reagent control, (10) Q9E-hMiRP1 and (11) hMiRP1 transfected cells. Lanes (12-14), GAPDH controls for respective samples 9-11. (B). Representative LightCycler real time RT-PCR assays for detection of the hMiRP1 gene with SYBR Green I Fluorescence (FI). Shown are the results from 4 HEK293 samples, where Line (b) indicates a Q9E-hMiRP1 DNA preparation with a relatively high concentration of target DNA, line (c) indicates hMiRP1, line (a) indicates a positive plasmid control, and line (d) indicates a negative control. Also shown are the results from 4 SH-SY5Y samples: Where Line (b) indicates a Q9E-hMiRP1 DNA preparation with a relatively high concentration of target DNA, line (a) indicates hMiRP1, line (c) indicates a positive plasmid control using the plasmid containing the (MiRP1 gene), and line (d) indicates a negative control.

FIG. 15: Characterization of DNA antibody heteroplexes and their transfection mechanism: (A) DNA-anti-DNA antibody-cationic lipid (DAC) heteroplexes had an initial mean particle diameter of 370±10, with a charge of −15.4±4.5 mV. Both parameters remained stable for at least one week under simulated physiologic conditions (pH 7.4, 37° C.). (B) DAC heteroplexes contained significantly more DNA than did DC lipoplexes ($p<0.002$). (C) A10 cells transfected with DAC heteroplexes containing Alexa Fluor 568 (red fluorescent)

labeled anti-DNA antibody, demonstrated cytoplasmic and nuclear presence of the anti-DNA antibody, (D) DNA (rhodamine labeled) and cationic lipid (BIODIPY labeled—green) in DAC heteroplexes, co-localized as indicated by yellow color both in the cytoplasm and the nucleus of A10 cells; (E) DC lipoplexes in comparison to D, illustrating a paucity of nuclear entry. C-E; confocal fluorescent microscopy, original magnification 400×, all shown 48 hours after transfection. (F) FACS analysis of A10 cells 48 hours after transfection. Cells were trypsinized, pooled, resuspended, and analyzed for comparison of FITC-labeled DNA uptake between DAC (red), and DC (blue) mediated transfection as compared to control (black). A10 cells transfected with DAC contained higher amounts of labeled DNA than those transfected with DC, 88% vs. 21% respectively. The result shown is one representative experiment.

FIG. 16: Increased transfection of rat arterial smooth muscle cells (A10) in vitro with DNA antibody heteroplexes: GFP expressing A10 cells after transfection with either DAC heteroplexes or DC lipoplexes formulated with the same amount of DNA (10 µg DNA) (A) Significantly greater GFP expression using DAC heteroplexes than (B) DC lipoplexes in culture after 72 hours (A and B, fluorescent micrograph, FITC and DAPI filters, original magnification 100×); (C) Percentage of A10 cells transfected over time, demonstrating significantly higher GFP expression at all time points with DAC heteroplexes compared to DC lipoplexes (p<0.001). (D) FACS analysis of GFP-transfected A10 cells. Cells (80-90% confluent culture) were trypsinized, pooled, resuspended, and analyzed after 72 hours for comparison of gene transfer efficiency between DAC (red), and DC (blue) as compared to control (black). A greater percentage of A10 cells expressed GFP following transfection by DAC than by DC: 76% vs. 11.2%; respectively. The result shown is one representative experiment.

FIG. 17: Increased transfection in vivo (pig atrial injections) after 7 days with DAC heteroplexes. (A) Greater percentages of porcine atrial myocytes were transfected in vivo with DAC heteroplexes, compared to naked DNA (D), DA, or DC p<0.001 (DAC, vs. other groups); (B) Expression pattern of GFP in porcine atrial myocardium after transfection with DC compared to greater expression (C) using DAC. (B and C), FITC/DAPI merged fluorescent micrographs, original magnification 200×.

Figure 18:
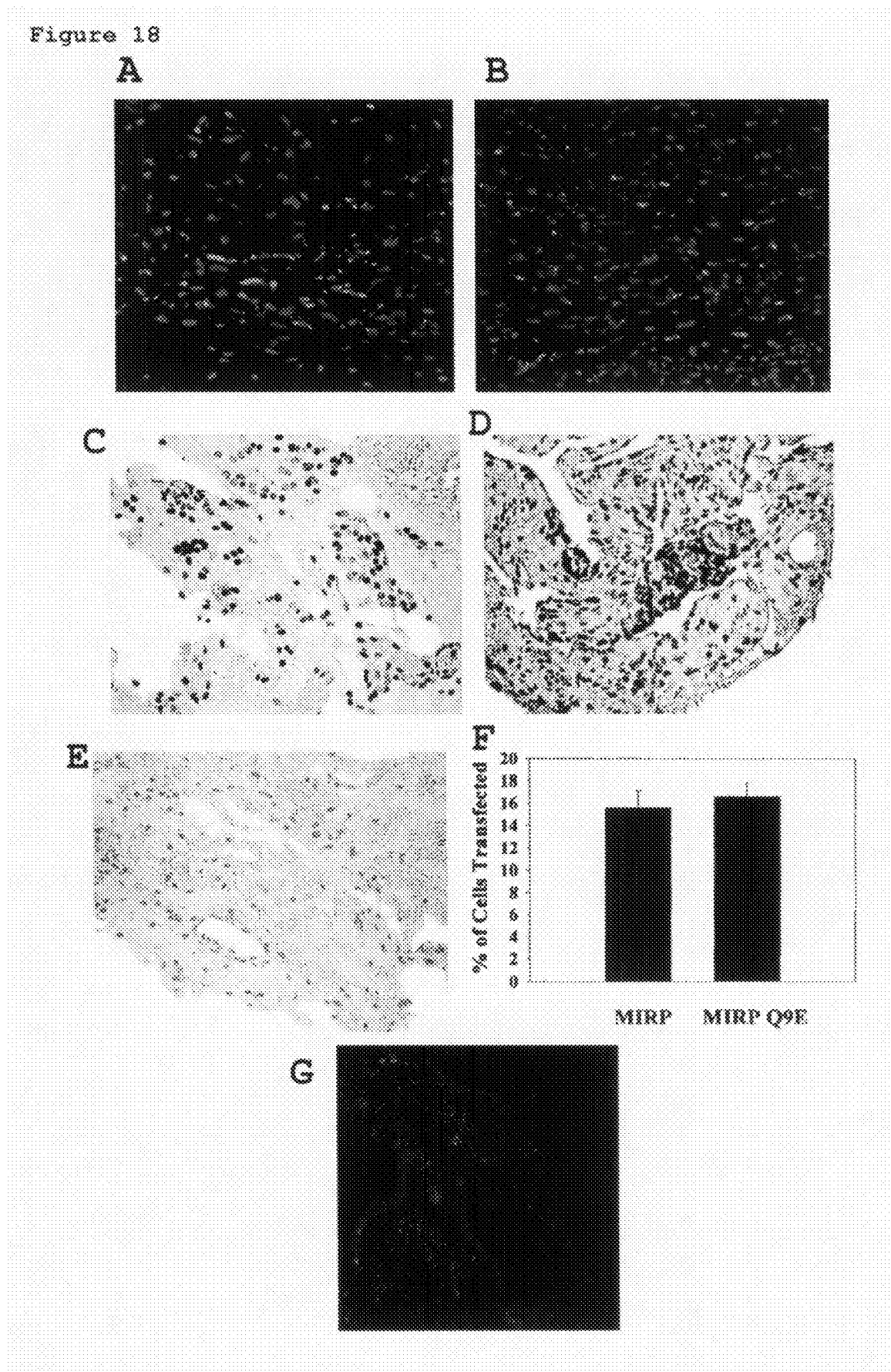

FIG. 18: Transfection of porcine atrial myocardium with hMiRP1 and Q9E-hMiRP1 bicistronic plasmids in DAC: Locally diffuse expression pattern of GFP-hMiRP1 and GFP-Q9E-hMiRP1 in porcine atrial myocardium 7 days after transfection; (A) GFP-hMiRP1 and (B) GFP-Q9E-hMiRP1 (A&B, FITC/DAPI fluorescent micrographs, original magnification 200×). Confirmation of GFP-hMiRP1 and GFP-Q9E-hMiRP1 expression using anti-GFP immunohistochemistry ), where VIP (purple) staining indicates the GFP expression in the myocardium for (C) GFP-hMiRP1 and (D)GFP-Q9E-hMiRP1; (E) representative control, non-specific IgG demonstrating a paucity of immunoperoxidase staining for GFP. (F) Bar graph indicates the percentage of cells successfully transfected via the DAC method in vivo using either the hMiRP1 or Q9E-FLAG tagged bicistronic vectors. (G): In vivo plasma membrane localization of Q9E-hMiRP1 in porcine atrial myocardium demonstrated using rhodamine-labeled anti-FLAG antibody in GFP positive (FITC) myocytes (fluorescent confocal microscopy, original magnification 600×).

Figure 19:
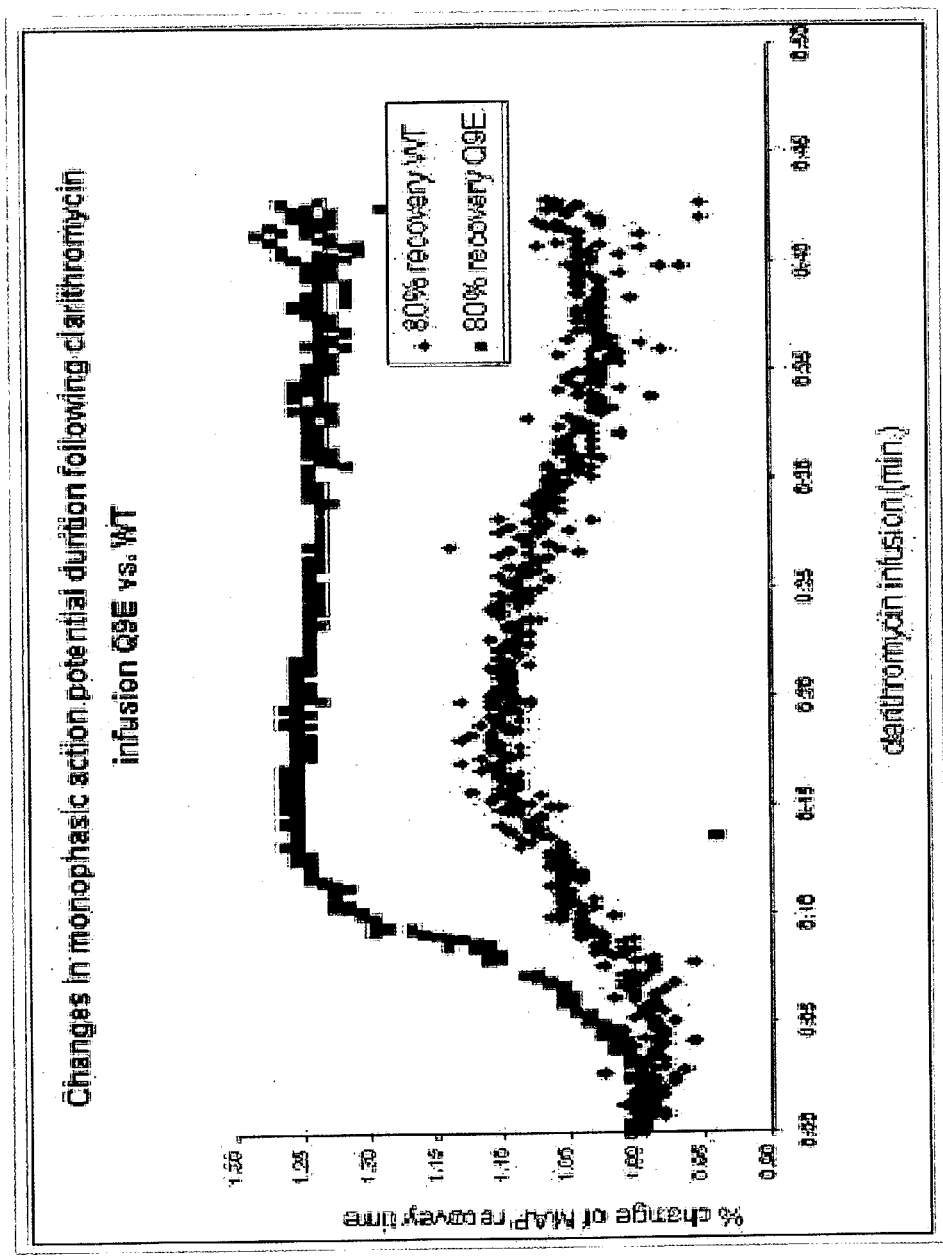

FIG. 19 is a graph showing the changes in monophasic action potential duration following clarithromycin infusion in pigs treated with wild-type hMirp1 and Q9E-hMirp1.

FIG. 20 is a series of micrographs showing that hMirp1 and Q9E-hMirp1 are membrane localized in rat mesenchymal stem cells (RMSC). Confocal microscopy of RMSC transfected with Q9E-hMirp1: (A) GFP expression; (B) Q9E-hMirp1-flag-tagged; (C) Confocal merged image of A and B, blue fluorescence indicates DAPI staining of the nucleus. Confocal microscopy of RMSC transfected with wt Mirp1: (D) GFP expression; (E) Mirp1-flag-tagged; (F) Confocal merged image of A and B, blue fluorescence indicates DAPI staining of the nucleus.

DETAILED DESCRIPTION OF THE INVENTION

The invention relates to a new method of gene therapy herein designated 'reverse' gene therapy. Traditional gene therapy methods involve using a gene vector to deliver a wild type or engineered gene or a promoter operably linked with a nucleic acid encoding a wild type or engineered protein or a wild type or engineered RNA molecule to an cell of an animal afflicted with a disease or disorder.

'Reverse' gene therapy, as described herein, refers to localized delivery of a gene therapy vector or stem cell comprising said vector to an affected cell or tissue of an animal afflicted with a disease or disorder. The nucleic acid encodes a therapeutic gene product which is usually only expressed in cells of an abnormal tissue which is not afflicted with the same disease or disorder. Such abnormal tissues include, for example, tissues afflicted with a different disease or disorder than the one being alleviated by reverse gene therapy. Because the therapeutic gene product is expressed in an abnormal tissue, expression of the therapeutic gene product in tissues other than the tissue afflicted with the disease or disorder being alleviated is generally considered by others to be undesirable (despite the 'therapeutic' designation attached to such gene products in the present disclosure). Hence, it is necessary to minimize or prevent expression of the therapeutic gene product in normal tissues by delivering the gene therapy vector or cell comprising the same, in a localized fashion, and preferably by expressing the therapeutic gene product in a tissue-specific manner. Also preferably, the gene therapy vector is administered in a sustained-release fashion in order to maximize and extend expression of the therapeutic gene product in the tissue afflicted with the disease or disorder being treated. The word "reverse" in reverse gene therapy is used to indicate a nucleic acid construct which would be harmful if expressed in one physiological setting which is delivered to a diseased physiological site in order to achieve the reverse (i.e. a beneficial) effect in a different setting.

The reverse gene therapy method of the invention is a method of alleviating a disease or disorder in an affected animal cell. This method comprises locally delivering to the cell or tissue, a gene therapy vector or a stem cell comprising said vector. The gene therapy vector comprises a promoter operably linked with a nucleic acid encoding a therapeutic gene product which is usually only expressed in cells of an abnormal tissue that is not afflicted with the disease or disorder, such as cells of a tissue afflicted with a different disease or disorder. Delivery of the gene therapy vector to the affected cell alleviates the disease or disorder in the cell. By alleviating the disease or disorder in individual affected cells of an animal afflicted with a disease or disorder, the symptoms of the disease or disorder are alleviated. In contrast with alleviation of symptoms effected by administration of non-nucleic acid-containing pharmaceutical agents, administration of the gene therapy vector of the invention results in a longer period of relief from the symptoms. If the gene therapy vector of the invention comprises a virus vector which is capable of integrating its nucleic acid into the genome of the cell or into the genome of an organelle within the cell, very long term relief may be effected, possibly enduring for the length of the animal's life.

In addition, the present inventors have discovered that a cell-based system for effecting RGT offers numerous advantages that dovetail with the need of RGT for restricted, localized effects. The key to achieving these advantages is the use, pursuant to the present invention, of progenitor cells that, once modified with the gene program of interest, establish a permanent tissue or organ having a phenotype that counters the pathological character of a physiological site to which the tissue or organ is functionally appurtenant.

A progenitor cell is essentially a stem cell that is capable of differentiation into a particular type of cell. There exists, for example, pluripotent embryonic stem cells, which can-differentiate into neurons, epithelial cells, fibroblasts and blood cells; neuronal stem cells that can develop into nerve cells; hematopoietic stem cells that grow into blood, liver and muscle cells; and skin stem cells that can differentiate into skin and nerve cells. The source of stem cells can vary from embryos and, fetal tissue to umbilical cords and adult tissues. Specifically, bone marrow, peripheral blood cells or umbilical cord blood are all sources of progenitor stem cells. Bone marrow contains both hematopoietic and mesenchymal stem cells. Pluripotent stem cells, i.e., those from which many cell types may be generated, are available from embryonal carcinoma, embryonic stem and embryonic germ cells. A progenitor cell may be a mesenchymal cell, hematopoietic cell, satellite cell, erthroid cell, neuronal cell, granulocyte-macrophage, endothelial cell or a retinal cell. All sources of progenitor cells can be obtained from unaffected or affected individuals. With respect to the latter, autotransplantation involves isolating progenitor cells from the affected subject, genetically modifying the cells and then reintroducing either differentiated or undifferentiated transformed progenitor cells into the diseased tissue of the affected subject.

For the invention, the preferred progenitor cells are mesenchymal stem cells (MSCs) or cells that have differentiated from MSCs ("MSC-differentiated cells"). Mesenchymal cells are obtained from the embryonic mesoderm, which consists of loosely packed, unspecialized cells set in a gelatinous ground substance, from which connective tissue, bone, cartilage, and the circulatory and lymphatic systems develop. MSCs are relatively easy to isolate and can be obtained by known techniques that are illustrated, for example, by Azizi et al, *Proc. Natl. Acad. Sci. USA* 95: 3908 (1999). More specifically, bone marrow can be aspirated from the iliac crest of a donor, who can be the patient to be treated in accordance with the present invention. The procedures also exist for producing a homogeneous population of MSCs in culture, see U.S. Pat. No. 5,486,359, and for modifying the MSCs with an exogenous polynucleotide, as reported in Prockop, *Science* 276: 71 (1997). Also see U.S. Pat. No. 5,591,625. These advantages, combined with their stem cell-like qualities of in situ migration and pluripotency, recommend MSCs for use in the present invention.

It is also well known that MSCs can be manipulated so as to contain a gene of interest (e.g., the naked DNA, the plasmids and vectors described further herein). These transformed MSCs can be distinguished from untransformed MSCs by their ability to survive exposure to an antibiotic. Antibiotic resistance is conveyed by a gene sequence carried on the targeting construct that also contains the gene of interest. The MSCs can then be reintroduced into a host animal so that the modified cells are incorporated by the host tissue(s). For example, see U.S. Pat. Nos. 5,591,625, 6,355, 239, and No. 6,238,960.

Although the prepared MSCs themselves can be administered therapeutically, according to the present invention, it may be more practical to administer MSC-differentiated cells in some circumstances. By exposing MSCs to appropriate culture conditions, such as to 5-azacytidine, the MSCs can be differentiated into any one of a range of mesenchymal lineage. That is, a MSC progenitor cell line expressing the disease-related polynucleotide may be cultured so as to differentiate into muscle, such as cardiomyocytes, bone or cartilage. Typically, differentiation is a multistep cellular process that requires activity of specific growth factors and/or cytokines. After undergoing several transitory phases, cell proliferation ends in terminal differentiation. At that point, the terminally-differentiated cells synthesize the cell-specific products and then mature to acquire the functional aspects of the tissue in vivo.

Other differentiated progenitor lineages include but are not limited to osteogenic, chondrogenic, tendonogenic, ligamentogenic, myogenic, marrow stromagenic, adipogenic, and dermogenic lineages. For a particular lineage, the appropriate culture conditions are determined empirically by adding and removing various trophic factors known to effect differentiation, thereby mimicking in vivo physiological conditions, as described in U.S. Pat. No. 5,942,225.

A central feature of the present invention is the selection of a disease-related polynucleotide that imparts a tissue phenotype inversely correlated, in functional or structural terms, to the disease phenotype of the subject. "Inversely correlated" means that the disease-related polynucleotide counters or masks a phenotypic trait, symptom, or mechanism that underlies the disease state of the subject.

Exemplary of such an inverse correlation, for example, is the matching up of (i) a diseased site characterized by a cellular receptor that, by virtue of the relevant pathogenesis, is expressed abnormally, in amount or structure, or is regulated abnormally, in relation to its cognate ligand, with (ii) genetically modified tissue, engendered in vivo by progenitor cells of the invention, that expresses a disease-related polynucleotide responsible, in the unrelated condition, for a countervailing expression or regulation of the same receptor or the process(es) affected by that receptor. Another inverse correlation that is adaptable to the inventive therapeutic approach would pair (i) a diseased site where the relevant pathogenesis involves undesired production of a protein, a glycoprotein, or a carbohydrate molecule (or a structure incorporating at least one of these) with (ii) genetically modified tissue that expresses a disease-related polynucleotide responsible, in the unrelated condition, for production of a species that effects an elimination of the molecule or otherwise hinders production of the structure. Conversely, the genetically modified tissue could express a substance, constitutively or otherwise, that is counterproductive in the unrelated condition but, in an RGT context, facilitates the formation of a structure that is deficient or absent at the diseased site.

A progenitor cell can be genetically engineered, pursuant to the invention, via any of a number conventional techniques so as to incorporate, for example, any one of the above described genes. Thus, a vector that incorporates a disease-related polynucleotide ("a targeting construct") can be introduced into a progenitor cell to provide cells capable of producing the protein product encoded by the desired polynucleotide. Other elements of the targeting construct may include a promoter, termination sequence, polyadenylation sequence, antibiotic resistance "marker" and "selection" sequences, and enhancer elements, such as Kozak and internal ribosomal entry site (IRES) sequences. The promoter may be the cytomegalovirus (CMV) promoter or the SV40 early promoter, which express polynucleotides constitutively. Alternatively, the promoter may be regulatable, so that the disease-related polynucleotide is only expressed under certain conditions. For example, the heparin-binding EGF-like growth factor promoter is activated upon mechanical stretch of muscles. Alternatively, the disease-related polynucleotide may be integrated into the host cell genome such that its expression is controlled by an endogenous promoter. The targeting construct also may contain signal sequences that export the disease-related polynucleotide out of the cell.

In order to produce a progenitor cell line that is stably engineered, i.e., that can sustain generations of cells, derived from a parent cell, that do not lose the ability to express the disease-related polynucleotide, a targeting construct also may contain sequences to facilitate homologous recombination. The use of homologous recombination to this end is well known and involves the exchange of genetic material located between similar, if not identical, DNA sequences, so as to integrate an exogenous DNA sequence into a cell genome. For instance, see B. Levin, GENES VII (Oxford University Press), in Chapter 14, "Recombination and Repair," at pages 415-17, 538 and 539. See also Dressler & Potter, "Molecular mechanisms in genetic recombination," *Ann. Rev. Biochem.*, 51, 727-761, 1982 and West, S. C., "Enzymes and molecular mechanisms of genetic recombination," *Ann. Rev. Biochem.*, 61, 603-640, 1992.

As an alternative to homologous recombination, the disease-related polynucleotide may be introduced into the genome of a progenitor cell by means of transposition elements, such as insertion sequences, exemplified by the cre/lox and flp/frt transposition systems Thus, a transposition element can be incorporated into the targeting construct so as to splice the disease-related polynucleotide into the genome of a progenitor cell. See Chapter 15 of GENES VII, supra, and U.S. Pat. No. 6,270,969.

A targeting construct that includes the disease-related polynucleotide, as well as the above-mentioned elements, may be introduced into a progenitor cell in vitro by any of a number of conventional techniques, such as electroporation, direct injection, heatshock, penetration with coated solid particles, liposomal delivery, DNA antibody micellular delivery, or by microencapsulation. The use of DEAEdextran and polybrene in electroporation and calcium phosphate coprecipitation can enhance the efficiency of transfection. Another, often more efficient technique involves the use of cationic liposomes, e.g., Lipofectamine 2000, a product of Invitrogen Corporation (Carlsbad, Calif.). The negatively charged DNA binds to the positively charged liposome, which results in the formation of a cationic lipid complex that delivers the exogenous DNA to the MSCs through endosomal or lysosomal activity. A DNase inhibitor may also be used to prevent degradation of the targeting construct after cell transfection.

Prior to transfection, the MSCs are seeded at an appropriate density and incubated overnight. The following day the cells are transfected via liposomes carrying the appropriate targeting construct. One day later, the MSC cells are passaged to allow for cell division. The cells are then trypsinized and replaced in medium containing an antibiotic, such as geneticin, at a concentration that is known to kill untransformed cells. This medium is changed every couple of days and exposure to antibiotic is maintained for three to four weeks to allow resistant cell colonies to grow and for non-resistant colonies to die. The transformed MSC cell colonies can be visualized by the expression of the enhanced green fluorescent protein (eGFP). Once those transformed cells have been identified they may be cultured, harvested and applied therapeutically.

In this context, the introduced amount of progenitor cells is therapeutically effective if, upon localized administration of the cells to the subject, it results in the generation of tissue that exhibits the phenotype imparted by the disease-related polynucleotide, countering the disease process of interest.

To determine how many cells are therapeutically effective, one may modify the targeting construct so as to include at least one marker such that its level of expression is indicative to that of the disease-related polynucleotide when both are operably linked to a promoter. Thus, a cultured batch of progenitor cells can be screened for the presence of the marker (i.e., by screening for fluorescence or enzymatic activity), the abundance of which will be related to the amount of the disease-related polynucleotide expressed by that batch of cells. (A batch of cells is also referred to as a "plurality" of cells.) In such fashion, one can determine how much of the protein product encoded by the disease-related polynucleotide is produced from a plurality of cells of known cell density.

The amount of protein product expressed from a batch of cells containing the disease-related polynucleotide also can be determined directly. For example, Western blotting, immunoblotting, immunohistochemistry, antibody staining, and electrophoretic/colormetric densitometry (i.e., determining the intensity of protein bands on an electrophoresis gel) can all be used to determine how much of the disease-related protein is present in a given batch of cultured, transfected cells. An "effective dose" may comprise differentiated or undifferentiated progenitor cells, or to a mixture of the two cell types.

It also is possible to screen for drugs or compounds in vitro that have an affect upon the phenotype of such transformed progenitor cells. An animal model of the disease to be countered is also useful for drug screening, as well as for determining the effectiveness of a therapeutic dose of transformed progenitor cells.

Ideally, an effective dose of progenitor cells should be introduced near or at the affected site of the recipient tissue in the affected individual. Delivery of transformed progenitor cells to a diseased site, in accordance with the present invention, can be accomplished by localized infusion or by direct injection of a suspension of transformed cells. Depending on the ultimate, differentiated cell type desired, the batch of progenitor cells may or may not have to be expanded prior to delivery to the affected individual. For example, if cell growth in vivo is typically required, as is the case for bone marrow transplantation, then in vitro expansion of cells is less critical. Most likely, however, cell expansion is required prior to administration of the transformed cells.

Alternatively, transformed progenitor cells can be implanted at or near the desired site as a pellet or tissue-engineered organoid, such as bio-artificial muscle. For instance, transformed progenitor cells may be manipulated so as to differentiate into myoblasts and adhered to a biodegradable polymer scaffold under conditions permitting growth and further development. This scaffold, which may also contain growth factors and chemicals need to facilitate development of the engineered tissue, may then be implanted into the body.

Differentiated and mature progenitor cells may be further developed in vitro to form tissues for grafting onto the disease site of the particular organ in the affected subject. However, if the resultant tissue replaces a mostly physical attribute in the diseased organ, then the graft must not induce a thrombogenic response and must also be able to withstand arterial pressure. Alternatively, if the physiological attributes of the graft are more important that its structural component, then it is necessary to ensure that those physiological properties are sustained as required when implanted into the individual.

In some instances, it may be necessary to injure or damage the recipient tissue prior to delivery of the transformed progenitor cells. For instance, to efficiently repopulate a diseased bone with transformed bone marrow cells, it may be necessary to first compromise the bone by exposing it or the affected individual to chemotherapy or other radiation. The transformed bone marrow cells will migrate to the requisite site, reestablish themselves and ultimately produce the protein of the disease-related polynucleotide. See U.S. Pat. No. 5,197,985 for a description of methodology to enhance the implantation and differentiation of MSCs obtained from bone marrow.

Preferred compositions and methods for reverse gene therapy which are described herein include compositions and methods for delivering a gene therapy vector or cell to cardiac tissue in an animal afflicted with a cardiac disease or disorder such as cardiac arrhythmias. Localized delivery of pharmaceutical agents to cardiac tissue has been described by others (e.g. Labhasetwar et al., 1998, J. Cardiovasc. Pharmacol. 31:449-455; Labhasetwar et al., 1997, Adv. Drug Del. Rev. 24:109-120; Labhasetwar et al., 1997, Adv. Drug. Del. Rev. 24:63-85; Sintov et al., 1997, Int. J. Pharm. 146:55-62; Gottsauner-Wolf et al., 1997, Am. Heart J. 133:329-334; Humphrey et al., 1997, Adv. Drug Delivery Rev. 24: 87-108; Desai et al., 1997, Pharm. Res. 14:1568-1573; Song et al., 1997, J. Controlled Release 45:177-192).

Localized delivery of an agent such as a gene therapy vector or cell comprising the same, advantageously delivers the agent only or primarily to a particular site, minimizes the amount of agent which needs to be delivered (i.e. by minimizing delivery to undesired sites), and minimizes undesirable effects caused by delivery of the agent systemically or to tissues located at a distance from the particular site. By way of example, enhanced efficacy of various anti-arrhythmic agents has been demonstrated when the agents were locally delivered, relative to the efficacy of the same agents delivered systemically (Labhasetwar et al., 1997, Adv. Drug Del. Rev. 24:109-120; Labhasetwar et al., 1997, Adv. Drug. Del. Rev. 24:63-85; Sintov et al., 1997, Int. J. Pharm. 146:55-62; Gottsauner-Wolf et al., 1997, Am. Heart J. 133:329-334; Humphrey et al., 1997, Adv. Drug Delivery Rev. 24:87-108; Desai et al., 1997, Pharm. Res. 14:1568-1573; Song et al., 1997, J. Controlled Release 45:177-192). Reduction of ventricular defibrillation thresholds has also been associated with local cardiac drug delivery (Song et al., 1997, J. Controlled Release 45:177-192).

A drawback of sustained-release drug delivery of a conventional pharmaceutical agent is the need to continuously resupply drug to the drug reservoir because of depletion or turnover of the drug. Sustained-release delivery of many anti-arrhythmics is further hindered by the relatively non-specific effect of such agents and by the fact that local delivery of such agents fails to change the nature of the underlying pro-arrhythmic myocardium. Thus, when delivery of anti-arrhythmic agent ceases, the myocardium remains pro-arrhythmic.

Traditional gene therapy methods have not been useful for treating pro-arrhythmic myocardium because of several factors. First, no reasonable candidate genes have been proposed for delivery to pro-arrhythmic myocardium. Second, delivery systems for localizing gene vector delivery to specific arrhythmogenic circuits within the heart have not been previously described. Third, numerous gene vectors suggested for gene therapy have exhibited complications relating to, among other things, systemic immunogenicity and toxicity. The present invention overcomes these shortcomings. As described herein, reverse gene therapy may be used to appropriately alter myocardial sites involved in mechanistic events leading to re-entrant arrhythmias because use of pathologic mutants of ion channel proteins defeats tachyarrhythmic conduction circuits and achieves, in essence, a "biotech ablation" of such arrhythmias. Perhaps because these mutant proteins are usually only expressed in cells of an abnormal tissue, their use to treat alleviate arrhythmias and other cardiac disease and disorders has not been contemplated by others.

HERG refers to the human ether agogo gene, which encodes a potassium channel rectifier protein that modulates myocardial $K^+$ re-entrant current. HERG (A561V) refers to a point mutation (resulting in an alanine-to-valine substitution) in this protein, which is responsible for one of the forms of the Long QT Syndrome, a hereditary disorder associated with episodes of ventricular arrhythmias and a risk of sudden death (Labhasetwar et al., 1995, Proc. Natl. Acad. Sci. USA 92:2612-2616; Schwendeman et al., 1995, Pharm. Res. 12:790-795; Labhasetwar et al., 1995, Clin. Pharmacokinet. 29:1-5; Levy et al., 1995, J. Controlled Release 36:137-147; Gibson et al., 1995, In: *Molecular Interventions and Local Drug Delivery in Cardiovascular Disease*, Edelman, Ed., W.B. Saunders Co., Ltd., London, UK, pp. 327-352; Wood et al., 1995, In: *Molecular Interventions and Local Drug Delivery in Cardiovascular Disease*, Edelman, Ed., W.B. Saunders Co., Ltd, London, UK, pp. 399-471). The HERG gene resides on chromosome 7 (q35-36), and has a length of about 3.2 kilobases. cDNA encoding HERG (A561V) protein has been incorporated into a plasmid vector by others, and this plasmid was used to define the mechanism of its role in the Long QT Syndrome (Wood et al., 1995, In: *Molecular Interventions and Local Drug Delivery in Cardiovascular Disease*, Edelman, Ed., W.B. Saunders Co., Ltd, London, UK, pp. 399-471). Expression of HERG (A561V) in *Xenopus* oocytes depressed the tail current response to various test pulses of voltage amplitudes, which indicated that HERG (A561V) becomes associated with the cell membrane following introduction of exogenous genetic material (Sanguinetti et al., 1996, Proc. Natl. Acad. Sci. USA. 93:2208).

The HERG (A561V) gene encodes a defective potassium channel rectifier. Defective HERG (A561V) protein interacts with the wild type HERG potassium channel rectifier in a dominant negative manner, thereby inhibiting $K^+$ current through the HERG membrane protein. Expression of the defective HERG (A561V) protein in the cell membrane of cardiac myocytes results in prolonged myocardial conduction. Ibutilide, a short acting Class III antiarrhythmic agent, also blocks cardiac potassium channel rectifier current and delays myocardial conduction. Ibutilide has been administered to patients to prevent re-entrant atrial flutter. Because both ibutilide and defective HERG (A561V) protein inhibit $K^+$ current through the HERG membrane protein, administration of defective HERG (A561V) protein to a patient afflicted with re-entrant atrial flutter using a reverse gene therapy method as described herein will relieve this condition. Prior to ethical use of this reverse gene therapy method on human patients, the method is tested using dogs. Dogs are utilized in these studies, because of the extensive prior work by the inventors and many others on dog models of cardiac arrhythmias and, in particular, atrial flutter (e.g. Kirshenbaum et al., 1996, Develop. Biol. 179:402-411; Cox et al., 1995, J. Thorac. Cardiovasc. Surg. 110:485-495). Dog myocardium is thus an art-recognized model of human myocardium, at least for the purposes of assessing the effectiveness of alleviating re-entrant atrial flutter.

In the another aspect of the invention, vectors and cells comprising the cardiac potassium channel missense mutation, Q9E-hMiRP1, are provided for use in gene therapy protocols for cardiac arrhythmias. This gene abnormality is another cause the Long QT syndrome (LQTS). However, individuals who carry the Q9E-hMiRP1 variant are predisposed to developing the (LQTS) only following clarithromycin administration. Since Q9E-hMiRP1's electrophysiological mechanism of action, diminished potassium currents resulting in delayed myocardial repolarization, is comparable to that of Class III anti-arrhythmic agents, Q9E-hMiRP1 was assessed in gene therapy protocols for site-specific treatment of re-entrant atrial cardiac arrhythmias. The atrial use of Q9E-hMiRP1 should prove safe and efficacious, since LQTS characteristically causes ventricular, but not atrial arrhythmias. Furthermore, the possible use of clarithromycin to pharmacologically control the conduction effects of overexpressed Q9E-hMiRP1 provides a means to control the system. Two bicistronic plasmid DNA gene vectors with either hMiRP1 or Q9E-MiRP1 and Green Fluorescent Protein (GFP), plus a C-terminus (of the hMiRP1 or of the Q9E-hMiRP1) coding region for the FLAG (MDYKDDDDK; SEQ ID NO: 1) peptide were assessed. We generated two stable cell lines using HEK293 and SH-SY5Y (human cell lines), over-expressing the genes of interest, confirmed by real time RT-PCR and Western blots. The expected plasma membrane localization of each overexpressed transgene was confirmed by immunofluorescent confocal fluorescent microscopy using anti-FLAG antibody. Patch clamp studies demonstrated that cells transfected with Q9E-hMiRP1 plasmid DNA exhibited significantly reduced potassium currents, but only with clarithromycin administration. A novel plasmid DNA delivery system was formulated for use in our animal studies of the hMiRP1 vectors, which was composed of DNA-anti-DNA antibody cationic lipid (DAC) heteroplexes. In vitro and in vivo studies, using DAC heteroplexes containing anti-DNA antibodies with nuclear targeting capability, demonstrated significantly increased transfection compared to naked DNA, and DNA-cationic lipid complexes. Pig atrial myocardial injections of DAC heteroplexes demonstrated 16% of regional cardiac myocytes transfected using the Q9E-hMiRP1 plasmid, and 15% of cells with the hMiRP1 vector. It is concluded that the present studies demonstrate that site-specific gene therapy for atrial arrhythmias is feasible using plasmid vectors for over-expressing ion channel mutations that have electrophysiological effects comparable to class III anti-arrhythmic agents.

Although the compositions and methods described herein focus on use of HERG (A561V) and Q9E-hMirp1, one or more of the other point mutations which have been described in the human ether agogo gene may be similarly used (e.g. Labhasetwar et al., 1995, Proc. Natl. Acad. Sci. USA 92:2612-2616; Schwendeman et al., 1995, Pharm. Res. 12:790-795; Labhasetwar et al., 1995, Clin. Pharmacokinet. 29:1-5; Levy et al., 1995, J. Controlled Release 36:137-147; Gibson et al., 1995, In: *Molecular Interventions and Local Drug Delivery in Cardiovascular Disease*, Edelman, Ed., W.B. Saunders Co., Ltd., London, UK, pp. 327-352). Alternatively, re-entrant circuit block can elicited by localized delivery and expression of the transcription factor, E2F1, which causes apoptosis in mature myocytes (Levy 1995, In: *Molecular Interventions and Local Drug Delivery in Cardiovascular Disease*, Edelman, Ed., London, UK: W.B. Saunders Co., Ltd.; Anderson et al., 1995, J. Biomed. Mater. Res. 29:1473-1475), thereby creating a devitalized region (by means of gene-induced apoptosis) within a re-entry loop.

Localization of delivery of an agent encoded by a nucleic acid can be enhanced by use of a tissue-specific or physiologically responsible promoter operably linked with the nucleic acid encoding the agent. Numerous tissue-specific and physiologically responsible promoters have been described. For example, tissue specific promoters and physiologically responsible promoters include, but are not limited to the sm22alpha promoter, which specifically promotes expression of genes in arterial smooth muscle cells (Solway et al., 1995, J. Biol. Chem. 270:13460-13469) and the tenascin-C promoter, which specifically promotes expression of genes in proliferating cells in response to the presence of matrix metalloproteinase-modified collagens (Chiquet et al., 1996, Biochem. Cell Biol. 74:737-744; Copertino et al., 1997, Proc. Natl. Acad. Sci. USA 94:1846-1851).

A physiologic responsive promoter is a nucleotide sequence regulating downstream DNA expression in response to a change in the regional physiology such as, for example, an alteration in the extracellular matrix (i.e. collagen breakdown or denaturation), an increase in regional temperature to the febrile range, or a response to a change in blood pressure or blood flow.

In the reverse gene therapy compositions and methods of the invention for treatment of cardiac arrhythmias, the promoter is preferably a cardiac tissue-specific promoter, such as the c-myosin heavy chain promoter ($\alpha$-MyHC; Anderson et al., 1995, Tissue Eng. 1:323-326; Villa et al., 1995, Circ. Res. 76:505-513) or the atrial natriuretic factor promoter (ANF; Guzman et al., 1996, Circulation 94:1441-1448). Of course, non-tissue-specific promoters (e.g. the wild type HERG promoter) and constitutive promoters (e.g. a cytomegalovirus {CMV} promoter) may be used in the gene therapy vector of the invention.

Localized expression of a therapeutic gene product can be enhanced in a reverse gene therapy method by delivering a gene therapy vector having a nucleic acid which comprises a pharmacological agent-sensitive enhancer element in addition to the portion of the nucleic acid encoding the therapeutic gene product. A variety of such pharmacological agent-sensitive enhancer agents have been described, such as those which enhance gene expression in response to administration of a phorbol ester to a cell which comprises a nucleic acid having such an enhancer element (Desai et al., 1996, Pharm. Res. 13:1838-1845; Levy et al., 1996, Drug Delivery 3:137-142; Song et al., 1997, J. Controlled Release 43:197-212). Localized enhancement of expression of the therapeutic gene product can be effected by localized delivery of the gene therapy vector coupled with systemic delivery of the pharmacological agent corresponding to the enhancer element, by systemic delivery of the gene therapy vector coupled with localized delivery of the pharmacological agent corresponding to the enhancer element, or, preferably, by localized delivery of both the gene therapy vector and the pharmacological agent corresponding to the enhancer element.

Expression of a gene product encoded by the gene therapy vector of the invention can be rendered terminable by incorporating a Cre-recombinase sensitive site in the nucleic acid of the gene therapy vector of the invention, as described (Hammond et al., 1997, Analyt. Chem. 69:1192-1196). Expression of the gene product in a cell transformed using the gene therapy vector of the invention is terminated by delivering a second vector to the cell, wherein the second vector encodes Cre-recombinase.

In an alternate embodiment of the invention, the gene therapy vector of the invention encodes a protein which, when expressed in a cell, induces apoptosis of the cell. Such proteins include, for example the transcription factor E2F1 and transcription factors normally encoded by viruses (Levy, 1995, In: *Molecular Interventions and Local Drug Delivery in Cardiovascular Disease*, Edelman, Ed., London, UK: W.B. Saunders Co., Ltd.; Anderson et al., 1995, J. Biomed. Mater. Res. 29:1473-1475; Martin et al., 1995, Nature 375:691-694).

Other contemplated embodiments of the invention include, but are not limited to, the following:

Delivery of a gene therapy vector encoding a mutant tenascin C protein associated with a disease state to cardiac or coronary artery tissue, in order to limit or prevent progression or development of cardiac valve obstruction or coronary artery obstruction. Tenascin C normally organizes progressive deposition of extracellular matrix. In certain disease states, however, expression of mutant tenascin C proteins lead to repression of extracellular matrix production (Nakao et al., 1998, Am. J. Pathol. 152:1237-1245).Delivery of a gene therapy vector encoding a bone morphogenic protein (BMP) under the transcriptional control of a mutant BMP promoter associated with a disease state to a bone fracture site or to a bone site at risk of fracture (e.g. bone non-union sites, sites at which reconstructive surgery has been performed, and cranio-facial). In certain disease states, mutant BMP promoters lead to overexpression of BMP (Kaplan et al., 1998, Biochem. Pharmacol. 55:373-382).

Delivery of a gene therapy vector comprising at least a portion of a mutant gene associated with one or more mucopolysaccharidoses to a glycosaminoglycan- (GAG-) deficient site or to a biomechanically compromised site (e.g. a joint, tendon, or heart valve) in the body of an animal. As is well known, various mutant genes associated with one or more mucopolysaccharidoses result in overexpression of GAG in the affected tissue (Froissart et al., 1998, Clin. Gen. 53:362-368).

Delivery of a gene therapy vector encoding a mutant gene, expression of which mutant gene is associated with apoptosis in a disease state, to cells or tissue which contributes to a different disease state (e.g. delivery of an apoptosis-inducing gene to myocardium cells which form all or part of conduction pathway associated with arrhythmia). Numerous mutant genes are known, expression of which mutant gene is associated with apoptosis in a disease state (e.g. Nishina et al., 1997, Nature 385:350-353).

Delivery of a gene therapy vector encoding a mutant gene encoding a dominant negative mutant gene product associated with a disease state to cells or tissue which is affected by a disease state associated with the normal (i.e. non-mutant) form of the gene product. By way of example, dominant negative mutant variants of numerous cell-surface receptors are known, such as dominant negative mutants wherein one or more inoperative receptor subunits ablate the activity of a multi-subunit receptor (e.g. Kim et al., 1998, J. Clin. Invest. 101: 1821-1826).

Delivery of a gene therapy vector encoding therapeutic gene product which is usually only expressed in cells of an abnormal tissue to facilitate implantation of engineered tissue (e.g. cultured organ tissue) into an animal. For example, a vector comprising a disease-associated gene could be used to favorably modify a tissue prior to implantation of the tissue. By way of specific example, a gene that normally encodes a product which, when expressed induces a skeletal defect (e.g. a gene described by Kaplan et al., 1998, Biochem. Pharmacol. 55:373-382), may be delivered to a tissue-engineered heart valve prior to implantation of the valve in a patient, in order to prevent the valve from calcifying.

Delivery of a gene therapy vector encoding an uncontrollable mutant of the transcription factor NF-ATc to cardiac tissue of a post-natal individual to facilitate development of a cardiac valve. The role of transcription factor NF-ATc in abnormal cardiac valve formation has been described (Ranger et al., 1998, Nature 392:186-190).

Delivery of a gene therapy vector comprising a pressure- or flow-unresponsive mutant tenascin C gene (or cDNA) to cardiac tissue to retard or prevent cardiac valve obstruction. Such mutant tenascin C genes have been described (e.g. Huang et al., 1995, Nature 378: 292-295).

Delivery of a gene therapy vector encoding a degradation resistant protein normally associated with a disease state to cells or tissue affected by a different disease state associated with the corresponding normal (i.e. degradation sensitive) form of the protein. For example, a gene therapy vector encoding a mutant collagen protein which is resistant to degradation by matrix metalloproteinase (MMP) may be delivered to a cell to block MMP cascade-integrin signaling (King et al., 1997, J. Biol. Chem. 272:28518-28522).

Delivery of a gene therapy vector comprising a gene having a deletion therein, relative to the wild type gene, wherein expression of the gene having the deletion is normally associated with a disease state, but when the gene therapy vector is delivered to cells or tissue affected by a different disease state, expression of the gene having the deletion alleviates or inhibits the different disease state. For example, chromosomal deletions such as the chromosome 22 deletions associated with cardiac defects (e.g. those described by Rauch et al., 1998, Am. J. Med. Gen. 78:322-331) may be used to inhibit heart valve calcification through by delivering vectors comprising antisense constructs corresponding to the deleted regions of chromosome 22. Delivery of such vectors to heart valve tissue suppresses differentiation of potentially calcifying cells in cardiac valves and blood vessels.

Delivery of an effective dose of progenitor cells comprising any of the constructs or vectors described above The Reverse Gene Therapy Vector of the Invention The invention includes a reverse gene therapy vector and cells comprising the same which are useful for alleviating a disease or disorder. This reverse gene therapy vector of the invention comprises a promoter operably linked with a nucleic acid encoding a therapeutic gene product which is normally only expressed in cells of an abnormal tissue that is not afflicted with the same disease or disorder. Delivery of the vector to the cell alleviates the disease or disorder. Optionally, the vector is provided in plurality of progenitor cells.

The therapeutic gene product encoded by gene therapy vector of the invention may, for example, be a protein, a ribozyme, an antisense RNA molecule, or another molecule which, when expressed in a normal cell, causes the normal cell to exhibit a symptom associated with a disease or disorder but which, when expressed in a cell to which the gene therapy vector of the invention is delivered, alleviates a symptom of a disease or disorder which affects the cell. Proteins which may be encoded by the gene therapy vector of the invention include defective HERG proteins, HERG (A561V) protein, Q9E-hMirp1, apoptosis-inducing proteins, and transcription factor E2F1.

The reverse gene therapy vector of the invention may be substantially any nucleic acid vector which is now known or hereafter developed. Exemplary vectors include, but are not limited to naked DNA vectors, plasmids, condensed nucleic acids, and virus vectors. In a preferred embodiment of the reverse gene therapy vector of the invention, the vector is a plasmid, and more preferably comprises both a plasmid and a condensing agent such as poly-L-lysine or $Ca^{2+}$ ions. When the vector is a virus vector, the virus vector is preferably an adenovirus vector.

Plasmid DNA transformation of mammalian cells results in plasmid DNA residing in the nucleus of the transfected cell, wherein the plasmid not incorporated into a chromosome. Transient episomal expression of plasmid DNA generally occurs following transformation (Dowty et al., 1995, Proc. Natl. Acad. Sci. USA 92:4572-4576; Wolff et al., 1996, Hum. Mol. Genet. 1:363-369; Fritz et al., 1996, Hum. Gene Ther. 7:1395-404). Plasmid transformation of cardiac and skeletal striated muscular tissue, either cardiac or skeletal has been demonstrated following administration of naked DNA to such tissue, and expression of the DNA in the transformed cells has been observed to persist for months (Dowty et al., 1995, Proc. Natl. Acad. Sci. USA 92:4572-4576; Wolff et al., 1996, Hum. Mol. Genet. 1:363-369; Fritz et al., 1996, Hum. Gene Ther. 7:1395-404). Alternatively, a gene therapy vector, such as certain virus vectors, may be used, wherein the vector causes the nucleic acid carried thereby to be integrated into the host cell genome.

In one embodiment, the gene therapy vector of the invention is preferably administered to a cell or tissue of an animal in a sustained-release manner. Numerous methods have been described for effecting sustained release of a nucleic acid vector such as a gene therapy vector, and all known and hereafter-developed methods for achieving sustained release of a nucleic acid vector can be used in accordance with the compositions and methods of the invention. The gene therapy vector of the invention is preferably DNA in the form of a plasmid, particularly condensed plasmid DNA incorporated into particles, microparticles, nanoparticles, a bulk material, or a coating present at a surface of an implantable device. Preferred nucleic acid vector compositions and methods of using them to administer a vector, such as the gene therapy vector of the invention, are described in co-pending U.S. patent applications having attorney docket numbers 7600-30 (CHOP-0011), 7600-29 (CHOP-0060), and 7600-24 (CHOP-0062), each of which was filed on the same date as the present disclosure, and each of which is incorporated herein by reference.

When the gene therapy vector of the invention comprises a gene therapy vector for delivering a therapeutic gene product to a cardiac tissue in order to alleviate a cardiac arrhythmia, the vector is preferably delivered to myocardial tissue in the animal. When the cardiac arrhythmia is attributable to re-entrant atrial flutter, the vector is preferably delivered locally to the right atrial myocardium of the animal, and is more preferably delivered in a sustained-release manner. Delivery of the vector to a myocardial tissue may be effected by implanting a device (e.g. an implantable device comprising an electrode, such as a cardiac rhythm modulator or pacemaker) having a surface coated with a matrix comprising the vector in close proximity to the myocardial tissue. Preferably, the matrix is biodegradable and thereby delivers the vector to the tissue in a sustained-release manner.

The implantable device may be one which is made and used for the sole purpose of delivering the reverse gene therapy vector of the invention to the animal, or the device may be one which is applied to the surface of or inserted within the body of the animal for a purpose other than merely delivering the reverse gene therapy vector of the invention to the animal. By way of example, the implantable device may be a plurality of microspheres which comprise the reverse gene therapy vector of the invention and which are implanted into the body of the animal for the sole purpose of delivering the vector to the animal. Further by way of example, the implantable device may be a pacemaker having a surface coated with a matrix comprising the reverse gene therapy vector of the invention; the pacemaker is implanted in the vicinity of the animal's heart, both to modulate the animal's heartbeat when necessary and to deliver the vector to a cardiac tissue or to another tissue in close proximity to or in fluid communication with the coated surface of the pacemaker.

The reverse gene therapy vector of the invention may be incorporated into a coating of virtually any medical device. The coated devices provide a convenient means for local administration of the vector. For example, the vector may be incorporated into coatings for degradable and non-degradable sutures, orthopedic protheses such as supporting rod implants, joint protheses, pins for stabilizing fractures, bone cements and ceramics, tendon reconstruction implants, prosthetic implants, cardiovascular implants such as heart valve prostheses, pacemaker components, defibrillator components, angioplasty devices, intravascular stents, acute and in-dwelling catheters, ductus arteriosus closure devices, implants deliverable by cardiac catheters such as atrial and ventricular septal defect closure devices, urologic implants such as urinary catheters and stents, neurosurgical implants such as neurosurgical shunts, ophthalmologic implants such as lens prosthesis, thin ophthalmic sutures, and corneal implants, dental prostheses, internal and external wound dressings such as bandages and hernia repair meshes, pacemakers and other cardiac rhythm modulation devices, cardiac electrode leads, and other devices and implants, as will be readily apparent to the skilled artisan.

The reverse gene therapy compositions and methods of the invention can be used to transforms cells located outside the body of the animal or cells located within the body of an animal. Following transformation of cells outside the body of the animal, the cells may be cultured, returned to the body of the same animal, or administered to the body of another animal of the same or different species, using substantially any known or subsequently developed method. In a preferred embodiment, the cells are the MSCs described above.

When the reverse gene therapy vector of the invention is delivered in the form of a particle which comprises the vector, the particle may be substantially any size. Preferably, the particle is a microparticle having a diameter less than about 900 micrometers, and preferably less than about 500 micrometers. Even more preferably, the particle is a nanoparticle having a diameter less than about 1 micrometer, and preferably less than about 600 nanometers. The vector may be present only on the surface of the particles, only at an interior portion of the particles, only in one or more layers of material in the particle, or throughout the particle. The particle preferably comprises a biocompatible material, and more preferably comprises a biodegradable material such as a polylactate-polyglycolate copolymer. Of course, substantially any known biocompatible polymeric or non-polymeric material may be used to form the particles, so long as at least a portion of the vector in or on the particle can be taken up by a cell which contacts the particle or is in fluid communication with the particle.

Cellular uptake of the gene therapy vector of the invention may be enhanced by incorporating a specific cell surface receptor protein into the vector (e.g. fibroblast growth factor (FGF) or transferring. Intracellular processing of the plasmid DNA within a lysosomal or endosomal compartment within the cell may be modulated by incorporating a lysosomotropic agent (e.g. sucrose or chloroquine) in order to reduce intracellular nuclease-mediated hydrolysis of the nucleic acid of the vector.

The reverse gene therapy vector preferably comprises a condensing agent. Condensation of DNA using polycations such as polylysine has also been demonstrated to enhance plasmid transfection by facilitating cell entry, possibly by encouraging nanoparticulate formation and protecting the DNA from nuclease mediated hydrolysis both extracellularly and within intracellular lysosomal or endosomal compartments. A preferred condensing agent is the polycation, polylysine.

The chemical identity of the condensing agent is not critical. The ability of a condensing agent to condense DNA or another nucleic acid or nucleic analog may be assessed using numerous methods known in the art. Effective amounts of such condensing agents may similarly be determined using these methods. For example, DNA condensation may be measured by comparing the kinetics in solution of condensed DNA and uncondensed DNA, and then further comparing the kinetics in the presence of a surfactant such as a detergent. It may also be measured by changes in the surface ?-potential of the DNA in solution (Wolfert et al., 1996, Human Gene Therapy 7:2123-33), or by visualizing the DNA using an electron microscope (Laemmli, 1975, Proc. Natl. Acad. Sci. USA 72:4288-4292) or an atomic force microscope (Wolfert et al., 1996, Gene Therapy 3:269-273).

One preferred family of condensing agents is the polylysines. Polylysines are polypeptides of varying lengths, comprising lysine residues, which are positively charged at human physiological blood pH. The lysine residues can be D-lysine residues, L-lysine residues, or a mixture of the two enantiomers; poly-L-lysine is preferred. Polylysine has been demonstrated to be an efficacious DNA condensing agent (Laemmli, 1975, Proc. Natl. Acad. Sci. USA 72:4288-4292; Wolfert et al., 1996, Gene Therapy 3:269-273). The polylysines which are useful as condensing agents in the compositions and methods of the invention include all variants of polylysine, regardless of length, linear, branched, or cross-linked structure, conformation, isomerization, or chemical modification, that are capable of condensing DNA or other polyanionic bioactive agents. Exemplary chemical modifications include methylation (Bello et al., 1985, J. Biomol. Struct. Dyn. 2:899-913) and glycosylation (Martinez-Fong et al., 1994, Hepatology 20:1602-1608). Such modifications may be made before or after synthesis of the polylysine. Other condensing agents which may be used to condense DNA and other nucleic acids include elemental cations, particularly divalent cations such as $Mg^{2+}$ or $Ca^{2+}$. Such cations may, for example, be used in the form of salts, such as $MgCl_2$ or $CaCl_2$. Other suitable elemental cations include $Co^{3+}$ (particularly in the form of cobalt hexamine, $Co(NH_3)_6^{3+}$, or cobalt pentamine), $La^{3+}$, $Al^{3+}$, $Ba^{2+}$ and $Cs^+$. These cations are generally used in the form of a salt, particularly halide salts such as chloride and bromide salts, but other salts may be used as well.

It is understood that the ordinarily skilled physician or veterinarian will readily determine and prescribe an effective amount of the compound to alleviate the disease or disorder in the subject. In so proceeding, the physician or veterinarian may, for example, prescribe a relatively low dose at first, subsequently increasing the dose until an appropriate response is obtained. It is further understood, however, that the specific dose level for any particular subject will depend upon a variety of factors including the activity of the specific compound employed, the age, body weight, general health, gender, and diet of the subject, the time of administration, the route of administration, the rate of excretion, any drug combination, and the severity of the disease or disorder to be alleviated.

The invention encompasses the preparation and use of pharmaceutical compositions comprising the reverse gene therapy vector or cells containing the same as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. Administration of one of these pharmaceutical compositions to a subject is useful for alleviating a disease or disorder in the subject, as described elsewhere in the present disclosure.

As used herein, the term "pharmaceutically acceptable carrier" means a chemical composition with which the active ingredient may be combined and which, following the combination, can be used to administer the active ingredient to a subject.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0. 1% and 100% (w/w) active ingredient.

In addition to the active ingredient, a pharmaceutical composition of the invention may further comprise one or more additional pharmaceutically active agents. Particularly contemplated additional agents include condensing agents such as polylysine.

Controlled- or sustained-release formulations of a pharmaceutical composition of the invention may be made using conventional technology.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intravenous, intraarterial, intramuscular, or intrasternal injection and intravenous, intraarterial, or kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension. This suspension may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

By "nucleic acid" is meant any homopolymer or heteropolymer of deoxyribonucleosides, ribonucleosides, or nucleoside analogs. The nucleotide analogs may be any compound known in the art to be or subsequently discovered to be useful as a structural or functional analog of a ribonucleoside or a deoxyribonucleoside. Nucleotide analogs include, but are not limited to nucleotides comprising bases other than the five biologically occurring bases (adenine, guanine, thymine, cytosine and uracil). The monomers of the nucleic acid may be connected by phosphodiester linkages or modified linkages such as phosphotriester, phosphoramidate, siloxane, carbonate, carboxymethyl ester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages.

A nucleic acid "encodes" an RNA or protein product if the RNA or protein product is formed by transcription or by both transcription and translation, respectively, of the nucleic acid or of a reverse transcript of the nucleic acid when the nucleic acid is RNA.

A nucleic acid "expression construct" is a nucleic acid which encodes an RNA or protein product which is formed upon transcription or upon transcription and translation of the nucleic acid. RNA expression constructs which can be directly translated to generate a protein product, or which may be reverse transcribed and either transcribed or transcribed and translated to generate an RNA or protein product, respectively, are also included within this definition.

"Naked" DNA refers to a nucleic acid vector, generally DNA, but alternatively comprising another nucleic acid, which is delivered to a cell in a suspension that does not comprise a matrix, a virus vector, or a similar structure which contains the nucleic acid. Naked DNA vectors encompass nucleic acid vectors which comprise agents (e.g. condensing agents or amphipathic carriers), in addition to the nucleic acid, which promote uptake of the nucleic acid by cells.

By describing two polynucleotides as "operably linked" with one another is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked with the coding region of a gene is able to promote transcription of the coding region.

As used herein, the term "promoter/regulatory sequence" means a nucleic acid sequence which is required for expression of a gene product operably linked with the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is one which catalyzes initiation of DNA transcription at approximately the same level, regardless of the tissue type of the cell within which it is contained.

A "tissue-specific" promoter is one which catalyzes initiation of DNA transcription at different rates in different tissue types. Generally, an 'X tissue-specific' promoter initiation of DNA transcription at a greater rate in cells of tissue type X than in cells of a different tissue type.

A "physiologically responsive" promoter is one which catalyzes initiation of DNA transcription at different rates, depending on the presence, absence, or degree of a physiological state, such as the presence of a particular chemical compound or a particular histological structure.

A "pharmacological agent-specific enhancer" is a nucleic acid element which, when present in an expression construct, increases expression from the expression construct in the presence of the pharmacological agent, relative to expression from the expression construct in the absence of the pharmacological agent.

A "ribozyme" is an RNA molecule, or a molecule comprising an RNA molecule and a polypeptide molecule, which is capable of specifically catalyzing a chemical reaction, in a manner analogous to enzymatic catalysis.

As used herein, a "virus vector" is a nucleic acid-containing composition which comprises a protein which naturally occurs in a virus, wherein the composition is capable of transferring its nucleic acid into the interior of at least one type of cell when the virus vector is contacted with the cell. A "gene therapy vector" is a composition of matter which comprises an expression construct and which can be used to deliver the expression construct to the interior of a cell.

A "therapeutic gene product" is a protein or RNA molecule which, when provided to or expressed in a diseased or wounded tissue, alleviates, prevents, or inhibits the disease, promotes healing of the wound, or prevents worsening of the wound.

An "antisense oligonucleotide" is a nucleic acid molecule (e.g. DNA, RNA, or a polymer comprising one or more nucleotide analogs), at least a portion of which is complementary to a nucleic acid which is present in a cell. The antisense oligonucleotides of the invention preferably comprise between about twelve and about fifty nucleotides. More preferably, the antisense oligonucleotides comprise between about fourteen and about thirty nucleotides. Most preferably, the antisense oligonucleotides comprise between about sixteen and about twenty-one nucleotides. The antisense oligonucleotides of the invention include, but are not limited to, phosphorothioate oligonucleotides and other modifications of oligonucleotides, as described herein. Methods for synthesizing oligonucleotides, phosphorothioate oligonucleotides, and otherwise modified oligonucleotides are well known in the art (U.S. Pat. No: 5,034,506; Nielsen et al., 1991, Science 254: 1497), and each of these types of modified oligonucleotides in included within the scope of the invention.

As used herein, an "apoptosis-inducing protein" means a protein which, when expressed in a cell, causes the cell to begin, accelerate, or continue the process of programmed cell death, which is characterized by the fragmentation of the cell into membrane-bound particles that are subsequently eliminated by the process of phagocytosis.

"Local" or "localized" delivery of an agent to a cell or to a tissue of an animal refers to delivery of the agent using a method that does not deliver the agent systemically to the animal, and which preferably does not deliver any significant proportion of the agent to cells or tissue other than that to which delivery is intended. Numerous compositions and methods are known to be effective for local delivery, as described herein.

An agent is delivered to a cell or tissue "in a sustained-release manner" if the agent is administered to the cell or tissue in a formulation wherein the cell or tissue is contacted with the agent for a longer period than it would be if the agent were administered without the formulation. For example, a sustained release preparation for delivering a nucleic acid releases the nucleic acid from the preparation over time, and protects not-yet-released nucleic acid from degradation (e.g. nuclease-catalyzed degradation).

"Diseases and disorders," as used herein refer to any pathological or other undesirable and abnormal physiological condition of a cell, regardless of whether the condition is formally recognized as a 'disease.'

Cells or tissue are "affected" by a disease or disorder if the cells or tissue have an altered phenotype relative to the same cells or tissue in a subject not afflicted with a disease or disorder.

An "abnormal" animal tissue is one which, when obtained from an animal afflicted with a disease or disorder, has a phenotype which is different from the phenotype of same tissue in an animal of the same type which is not afflicted with the disease or disorder.

A "defective" protein is a protein which has an altered amino acid sequence, relative to the wild type protein, and which does not exhibit the same type or degree of activity or other property that the wild type protein exhibits.

As used herein, "alleviating" a disease or disorder means reducing the frequency or severity with which a symptom of the disease or disorder is experienced by a patient.

A "re-entry circuit" is a conduction pathway in heart tissue that does not follow the normal impulse progression route, but instead re-enters partially re-polarized tissue in a sustained abnormal cycle that results in rapid, uncontrollable heart rhythms.

The "interior portion" of a matrix is a portion of the matrix which does not contact a solvent in which the matrix is suspended or in which a device or particle coated with the matrix is suspended or immersed, at least until the matrix has at least partially biodegraded. It is understood that, in instances in which multiple layers of matrix are present, the "interior portion(s)" of the matrix can refer only to the innermost portion of the innermost layer of the matrix (i.e. the first-deposited layer) or to the inner portion of each layer of the matrix, with respect to the first-deposited layer. The interior portion of the matrix does not include the exterior surface of the matrix, but may include any and all parts of the matrix that are not exposed on the exterior surface.

A material is "biocompatible" with respect to an animal if the presence of the material in the animal is not injurious to the animal. By way of example, a biocompatible material does not induce an immune response to the material when the material is implanted in the body of an animal.

A material is "biodegradable" if the material undergoes decomposition when contacted with a biological system such upon implantation into an animal. The decomposition may be evidenced, for example, by dissolution, depolymerization, disintegration, or by another chemical or physical change whereby the bulk of the material in the biological system is reduced over time. Such decomposition may be, but is not necessarily, catalyzed by a component of the biological system (e.g. an enzyme).

A material is "in fluid communication" with a cell or tissue if the material is in contact with a fluid which normally contacts the cell or tissue, either in vitro or in vivo. Examples of materials in fluid communication with a cell or tissue include a material deposited, suspended, or dissolved in a tissue culture medium in which the cell or tissue is maintained, a material deposited, suspended, or dissolved in a body fluid which normally contacts the cell or tissue in an animal, and a material which physically contacts the cell or tissue.

As used herein, the term "condensing agent" and grammatical forms thereof generally refers to molecules such as polycationic polymers and elemental cations that, because of their size or for some other reason, are able to condense nucleic acids. A non-limiting list of polycationic condensing agents which are suitable for condensing nucleic acids such as DNA may be found in Lasic (1997, In: *Gene Delivery*, Lipsows, Ed., CRC Press, Boca Raton, Fla., pp. 33-37 and 56-61).

A nucleic acid is "condensed" if, when combined with a condensing agent, the nucleic acid exhibits reduced nuclease susceptibility, decreased hydrodynamic diameter, a more geometrically compact conformation, or reduced susceptibility to oxidation. Condensation of nucleic acids has been described in the prior art (e.g. using polylysine) and is well known.

A "particle" or "particulate formulation" means an object, or plurality of such objects, having geometric dimensions compatible with injection, cellular ingestion, or mucous membrane penetration. Thus, such a particulate formulation typically comprises, or preferably consists essentially of, spherical or ellipsoid particles having a maximal geometric dimension of about 50 microns, preferably less than about one micron, and more preferably, from about 100 nanometers to 500 nanometers.

A "bulk material" or "bulk formulation" means a monolithic object, having geometric dimensions in excess of those compatible with injection, cellular ingestion, or mucous membrane penetration. Such bulk formulations typically have one or more geometric dimensions in excess of 50 microns in diameter. Bulk materials may, for example, be provided in the form of spheres, irregular shapes, sheets, needles, bars, and the like.

The "hydrodynamic diameter" of an object such as a molecule or a particle refers to the diameter of an imaginary sphere which is traced by rotating the object in all directions around its center of mass. The hydrodyanamic diameter can be thought of roughly as the 'effective size' of an object rotating rapidly in space or in solution. By way of example, the hydrodyanamic diameter of a sphere is the actual diameter of the sphere, and the hydrodynamic diameter of a rigid rod-shaped object is the length of the object along its longest axis (i.e. the length of the rod). For rigid objects, the hydrodynamic diameter is equal to the largest geometric dimension of the object, measured along a straight line.

An "implantable device" means a particle or other object which can be entirely or partially inserted into the body of an animal. Implantable devices thus include particles which, when applied topically to a surface of the animal body, are capable of being taken up by a tissue or cell of the animal. The means by which the particle or other object is inserted into the animal body is not critical, and includes, for example, swallowing, inhalation, injection, topical application, physical penetration, insertion into an incision made in the animal body, and the like.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLE 1

Ibutilide Controlled Release Matrices for Preventing

Re-Entrant Atrial Flutter in Dogs

In the experiments described in this Example, the Y-atriotomy model for re-entrant flutter in dogs, as described (Labhasetwar et al., 1998, J. Cardiovasc. Pharmacol.

31:449-455) was used to demonstrate the efficacy of sustained release of ibutilide from a right atrial epicardial implant for alleviating re-entrant atrial flutter.

Figure 1:
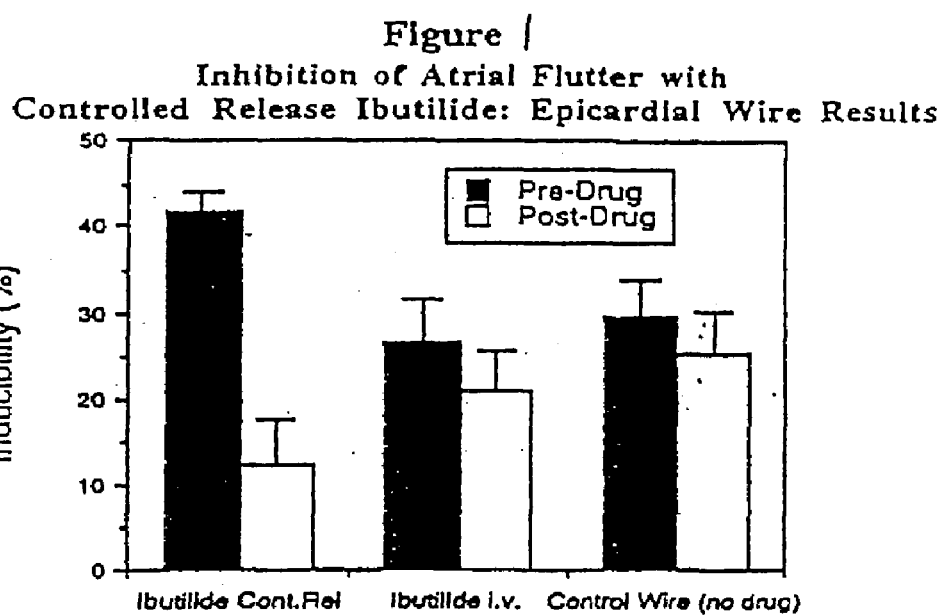
FIG. 1 is a bar graph which indicates inducibility of atrial flutter in dogs implanted with epicardial pacing electrodes, as described herein.

Ibutilide sustained release matrices were made using a multi-layer polyurethane solvent evaporation technique to coat an epicardial pacing electrode. Inducibility of atrial flutter upon burst atrial pacing was investigated in dogs which had a coated electrode implanted therein, compared with dogs which had a non-coated electrode implanted therein. As indicated in FIG. 1, inducibility of atrial flutter was significantly reduced in dogs which had a coated electrode implanted therein ("Ibutilide Cont. Rel" in FIG. 1). The rate of release of ibutilide from the electrode in these dogs was approximately 2.4 micrograms per hour per millimeter of electrode length. No significant inhibition of inducibility of atrial flutter was observed in dogs which had non-coated electrodes implanted therein or in dogs which were systemically administered a dose of ibutilide equivalent to that provided by the polymer. Electrophysiologic studies demonstrated that atrial ibutilide delivery did not significantly affect ventricular electrophysiologic parameters.

The results of the studies described in this Example demonstrated the site-specific therapy directed at the right atrial myocardium can be effective to suppress re-entrant atrial flutter.

EXAMPLE 2

HERG Gene Therapy of Re-Entrant Atrial Flutter in a Dog Model

The experiments described in this Example demonstrate that DNA-containing biodegradable polymeric microparticles and nanoparticles are useful for delivery of nucleic acid vectors to animal cells.

A reverse gene therapy method is used to locally deliver a nucleic acid vector comprising a defective HERG protein to the right atrium of dogs in order to effect site specific overexpression of HERG (A561V) at that site.

The nucleic acid vector is delivered in the form of a plasmid suspended in nanoparticles of a polylactic-polyglycolic acid (PLGA) copolymer having poly-L-lysine (PLL) incorporated therein. The plasmid DNA is in a condensed form. Prior to using the nucleic acid vector encoding defective HERG, a reporter vector comprising a nucleic acid encoding a bacterial β-galactosidase or a luciferase operably linked with a CMV promoter is used to assess the level and localization of expression effected by PLGA/PLL nanoparticle delivery of the vector. Nucleic acid vector bioavailability distribution to distal sites is assessed using PCR. The dog model of cardiac arrhythmia is based upon re-entrant atrial flutter which is induced after a Y-atriotomy incision, as described (Frame, 1996, Cardiol. Clin. 14:471-481).

Formation of DNA-PLGA Particles

The plasmid described in this Example was formulated for sustained release by suspending it a biodegradable polymer microparticle that could be injected into a specific tissue site in the canine atrial myocardium.

The microparticles were formed using an oil-in-water emulsion of a PLGA copolymer. Sonication of the emulsion (e.g. to control particle size) was avoided to minimize damage to the plasmid. Instead, a "salting-out" technique was used to control the particle size. PLGA (3 milligrams per milliliter) was suspended in chloroform, and a small volume (ca. 100 microliters) of an aqueous plasmid DNA suspension (comprising about 10 milligrams per milliliter DNA) was added to this, while vortexing the mixture at 30,000 rotations per minute at 0° C. for one minute, to generate an initial emulsion.

The initial emulsion was combined with an aqueous solution comprising either no or 1 molar $CaCl_2$ and (0.1-0.5% v/v) polyvinyl alcohol (PVA) as an emulsifier. This mixture was vortexed at 0C for one minute to generate a second emulsion. The mixture was ultracentrifuged to separate microparticles, and the microparticles were repeatedly resuspended and ultracentrifuged to remove non-incorporated plasmid. Particle size analysis was performed using a laser light scattering apparatus (NICOMP; Brookhaven Labs, New York, N.Y.), and particle morphology was assessed by scanning electron microscopy. Plasmid-containing microparticles having an average diameter of about 2.7 micrometers were made when 1 molar $CaCl_2$ was included in the PVA-containing phase; microparticles having an average diameter of about 4.0 micrometers were made when the PVA-containing phase did not contain $CaCl_2$.

Figure 2:
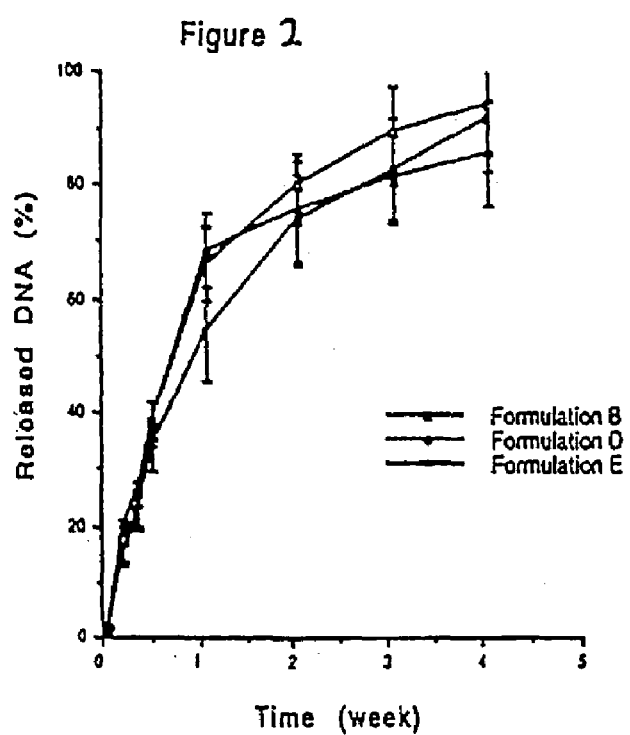
FIG. 2 is a graph which indicates the proportion of DNA released from PLGA copolymer microparticles, as described herein.

The rate of release of DNA from the microparticles was investigated by incubating the particles in vitro in a solution comprising 0.1 molar Tris buffer at pH 7.4, 0.01 molar EDTA, and these data demonstrated that the DNA entrapped within the microparticles was made available with an initial burst phase of release, followed by an exponentially declining release rate. Nearly complete release of DNA from the microparticles was effected by 30 days incubation, as indicated in FIG. 2. In FIG. 2, formulation B comprised microparticles initially consisting of about 2% (w/w) plasmid, formulation D comprised microparticles initially consisting of 5% (w/w) plasmid, and formulation E comprised microparticles initially consisting of 11% (w/w) plasmid. No evidence of plasmid DNA fragmentation was detected by agarose gel electrophoresis of DNA released from the microparticles.

Transformation studies using a plasmid encoding a luciferase protein were performed by contacting type 293 cells with the plasmid. The plasmid was incorporated into DNA-microparticles as described herein, using $CaCl_2$. As indicated in FIG. 3, the $CaCl_2$ microparticle synthesis protocol resulted in significantly enhanced transfection, and a dose-response relationship was evident, with respect to the amount of DNA loaded into the microparticles.

Formation of DNA-PLGA Particles

The plasmid described in this Example was formulated for sustained release by suspending it a biodegradable polymer nanoparticle that could be injected into a specific tissue site in the canine atrial myocardium.

In these experiments nanoparticles having sub-micrometer diameters were made, the nanoparticles comprising PLGA and PLL. Nanoparticle formulations procedures were identical to those described above for preparation of microparticles, with the following changes. PLL having a molecular weight of 4000 was added to the PVA-containing phase at a concentration of 0.5 milligrams per 500 milligrams PVA in 10 millimolar Tris buffer adjusted to pH 7.4 using HCl and containing 10 micromolar EDTA. The second emulsion was ultracentrifuged, rinsed, and freeze-dried.

Analysis of the nanoparticles made by this method revealed that nanoparticles comprising 3% DNA, by weight, had an mean diameter of about 500 nanometers, and that more than 86% the DNA used to make the particles was incorporated into the nanoparticles. Other characterization procedures indicated that PLL condensed the plasmid DNA in the microparticles. For example, studies of DNA release from nanoparticles in the Tris-EDTA buffer indicated very slow DNA elution, as indicated in FIGS. 4A an 4B. However, if the 0.1% (w/v) sodium dodecyl sulfate was included in the Tris-EDTA buffer, the rate of DNA release from the nanoparticles was increased significantly. Further by way of example, incubation of the nanoparticles in an organic solvent (CHCl$_3$) followed by aqueous recovery of the DNA indicated that only after incubating the nanoparticles with SDS or trypsin could released DNA be detected. These observations also indicate that the plasmid was suspended in or on the nanoparticles in the form of a DNA-PLL condensate. Comparisons with CaCl$_2$-DNA microparticles prepared as described herein and DNA-PLL-PLGA nanoparticles are indicated in Tables I and II.

TABLE I

A comparison of the physical characteristics of DNA-CaCl$_2$ microparticle and DNA-PLL-PLGA nanoparticle

| Preparation | DNA capture Efficiency[a] | Mean Particle Size | 48 hr DNA release (in TE buffer) | 48 hr DNA release (in TE Buffer + 0.1% SDS) |
|---|---|---|---|---|
| PLGA-CaCl$_2$ Microparticles | 43.3% | 2.7 μm | 20% | NM[b] |
| PLGA-PLL Microparticles | 86.3% | 476 nm | 1.7% | 44% |

Notes:
[a]DNA capture efficiency means the percentage (by weight) of the DNA used to make the particles which was incorporated into the particles.
[b]NM means not measured.

TABLE II

Size distribution and surface charge (zeta potential) of DNA-PLL-PLGA nanoparticles (pHOOK-LacZ DNA was used)

| Formulation | Particle size | zeta potential |
|---|---|---|
| PLGA | 496.5 ± 6.1 nm | −32.13 ± 1.47 mV |
| DNA/PLGA | 522.5 ± 4.7 nm | −35.01 ± 2.47 mV |
| PLGA-PLL | 510.6 ± 7.4 nm | −27.99 ± 0.70 mV |
| DNA-PLL-PLGA | 507.5 ± 8.9 nm | −38.45 ± 1.27 mV |

As is evident from Table II, incorporation of PLL into PLGA nanoparticles resulted in a more positively charged nanoparticle. However, the charge of the DNA-PLL-PLGA was significantly more negative than the charge of the PLL-PLGA particle, indicating that the DNA neutralized the charge of PLL.

PLL-containing PLGA nanoparticles comprising a plasmid which encoded luciferase were used to transform type 293 cells. As indicated in FIG. 4C, significant enhancement of transformation after 48 hours incubation of the cells with the PLL-PLGA-DNA nanoparticle, relative to the transformation achieved using cells incubated for 48 hours with PLGA nanoparticles which did not comprise DNA.

Figure 5:
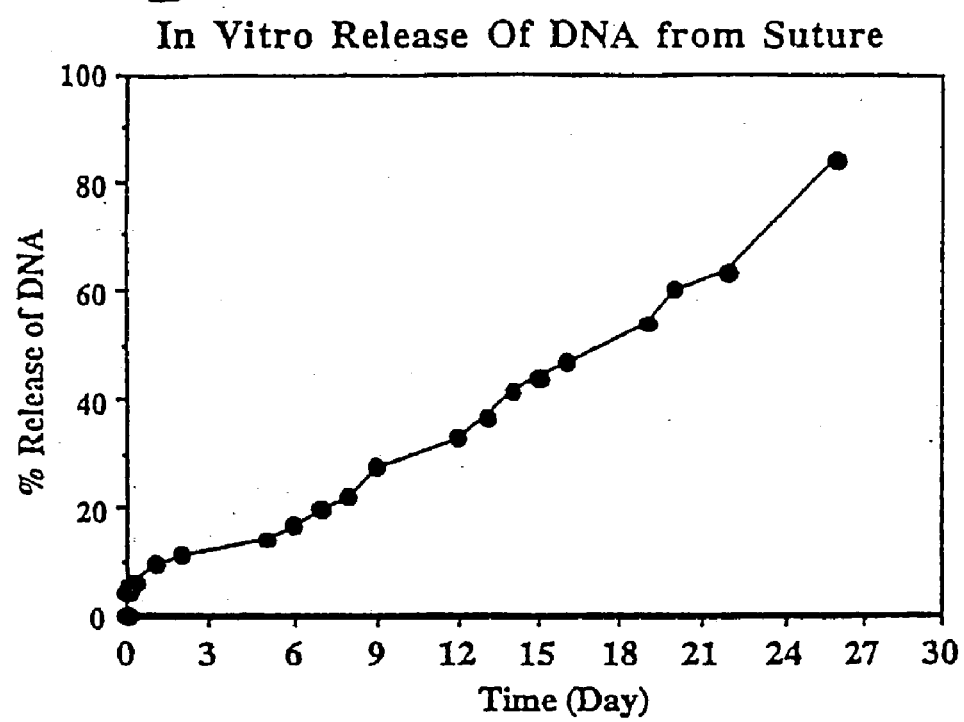
FIG. 5 is a graph which indicates in vitro release of DNA from a suture coated with a DNA-PLGA emulsion, as described herein.

DNA-PLGA Sustained Release Coatings: Suture-Based Gene Delivery and Atrial Myocardial Results Chromic sutures were coated with a DNA-PLGA emulsion, which was prepared as described herein. This coated suture was used to repair subcutaneous wounds made in rats. In vitro release kinetics of DNA from a suture coated with a DNA-PLGA polymer containing 0.5% (w/w) DNA are indicated in FIG. 5. These data indicate that, following a brief burst phase, the rate of release of DNA from the suture is nearly constant.

Figure 6:
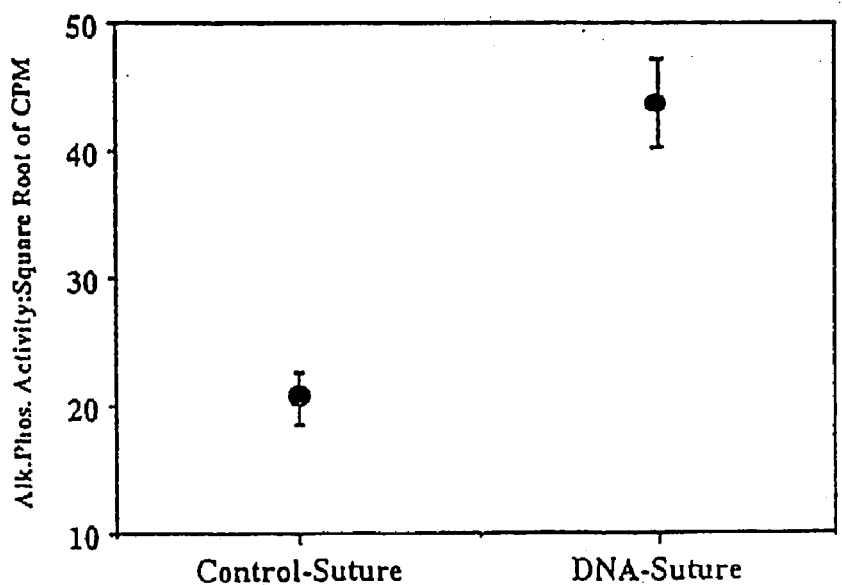
FIG. 6 is a graph which indicates alkaline phosphatase activity detected in wounded tissue obtained from wound sites closed using either a DNA-PLGA-coated suture or a non-coated (control) suture.

A chromic suture was coated with a PLGA-DNA polymer using the emulsion technique described herein. The DNA was a plasmid comprising an expression construct encoding human alkaline phosphatase. Transformation of skeletal muscle cells was demonstrated by using this coated suture to close subcutaneous skeletal muscle wound sites in rats. The amount of suture used per wound site contained approximately 250 micrograms of plasmid DNA. Tissue recovered from wound sites was assayed using well known methods to determine expression of alkaline phosphatase at the site. As indicated in FIG. 6, significantly greater alkaline phosphatase activity was detected at wound sites closed using the DNA-PLGA coated suture than at wound sites closed using a suture which did not contain DNA.

Figure 7:
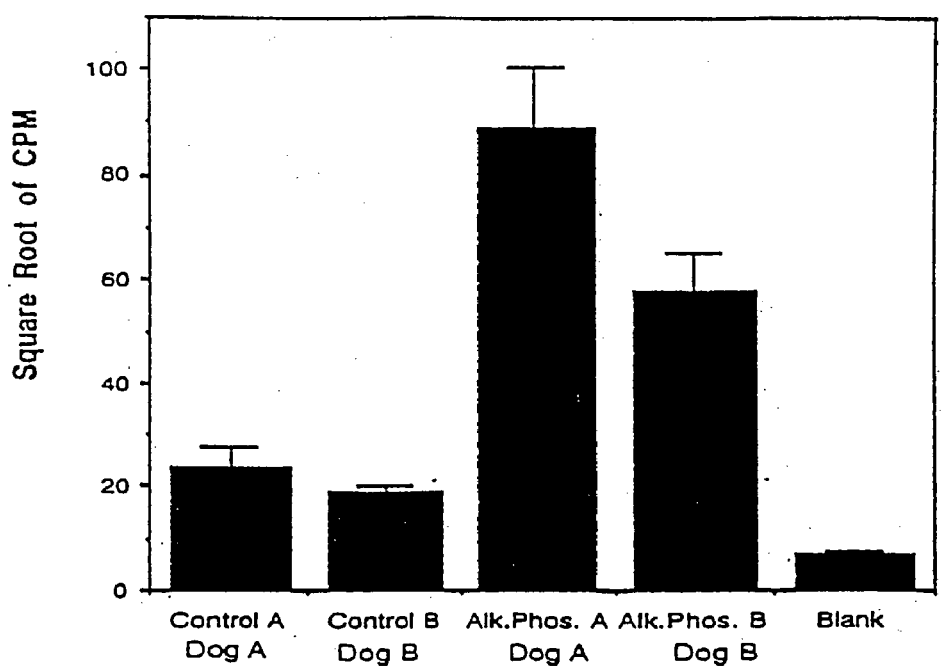
FIG. 7 is a bar graph which indicates alkaline phosphatase activity detected in atrial tissue obtained from dogs in which an atriotomy incision was made and repaired using either a DNA-PLGA-coated suture or a non-coated (control) suture. Individual dogs are designated 'A' and 'B' for each suture type. "Blank" indicates myocardial tissue not injected with DNA.

This DNA-PLGA coated suture was then used in a series of atriotomy studies to determine if the coating could be used to transform cells of the atrial myocardium. In two-dog studies, a one-centimeter atriotomy incision was made in the right atrial appendage of each of four dogs. The atriotomy incision was repaired either with the PLGA-DNA coated chromic suture or with a chromic suture which did not comprise DNA. Atrial tissue was recovered from the dogs following euthanasia. As indicated in FIG. 7, significantly greater alkaline phosphatase activity was detected in atrial tissue closed using the DNA-PLGA coated suture than in atrial tissue closed using a suture which did not contain DNA.

EXAMPLE 3

Gene Therapy Using a Cardiac Myocyte Model

The Experiments described in this Example may be used to demonstrate that a nucleic acid vector comprising an expression vector encoding the HERG (A561V) protein may be delivered to atrial myocardium cells in order to alleviate re-entrant atrial flutter.

CHO Cell Transformation Studies

Transformation of Chinese Hamster Ovary (CHO) cells in vitro is used to investigate the mechanism(s) by which the cells are transformed using DNA-PLGA-PLL nanoparticles. Transformation of CHO cells is also used to investigate the effects of nanoparticle formulation parameters (e.g. the effect of including or omitting PLL from the particles) on the steps involved in nanoparticle uptake, endosomal or lysosomal transit of the nanoparticles within the cells, and nuclear expression of vector DNA. Properties of transformed CHO cells which are assessed include, but are not limited to, histological or immunological examination of the location of vector DNA expression, enzyme activity of an enzyme encoded by the vector DNA, and assessment cell death or growth inhibition mediated by PLL or PLGA.

CHO cells are selected for several reasons. Other investigators have demonstrated successful transfection of these cells using vectors comprising mutant genes responsible for the Long QT Syndrome and CHO cells in culture (Sanguinetti et al., 1996, Proc. Natl. Acad. Sci. USA. 93:2208-2212; Sanguinetti et al., 1996, Nature 384:80-83; Sanguinetti et al., 1995, Cell 81:299-307). CHO transfection experiments are performed using DNA vectors which comprise a CMV promoter operably linked with a nucleic acid encoding the HERG (A561V) protein.

Cardiac Myocyte Transformation Studies

Primary cardiac myocytes transformation is performed using either of two candidate promoters having specificity for cardiac tissue. Transformation efficiency using a DNA vector comprising a CMV promoter, the a-myosin heavy chain (α-MyHC) promoter (Robbins, 1997, Trends Cardiovasc. Med. 7:185-191; Milano et al., 1994, Proc. Natl. Acad. Sci. USA 91: 10109-10113), or the atrial natriuretic factor (ANF) promoter (Field, Science 239:1029-1033), is determined using rat primary cardiac myocytes in culture. These latter two promoters may be inserted into the vector DNA using a recombinant methodology, as described (Robbins, 1997, Trends Cardiovasc. Med. 7:185-191; Milano et al., 1994, Proc. Natl. Acad. Sci. USA 91: 10109-10113; Field, Science 239:1029-1033). The vector DNA may further comprise a reporter nucleic acid (e.g. a cDNA encoding luciferase) or a pathological nucleic acid (e.g. a nucleic acid encoding HERG (A561V) protein).

Plasmid DNA Transfection Assays

CHO cells are used as a model cell culture system to evaluate the degree of episomal transformation, gene expression, and enzyme activity of a β-galactosidase expression construct following delivery of DNA-PLL-PLGA nanoparticles to the cells. Upon completion of these initial studies, primary rat neonatal cardiac myocyte cells in culture are used to study the efficacy of transformation of those cells using a HERG (A561V) protein expression construct in a DNA-PLL-PLGA nanoparticle.

Cell cultures in Dulbecco's Modified Eagle Medium containing 1% (v/v) fetal bovine serum and 1% (w/v) penicillin or streptomycin are approximately 25% confluent for all transfection experiments. The cell culture media are removed and replaced with fresh media containing DNA-PLL-PLGA nanoparticles dispersed therein. The nanoparticle equivalent of 10, 20, 50, or 100 micrograms of DNA is added to each culture plate in order to determine the operable range of DNA dose for the cell culture system. For comparison, a standard calcium phosphate-mediated DNA transformation is performed as a positive control. At the conclusion of each 48 hour study, transformed cells are either prepared for immunohistochemistry or cytochemistry or scraped off the culture dish for enzymatic assay of gene expression.

Transformed cells harvested from cultures are fixed for 10 minutes using a 0.5% (v/v) glutaraldehyde solution in phosphate buffered saline. The cells are rinsed and incubated for 10 minutes at room temperature (i.e. about 20° C.) with a 1 millimolar $MgCl_2$ solution in pH 7.4 phosphate buffered saline. The cells are then stained for 5 hours using an X-gal staining solution, comprising 1 milligram of X-gal per milliliter, 5 millimolar $K_3Fe(CN)_6$, 5 millimolar $K_4Fe(CN)_6$, and 1 millimolar $MgCl_2$ in pH 7.4 phosphate buffered saline. Samples are embedded in paraffin and prepared for light microscopy after post-fixation treatment with a phosphate buffered solution comprising 4% (v/v) paraformaldehyde and 0.5% (v/v) glutaraldehyde.

β-galactosidase activity in cell lysate is detected using a Galacto-Light Plus" chemiluminescent reporter system, as described (Jain et al., 1991, Anal. Biochem. 199:119-124). The amount of β-galactosidase activity in the sample is determined using a luminometer, and enzyme activity is normalized to account for protein content.

Immunohistochemistry is performed to localize protein expression in tissue or cells. Because reporter assays frequently underestimate the extent of transfection (Couffinhal et al., 1997, Hum. Gene Ther. 8: 929-934), immune techniques are also used to assess the degree of transfection. Fixation is performed using 10% (v/v) neutral buffered formalin, followed by either cryostat or paraffin sectioning. Sections mounted on slides are treated first with ammonium chloride or sodium borohydride to quench extraneous aldehyde groups, or with hydrogen peroxide to block endogenous peroxidase activity, and then with 2% (w/v) gelatin in phosphate buffered saline to block non-specific protein binding. The primary antibody of interest (which binds specifically with either β-galactosidase or with FLAG (see below)) is applied, followed by an appropriate secondary antibody (i.e. which binds specifically with the primary antibody) conjugated to a marker such as a fluorescent label (e.g. fluorescein or rhodamine) or an enzyme (e.g. horseradish peroxidase). Microscopic slides are then assessed for the immune distribution of the protein of interest, and the results are compared with the reporter-specific histochemistry and the level of secreted enzyme activity.

Myocyte Protocols

Primary neonatal cardiac myocyte cultures are used to assess model myocardial formulation parameters and expression conditions for a nucleic acid vector of interest. An established methodology is used to create primary cultures of rat neonatal ventricular myocytes (Parker et al., 1990, J. Clin. Invest. 85:507-514; Thaik et al., 1995, J. Clin. Invest. 96:1093-1099). Sprague-Dawley rats are used at two days of age. Hearts are freshly harvested and cultured as described (Parker et al., 1990, J. Clin. Invest. 85:507-514; Thaik et al., 1995, J. Clin. Invest. 96:1093-1099). Typically after overnight incubation in medium containing 5% (v/v) horse serum, the medium is replaced by serum-free medium. Transfection studies are then performed as described (Parker et al., 1990, J. Clin. Invest. 85:507-514; Thaik et al., 1995, J. Clin. Invest. 96:1093-1099), using methodology comparable to that used for CHO cells, as described herein.

In order to determine any cytotoxic effects that the PLGA or polylysine formulation may have, or to detect another unexpected toxicity, representative cell culture plates are assessed by microscopy to determine the extent of necrotic cell death, as described (Subramanian et al., 1995, Cell Growth Differ. 6: 131-137) and apoptosis. Apoptosis is determined using the terminal transferase-mediated dUTP-biotin nick end-labeling (TUNEL) assay, as described (Kirshenbaum et al., 1996, Dev. Biol. 179:402-411). Initial studies are performed using myocytes involve nanoparticles comprising reporter DNA, and repeat the studies performed using CHO cells, in order to document any difference(s) between the two cell lines.

Once comparable data have been generated, the myocytes are used to study a nucleic acid vector comprising an expression construct encoding the candidate therapeutic gene, HERG (A561V). Because no antibody is available that will distinguish the wild type HERG protein from the HERG (A561V) protein, an epitope (FLAG) tag is incorporated at the amino terminal end of the HERG (A561 V) expression construct. HERG (A561V) expression is monitored by monitoring the presence of the octapeptide FLAG" (Eastman Kodak) sequence, as described (Chubet et al., 1996, Biotechniques 20:136-141; Shelness et al., 1994, J. Biol. Chem. 269:9310-9318).

Therapeutic Gene Studies Using a Reverse Gene Therapy Vector

A nucleic acid (e.g. a cDNA) encoding the mutant $K^+$ channel gene HERG (A561V) is operably linked with the CMV promoter, the α-MyHC promoter, or the ANF promoter to form a HERG (A561V) expression construct. Other potentially cardiac-specific promoters have been described and may optionally be used in the nucleic acid vector described herein. These promoters include cardiac α-actin (Biben et al., 1996, Develop. Biol. 173:200-212) and MCLC2v (Hunter et al., 1995, J. Biol. Chem. 270:173-178).

The HERG (A561V) expression construct is incorporated into the pSP64 transcription vector using standard methods. The HERG (A561V) expression construct is also inserted into a pFLAGCMV2 plasmid (Eastman-Kodak), as described (Chubet et al., 1996, Biotechniques 20:136-141; Shelness et al., 1994, J. Biol. Chem. 269:9310-9318). The pFLAGCMV2 plasmid comprises the FLAG sequence, a polylinker region for recombination, and the CMV promoter. Following fusion of the FLAG" coding sequence and the HERG (A561V) coding sequence, the recombinant protein expressed is tagged with the FLAG" octapeptide sequence to form a fusion protein.

The FLAG" octapeptide sequence on the HERG(A561V)-(FLAG" octapeptide) fusion protein can be detected using known immunohistochemical methods (Chubet et al., 1996, Biotechniques 20:136-141; Shelness et al., 1994, J. Biol. Chem. 269:9310-931) which involve use of an Anti-FLAG" Monoclonal Antibody (M5). Thus, the presence of FLAG" octapeptide indicates expression of HERG (A561V) protein, and this immunohistochemical assay may be used to localize the HERG (A561V)-FLAG fusion protein in order to determine transformation efficiency, membrane localization, and tissue distribution of the fusion protein.

Animal Model Experiments

Experiments are performed using dogs as a model of re-entrant atrial flutter in order to determine an optimal method of delivery of nanoparticles to atrial myocardium. The spatial distribution of the nanoparticles within the atrial myocardium and distal cardiac structures is assessed following delivery, using fluorescently-labeled particles. Myocardium and other cardiac tissues transformed using a nucleic acid vector comprising either a reporter construct or the FLAG-HERG conjugate is examined using specific reporter assays or immunolocalization assays in order to determine the distribution and extent of transformation effected using a given vector. Both sectioned samples and tissue planes cut enface are used to perform these assays, using established techniques (e.g. Mondy et al., 1997, Circ. Res. 81:320-327). The effect of delivery of nanoparticles comprising an expression construct encoding the HERG (A561V) protein upon induction of atrial flutter and related ventricular and atrial electrophysiologic parameters is assessed.

Short Term (72 Hour) Dog Experiments

The goals of these acute dog studies are to investigate DNA-containing nanoparticle delivery techniques and early events involved in the mechanisms of the distribution of nanoparticle-mediated transfection in the canine myocardium. These 72 hour studies are used to determine optimal nucleic acid vector delivery conditions, the acute distribution of nanoparticles in the re-entry circuit, and the extent of any acute cardiac or systemic spread of the nucleic acid vector. These studies are also used to determine whether local delivery of DNA-containing nanoparticles affects inducibility of atrial flutter or other electrophysiologic parameters. Using the Frame Y-incision model, a DNA-containing nanoparticle suspension is injected using a 27 gauge needle into the atrial myocardium of each dog, just below the subtransverse incision site. This juncture of the reentry loop is critical, and conduction block in this region should limit or prevent inducibility of atrial flutter.

Non-recovery studies initially involve use of fluorescently labeled nanoparticles 500 nanometers in diameter Ultrabrite" (Polysciences, Warrington, Pa.). Histology studies are performed to determine the distribution of fluorescently labeled nanoparticles at the site of administration and adjacent myocardial regions. Once ideal nanoparticle concentration and delivery conditions have been established, a series of 72 hour studies are performed using nanoparticles comprising a reporter construct in order to determine expression of the reporter construct in the atrial myocardium, expression at remote cardiac sites, and acute bioavailability in the atrial myocardium using PCR analyses with appropriate primers. Local and distal myocardium, liver, lung, kidney, and gonads are sampled for these assays.

Chronic Dog Studies

The goals of these chronic dog studies are to examine expression and effects on atrial flutter effected by administration of nanoparticle formulations that are judged to be optimal in cell culture studies and acute dog studies. Initial experiments focus on reporter studies to determine the extent of expression, examining both the percentage of nuclei in the region of interest which express the β-galactosidase reporter protein. The initial experiments also indicate the effect(s) of nanoparticle delivery on preventing atrial flutter and related electrophysiologic parameters. Effects of nanoparticle delivery on distal cardiac sites, as well as distal organs, are examined both for reporter protein expression and for the presence of nucleic acid vector, as determined by PCR.

Transformation of atrial myocardium using nanoparticles comprising an expression construct encoding HERG (A561V) protein operably linked with a CMV promoter or a cardiac tissue specific promoter is though to cause conduction block and thereby inhibit atrial flutter. This is confirmed using the methods described herein. The tricuspid annulus from each chronic dog is explanted at the time of sacrifice (i.e. 4 weeks post-surgery) and examined to determine precise regional differences in cardiac conduction parameters in the reentry circuit, as described (Fei et al., 1997, Circ. Res. 80:242-252). Transformation effected using nucleic acid vector-containing nanoparticles is compared with transformation effected by injection of the nucleic acid vector alone (i.e. not contained in or on a nanoparticle).

Animal Model Procedure: "Y"-Shaped Lesion/Atriotomy Studies

Atrial flutter is induced in dogs using a modification of published procedures (Frame, 1986, Circ. Res. 58:495-511; Buchanan et al., 1993, J. Cardiovasc. Pharmacol. 33:10-14). Male mongrel dogs weighing 25 to 35 kilograms are used in these model studies. General anesthesia using sodium pentobarbital is followed by a right thoracotomy. A "Y"-shaped lesion right atrial incision is at the inferior board of the atrium along the inferior vena cava as described (Frame, 1986, Circ. Res. 58:495-511; Frame et al., 1987, Circulation 5:1155-1175; Boyden et al., 1989, Circulation 79:406-416). The strategy of this approach is to create a permanent conduction block in the right atrium that results in a re-entry loop for atrial impulse conduction for inducing atrial flutter. The "Y"-shaped lesion is closed using 4-0 silk with a continuous interlocking suture, the spacing between each visible suture not to exceed 5 millimeters. Burst pacing episodes can be used to create a reproducible re-entrant circuit involving a pathway around the tricuspid annulus. This model, which induces physiological responses which closely parallel those observed for atrial flutter in humans (Frame, 1996, Cardiol. Clin. 14:471-481), allows atrial flutter to be induced in both an acute and chronic animal study setting. Atrial flutter in this model can also be stopped and reinduced using appropriate pacing protocols as described (Frame et al., 1986, Circ. Res. 58:495-511; Frame et al., 1987, Circulation 5:1155-1175; Boyden et al., 1989, Circulation 79:406-416).

Atrial Flutter Induction

Each experimental atrial flutter induction study comprises eight or more attempts to inducing atrial flutter using burst pacing at 3 milliamp or greater (double capture threshold) for 3 seconds at cycle lengths of 150 milliseconds, 140 milliseconds, 130 milliseconds, 120 milliseconds, 110 milliseconds, and 100 milliseconds. Atrial flutter that continues for five minutes or more is defined as persistent flutter, indicating successful induction. The frequency of inducibility with respect to the number of sustained episodes or attempts to induce atrial flutter before and after placement of a nucleic acid vector delivery system, or a non-DNA-containing implant, is used as a basis for measuring drug effects. Atrial flutter episodes are terminated after five minutes by overdrive pacing as described (Labhasetwar et al., 1994, J. Cardiovasc. Pharm. 24:826-840; Frame et al., 1986, Circ. Res. 58:495-511; Frame et al., 1987, Circulation 5:1155-1175; Boyden et al., 1989, Circulation 79:406-416), or if necessary, by countershock. Animals are allowed at least 5 minutes between induction to be certain of rhythm and blood pressure stability. Animals which are not inducible for sustained flutter are excluded from these studies.

Arrhythmia and Electrophysiologic Endpoints

Animals investigated in this model, both in acute and chronic studies are assessed from the point of view of a number of parameters affecting atrial arrhythmias. These include the following: 1. Atrial flutter induction: the frequency of successful inductions before and after nanoparticle delivery; 2. Atrial impulse conduction, as assessed by multi-electrode studies, as described herein; 3. Electrophysiologic parameters: atrial and ventricular effective refractory periods, sinus node recovery time, atrial flutter cycle length, ventricular rate response, conduction time, and AV-node conduction time.

Epicardial Mapping and Related Electrophysiologic Assessment

Figure 8:
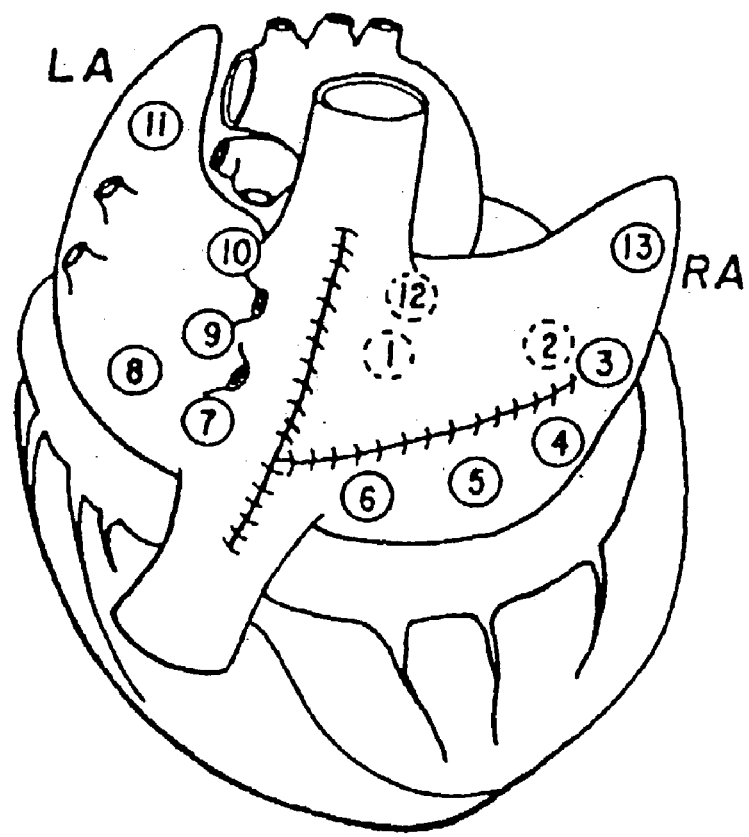
FIG. 8 is a diagram which depicts placement of epicardial electrodes in a dog, as described herein.

The non-recovery procedures and the terminal procedure in chronic dogs characterize the sequence of activation of the reentry loop in the "Y"-shaped lesion model. The technique for epicardial mapping utilizes a published methodology (Frame, 1986, Circ. Res. 58:495-511). FIG. 8 illustrates the placement of epicardial electrodes. Electrodes #1 through #6 in FIG. 8 and a right atrial appendage recording site (Site #13 in FIG. 8) are used. Bipolar platinum epicardial electrodes are used, and are connected with a CODAS analog-to-digital conversion system and computer. The types of measurements of greatest interest are the sequence of activation times for impulse spread beginning from the first electrode site as illustrated in FIG. 8, with respect to changes due to implantation of a controlled release drug delivery system.

The general protocol to be used in these epicardial mapping studies and investigations of the reentry mechanism involves the following. Inducibility is determined, in terms of whether animals develop atrial flutter following the creation of a "Y"-shaped lesion. Next, epicardial electrodes are placed as illustrated in FIG. 8 and described herein. The sequence of epicardial activation is determined and recorded. Epicardial ventricular electrodes are implanted, and the animals are outfitted with a transvenous monophasic action potential electrode catheter. Pacing is carried out with a separate right atrial pacing electrode in acute (non-recovery) studies. Electrophysiological measurements of interest include comparisons made during pacing of the atrial effective refractory period before and after drug system placement, ventricular effective refractory period, changes in cycle length, and atrial flutter cycle length. The monophasic action potential duration in the right atrium, and in the right ventricle is also determined during pacing. All of these measurements, and sequence of activation studies are performed before and after acute drug administration. More extensive atrial mapping may be performed if the electrophysiologic and atrial flutter data indicate this to be necessary or desirable.

All chronic studies, at their termination, involve explantation of the tricuspid ring, and in vitro studies are performed. Typical preparations involve rapidly excising the heart at the time of euthanasia, and dissecting it in cold Tyrode"s solution, equilibrated with 95% oxygen and 5% $CO_2$. The tricuspid ring is dissected and mounted with the endocardium upward in a tissue bath. The tricuspid annulus is instrumented using electrodes, as illustrated in FIG. 9, focusing on the area of nucleic acid vector delivery or control nanoparticle injection. The goal of these studies is to investigate regional differences in conduction attributable to expression of either reporter constructs or expression constructs, such as an expression construct encoding HERG (A561V) protein. Following the end of the electrophysiologic study period, morphology sampling is performed, and the orientation of samples for microscopic investigation is noted with respect to the site of nanoparticle delivery, the site of expression of the nucleic acid vector, the location of electrophysiologic recording regions, and the proximity to the transverse incision and the remainder of the reentry circuit.

Morphologic techniques are used to image reporter expression, both with X-gal staining, and immunohistochemistry to detect β-galactosidase activity. In animals transformed with HERG (A561V), immunohistochemical studies are performed using a commercially available monoclonal antibody to the FLAG" octapeptide fused with HERG (A561V). Routine hematoxylin- and eosin-stained microscopy are performed for morphologic assessment of any cellular response to nanoparticle administration or toxicity related to the polylysine conjugates.

EXAMPLE 4

Incorporation of an Ion Channel Gene Mutation Associated with the

Long QT Syndrome (Q9E-hMiRP1) in a Plasmid Vector for Site Specific

Arrhythmia Gene Therapy

In the present example, we investigated a plasmid vector containing a specific mutation in a human cardiac potassium channel gene that is responsible for one variant of the Long QT syndrome (LQTS), as a construct for site specific gene therapy of re-entrant atrial arrhythmias. LQTS presents as either an inherited or acquired disorder that predisposes to life threatening ventricular arrhythmias. Recent molecular genetic studies have demonstrated that LQTS is caused by mutations in genes that encode cardiac ion channels. Mutations in five ion channels have been linked to various LQTS's: KvLQT1 for LQTS1, HERG for LQTS2, SCN5A for LQT3, MinK for LQTS5 and hMiRP1 for LQTS6 (Leenhardt et al., 2000). Other studies (Abbott et al, 1999) have demonstrated that drug induced LQTS can occur due to genetic mutations in the MinK-related peptide 1 (hMiRP1) subunit of the $I_{Kr}$ (HERG) potassium channels. A patient with a sporadic missense mutation (Q9E-hMiRP1) developed life threatening ventricular arrhythmias following administration of the antibiotic, clarithromycin (Abbott et al, 1999). Patch clamp studies demonstrated Q9E-hMiRP1 channels were 3-fold more sensitive to clarithromycin induced diminution of potassium inward rectifier currents than wild type (Abbott et al, 1999). These clarithromycin-induced electrophysiologic effects closely resemble those associated with Class III anti-arrhythmic agents, that are commonly used to treat either atrial or ventricular arrhythmias. Thus, the present studies sought to investigate whether the site specific delivery of Q9E-hMiRP1 plasmid DNA vectors could be used to for regional atrial myocardial treatment of cardiac arrhythmias, with modulation of electrophysiologic activity via clarithromycin administration, thereby hypothetically disrupting regional re-entrant arrhythmia pathways. The rationale for these studies was also based in part on the hypothetical safety advantage of using a LQTS-based vector in the atrial myocardium, since LQTS does not involve atrial rhythm abnormalities. Thus, over-expressing a gene such as Q9E-hMiRP1 in the atrial myocardium would be unlikely to be pro-arrhythmic for ventricular arrhythmias.

We sought to use plasmid DNA vectors in these investigations rather than viral constructs. However, the efficiency of transgene expression of plasmid vectors is characteristically far less than viral vectors. Thus, these investigations also studied a novel plasmid DNA delivery system using DNA-anti-DNA antibody-cationic lipid (DAC) heteroplexes, that were hypothesized to increase plasmid DNA transfection activity compared to DNA-cationic lipid (DC) complexes or naked DNA, due to the nuclear targeting characteristics of the anti-DNA antibody that was used. Previous investigations (Avrameas et al., 2001) had shown nuclear entry of some, but not all anti-DNA antibodies conjugated with polylysine. These studies demonstrated enhanced transfection due to the anti-DNA antibody-polylysine conjugates in vitro, but not in vivo (Avrameas et al., 1999). In the present example, the following experiments were performed for validating the feasibility of this anti-arrythmia gene therapy approach:

1. The creation and characterization of bicistronic plasmid DNA vectors for overexpressing either wild-type hMiRP1 or the Q9E-hMiRP1 mutation, each with a C-terminus FLAG peptide to facilitate hMiRP1 immunodetection, and also encoding the green fluorescent protein (GFP).

2. Establishment of stable cell lines overexpressing either Q9E-hMiRP1 or hMiRP1 to investigate the membrane localization of the overexpressed ion channel genes, and to study the associated electrophysiologic changes, including clarithromycin responsiveness. We compared HEK293 cells, which do not constitutively express the HERG subunit hMiRP1, to SH-SY5Y cells that normally express this channel protein. We also sought to learn if the multifunctional plasmid vectors used would influence the expected electrophysiologic characteristics of Q9E-hMiRP1.

3. Formulation and mechanistic characterization of DAC heteroplexes for plasmid DNA delivery in vitro and in vivo.

4. Investigation of results from in vivo delivery of both hMiRP1 and Q9E-hMiRP1 plasmids to pig atrial myocardium, using DAC heteroplexes.

The following materials and methods are provided to facilitate the practice of Example 4.

Cell Culture: Human embryonic kidney cells (HEK293) stably expressing HERG (a gift from Dr. Craig T. January; University of Wisconsin, Madison, Wis.) were cultured in minimum essential medium (MEM) supplemented with 10% (v/v) fetal bovine serum (FBS, Hyclone, Logan, Utah) and 1 mg/ml gentamycin (G418, Life Technologies Inc., Gaithersburg, Md.), 1 mM sodium pyruvate, 0.1 mM non-essential amino acids, and (10U/10 µg)/ml penicillin/streptomycin (P/S) solution. Human neuroblastoma SH-SY5Y cells (a gift from Dr. Naohiko Ikegaki; Children's Hospital of Philadelphia, Pa.) were grown in RPMI 1640 medium containing HEPES buffer and L-Glutamine, supplemented with 10% FBS, 1% L-Glutamine, 800 µg/ml G418, P/S solution, and 5 ml OPI. Rat arterial smooth muscle (A10) cell lines were obtained from American Tissue Type Collection (Gaithersburg, Md.) and were cultured in M199 containing 10% (v/v) FBS and P/S solution. Cells were maintained in 5% $CO_2$ at 37° C. All cell culture media and related supplies were purchased from Life Technologies (Gaithersburg, Md.).

Plasmid Vectors: An expression plasmid encoding for Green Fluorescent Protein (GFP) under the control of the CMV promoter was obtained from Clontech (Palo Alto, Calif.). The hMiRP1 and Q9E-hMiRP1 plasmids were created as follows. The full-length coding sequence of the hMiRP1 potassium channel and the missense mutation, Q9E-hMiRP1, (both kindly provided by Dr. S. Goldstein, Yale School of Medicine, USA) were subcloned into the BAMHI/SACI sites of the pIRES2-eGFP bicistronic expression vector from Stratagene (LaJolla, Calif.). This vector (FIG. 1) utilizes the immediate early promoter of the cytomegalovirus (CMV), which drives both the expression of the inserted cDNA (hMiRP1) and GFP with an additional neomycin/kanamycin resistance gene that facilitates the selection of stably transfected eukaryotic cells with G418. hMiRP1 and Q9E-hMiRP1 were epitope tagged by replacing the terminal stop codon in each with nucleotides encoding FLAG residues (DYKKDDDDK; SEQ ID NO: 2) by PCR (Clontech).

Stable Cell Lines: HEK293 and SH-SY5Y cells were transfected with the plasmid constructs described above using Lipofectamine2000® (Life Technologies) per the manufacturer's directions, and selected using G418. Stably overexpressing cell lines were isolated by FACS sorting, based on GFP expression, using a FACS Calibur flow cytometer with Cell Quest software (Becton Dickinson, Franklin Lakes, N.J.) equipped with a 488-nm argon-ion laser (15 mW).

Western Blotting: Parallel plates of confluent cultures of SH-SY5Y and HEK293 stable cell lines over-expressing hMiRP1 and Q9E-hMiRP1 were used to isolate the membrane fractions. Cells were lysed [1M Tris-HCl (pH 7.5), 1% Triton X-100, 5M NaCl, 1 mM NaF, 0.5M EDTA, 1 mM $Na_3VO_4$, 100 mM PMSF, and a protease inhibitor cocktail (Boehringer Mannheim)], centrifuged at 14,000×g for 5 min, and protein concentration was determined by the Bio-Rad Protein Assay (Bio-Rad, Hercules, Calif.) (Bradford, 1976). 30 µg of total protein per lane were separated on 10% SDS polyacrylamide minigels (Laemmli, 1970) and transferred to polyvinylidene difluoride (PVDF) membranes. Membranes were blocked in 50 mM Tris-HCl (pH 7.6), 100 mM NaCL, 0.2% Tween-20 and 5% nonfat dry milk and immunoblotted overnight with monoclonal anti-FLAG antibody (1:250 dilution; Sigma, St. Louis, Mo.) followed by horseradish-conjugated secondary antibody (1:10,000) for 1 hr. Signals were visualized using Renaissance chemiluminescence reagent (DuPont NEN, Boston, Mass.). The signal in each band was quantitated as the integrated optical density of the band. Relative band densities were normalized to protein loads as determined by the band density of control β-actin in each lane. Densitometric analysis was performed with the Image Analysis System MCID/M2, Imaging Research (St. Catherine, Ontario, Canada) by integrating the stained area of the bands.

hMiRP1 RNA Isolation and detection by Reverse Transcriptase-Polymerase Chain Reaction (RT-PCR): Total RNAs from cultured cells were extracted using Trizol Reagent (Life Technologies) according to the manufacturer's instructions. cDNA was synthesized using oligo-dT priming from 5 µg total RNA using the Gibco-BRL preamplification SuperScript II reverse transcriptase system (Life Technologies Inc.). Following first strand cDNA synthesis, PCRs were performed using primer pairs for hMiRP 1gene and glyceraldehyde 3-phosphate dehydrogenase (GAPDH). The primers used for hMiRP1 detection were as follows: 5' sense oligonucleotide, ACCATGTCTACTTTATCCATT; SEQ ID NO: 3 and 3' antisense oligonucleotide, CTTATCGTCGTCATCC TTGTAATCGGGGGA-CATTTTGAACCC; SEQ ID NO: 4. These primers gave rise to a product that is 405 bp long. The human glyceraldehyde-3-phosphate dehydrogenase (GAPDH) was amplified as an internal control, from 2 µl of the same cDNA, under the above conditions, and using the following primers (the nucleotide residue number and accession numbers are in parentheses): GAPDH-S, 5'-GGA CAT TGT TGC CAT CAA CGA C-3' (108-129, M17701; SEQ ID NO: 5); GAPDH-AS, 5'-ATG AGC CCT TCC ACG ATG CCA AAG-3' (525-548, M17701; SEQ ID NO: 6), which generated a 369-bp fragment. The amplified products were separated on a 2.5% agarose gel using appropriate standards and visualized with ethidium bromide staining. The bands were analyzed by BioRad Quant One software (Biorad). Signals from the hMiRP1 cDNA were normalized using the values of the corresponding products from the GAPDH amplification.

Quantitative RT-PCR: Real-time, one-step, non-nested PCR for hMiRP1 and Q9E-hMiRP1 mRNA was performed using the Light Cycler thermal cycler (Roche Diagnostics, Indianapolis, Calif.) according to the manufacturer's instructions. Total RNA was isolated and reverse transcribed to cDNA from the SH-SY5Y and HEK293 cell lines as described in the previous sections. The primer utilized to detect FLAG epitope tagged hMiRP1 was: (sense) TTATC-CAATTTCACACAGAAC (SEQ ID NO: 7) and (anti-sense) CAAAAGACGGCAATATGGT; (SEQ ID NO: 8), and to detect FLAG epitope tagged Q9E-hMiRP1: (sense) TTATC-CAATTTCACAGAGAAC (SEQ ID NO: 9) and (anti-sense) CAAAAGACGGCAATATGGT (SEQ ID NO: 8). To detect endogenous hMiRP 1 and Q9E the same forward primers were used, and the reverse primer was ACACCG-GCCTTATTC (SEQ ID NO: 10). The primers for the housekeeping gene GAPDH were as follows: (sense) ACC ACA GTC CAT GCC ATC AC (SEQ ID NO: 11) and antisense TCC ACC ACC CTG TTG CTG TA (SEQ ID NO: 12). Negative (water) and positive controls (plasmid constructs containing wildtype hMiRP1 gene) were run concomitantly to confirm integrity of the samples. To confirm amplification specificity, the PCR products were subjected to a melting curve analysis. The standard curve was generated for SH-SY5Y and for HEK293 cells by using endogenous hMiRP1 cDNA and plasmid devoid of gene.

Electrophysiology Methods: HEK293 cells that stably express HERG, but not hMiRP1 (Zhou, et al., 1999) were also stably co-transfected with either hMiRP1 or Q9E-hMiRP1 and subsequently were analyzed for channel function by single cell patch clamping using voltage clamp conditions. The data were analyzed at a sampling rate of 4 kHz and filtered at 1 kHz using Pclamp software version 6.0 (Axon Instruments, Foster City, Calif.). Leak correction was not performed, and therefore unaltered data are shown. All experiments were performed at 25° C. Protocols for steady-state activation and isochronal peak currents, and clarithromycin incubations were performed as described by Abbott et al., 1999. Initial studies were performed in buffer containing 95 mM KCl, 5 mM NaCl, 1 mM $MgCl_2$, 0.3 mM $CaCl_2$, and 10 mM HEPES (pH 7.6). For whole cell recordings, pipettes contained 100 mM KCl, 1 mM $MgCl_2$, 10 mM HEPES, and 2 mM EGTA (pH 7.5). A 50 mM Clarithromycin (American Bioanalytical, Natick, Mass.) stock in DMSO was diluted in bath solution.

Immunocytochemistry in vitro: For immunostaining, stably transfected cell lines were plated on coverslips overnight. Cells were washed several times in 0.1M PBS, fixed with 4% paraformaldehyde and permeabilized with 0.1% Triton X-100. After blocking for 3 hours (5% BSA and 10% normal goat serum in PBS), cells were incubated overnight at 4° C. with anti-FLAG antibody (Sigma) in antibody diluent (0.5% Tween-20 and 1% BSA in PBS) at concentrations appropriate for each cell line: SH-SY5Y (1:500) and HEK293 (1:300). Cells were subsequently washed several times, and incubated with the rhodamine-labeled secondary antibody at 1:600.

DNA, Cationic Lipid, Anti-DNA Antibody Heteroplexes (DAC) Formulation: An optimized formulation consisting of 10 µg of GFP plasmid DNA ("D") was mixed with 10 µg of mouse monoclonal anti-bovine DNA IgM (U.S. Biological, Swampscott, Mass.) ("A") in a total volume of 50 µl PBS, followed by incubation at 37° C. for 1 hour. 5 µl of cationic lipid ("C"), composed of a 1:1 (w/w) formulation of N-[1-(2,3-dioleyloxy)propyl]-n,n,n-triethylammonium chloride (DOTMA, Sigma Chemical Co., St. Louis, Mo.) and dioleoyl phosphatidylethanolamine (DOPE, Sigma) was added to DA with vortexing to form DAC. The heteroplex (DAC) was incubated at room temperature for 35 minutes or more before use. Control formulations using nonspecific antibody (mouse IgM, Zymed laboratories, San Francisco, Calif.), or lacking antibody (lipoplex, DC), were formulated in parallel. In order to carry out studies of DNA uptake and cellular processing of DNA antibody heterolpexes, fluorescent components were included as described in individual experiments. Rhodamine- or FITC-labeled DNA were prepared according to manufacturer's instructions using Mirus Label IT® nucleic acid labeling kits (Mirus-PanVera, Madison, Wis.), for use in tracking the uptake and processing of DNA in fluorescent microscopy and flow cytometry studies. Alexa Fluor 568 (red fluorescence) labeled anti-DNA IgM was prepared using succinimidyl ester-amine binding methodology (Alexa Fluor 568, Molecular Probes, Eugene, Oreg.), in order to investigate processing of DNA-antibody complexes. A rhodamine-labeled non-specific antibody (mouse IgM, Vector Laboratorie, Burlingame, Calif.) was employed as an additional control. BODIPY (4,4-difluoro-3a,4a-diaza-s-indacene)-labeled DOPE (Molecular Probes) was combined at a 0.5% level with the cationic lipid formulation (DOPE/DOTMA) for tracking lipid distribution.

DAC Particle Characterization: For assessing particle size and Zeta potential, aliquots of DAC or DC were assayed using a Brookhaven 90Plus Particle Sizer with a ZetaPlus Zeta Potential Analyzer (Brookhaven Instruments Corp, Brookhaven, N.Y.). The concentration of DNA entrapped in DAC or DC was determined spectrophotometrically after phenol/chloroform extraction of particles separable from suspension by 0.2 µm membrane filtration (Nalgene Co., Rochester, N.Y.).

DAC in vitro Transfection: In vitro transfection experiments were set up using A10 cells in either plastic 6 well tissue culture dishes, for initial characterization of transfection, or, to avoid auto-fluorescence in photographic or confocal data collection, in 4 chamber glass slides (Falcon, Franklin Lakes, N.J.). Cells were plated 18 hours prior to the introduction of DNA complexes. The cells were incubated at 37° C. in M199 medium, supplemented with 5% (v/v) FBS and P/S. One hour prior to introduction of DNA complex, the cells were rinsed once with PBS then P/S-free M199 medium, and the incubation was continued for 1 hour in this formulation. After 5 hours of transfection, 5% FBS was added to the cultures, and media replaced to contain 2% FBS the next day.

Uptake and intensity of fluorescein-labeled DNA in vitro was quantified by flow cytometry of cells after 48 hours of transfection, using an Epics Elite flow cytometer (Coulter Corporation, Hialeah, Fla.), observing 10,000 cells per run of each sample, and subtracting background fluorescence of untreated control cells. For determination of transfection efficiency, complexes were formulated using the GFP plasmid, and the cells were fixed with 4% paraformaldehyde after various timepoints of transfection, and 4',6 diamidino-2-phenylindole (DAPI, Vector Laboratories) mounted for nuclear staining. GFP transfection was observed using a Nikon Eclipse TE300 inverted fluorescent microscope (NIKON Inc, Melville, N.Y.; equipped with DAPI, Texas red and FITC filters) and at least three random 100× fields per culture were recorded as photographic tiff files for quantification. The number of GFP-expressing cells in each resulting file was determined by visual count, and the total number of cells in the same file counted for the nuclear DAPI image using the Nucleicount macro of NIH image v. 1.62. The results were expressed as "percent of cells transfected". In some experiments, extent and intensity of GFP expression was also quantified in cells 72 hours after transfection by flow cytometry. Fluorescent confocal microscopy of transfected cells was performed with a Nikon Eclipse E600 microscope (Nikon, Tokyo, Japan) equipped with a BioRad confocal imaging system 1024ES. Laser excitation was at 488/568 nm, using a 522DF35 filter for FITC and a 605DF32 filter for rhodamine/Alexa Fluor 568 visualization.

Animals: All studies involving the use of animals were approved by the Institutional Animal Care and Use Committee (IACUC) of The Children's Hospital of Philadelphia. Adult normal male Yorkshire swine (Willow Glen Farms, Strousburg, Pa.) of weights 25-35 kg were used for these studies. A right thoracotomy procedure under general anesthesia was used as previously published (Levy et al., 2001). Right atrial myocardial sites injected with plasmid preparations were retrieved after one week following euthanasia with a barbiturate overdose (Levy et al., 2001).

In Vivo Vector Injections: DAC heteroplexes were investigated in pig atrial myocardial injection studies using either GFP, hMiRP1, or Q9E-hMiRP1 plasmids. The DAC delivery system was first characterized in vivo. Following a right thoracotomy under general anesthesia, four separate right atrial epicardial injection sites in each pig received 100 μg of DNA, as either DAC, DC, DNA plus antibody (without cationic lipid), or DNA alone. Six pigs were studied using the reporter gene (GFP only, as above), and the atrial injection sites were retrieved after one week. Frozen sections were analyzed for the presence of GFP with fluorescence microscopy after DAPI mounting. GFP-expressing fields from treatment sites in each of the animals were recorded as digital images using both FITC and DAPI filters. Morphometrics were analyzed with NIH Image software as above (Klugherz, et al., 2000). The results were expressed as percent cells transfected. Sections were also routinely examined with hematoxylin staining. Q9E-hMiRP1 and hMiRP1 plasmids were formulated only as DAC, and were injected as above into the right atrial myocardium of 3 pigs, with sample retrieval one week postoperation as both frozen and formalin-fixed specimens. Confirmatory GFP immunohistochemistry was performed on paraffin-emedded sections using primary antibody from Molecular Probes, developed with VIP Purple chromogen (Vector Labs), and counterstained with Methyl Green (Vector Labs).

In vivo FLAG immunofluorescence: Frozen sections from pig myocardium from the Q9E/hMiRP1 studies were subjected to post-fixation by submerging the samples in cold acetone for 30 seconds. The samples were subsequently washed and non-specific binding was blocked by incubating 1 hour in 10% FBS. The sections were incubated overnight with primary anti-FLAG antibody at a concentration of 1:200. The tissues were incubated with rhodamine-labeled secondary antibody (see above) and DAPI mounted for confocal microscopy.

Statistical analyses: Data are expressed as mean±standard deviation (SD). Statistical significance was assessed using one-way analysis of variance (ANOVA) or one-sided Student's t test. P values less than 0.05 were considered significant. The significance of the differences ($P \leq 0.05$) between the groups tested by analysis of variance was assessed by the least-square differences test, using SPSS software (SPSS Inc., Chicago, Ill.).

RESULTS

Over-Expression of hMiRP1 and Q9E-hMiRP1

By RT-PCR methodology and agarose gel electrophoresis (FIG. 11A), we were able to confirm that the SH-SY5Y cell lines were stably expressing either hMiRP1 or Q9E-hMiRP1. HEK293 cells, which do not produce endogenous hMiRP1, demonstrated over-expression of either hMiRP1 or Q9E-hMiRP1 following respective transfections. In order to further document and quantify the amounts of wildtype or Q9E-hMiRP1 mRNA that was being produced per cell, quantitative RT-PCR was employed with primers including the FLAG epitope (see Methods). Total RNA extracted from $10^7$ cells of transfected and control HEK293 and SH-SY5Y cells was reverse transcribed to cDNA. cDNA quality was optimal for all samples, providing crossing points in less than 23 cycles; thereby indicating a relatively high concentration and good amplification of the DNA. With 40 cycles of a single round of quantitative PCR, SH-SY5Y-hMiRP1 and SH-SY5Y-Q9E-hMiRP1 yielded 0.01±0.0015 and 0.02±0.0017 picograms per cell of mRNA, respectively (FIG. 11B, lower panel). Moreover, our studies also demonstrated that in the HEK293 cell lines, hMiRP1 and Q9E-hMiRP1 were over-expressed, yielding 0.05±0.019 and 0.10±0.011 picograms per cell of mRNA, respectively (FIG. 11B, upper panel).

Western Blot Analyses of hMiRP1 and Q9E-transfected Cells

Figure 12:
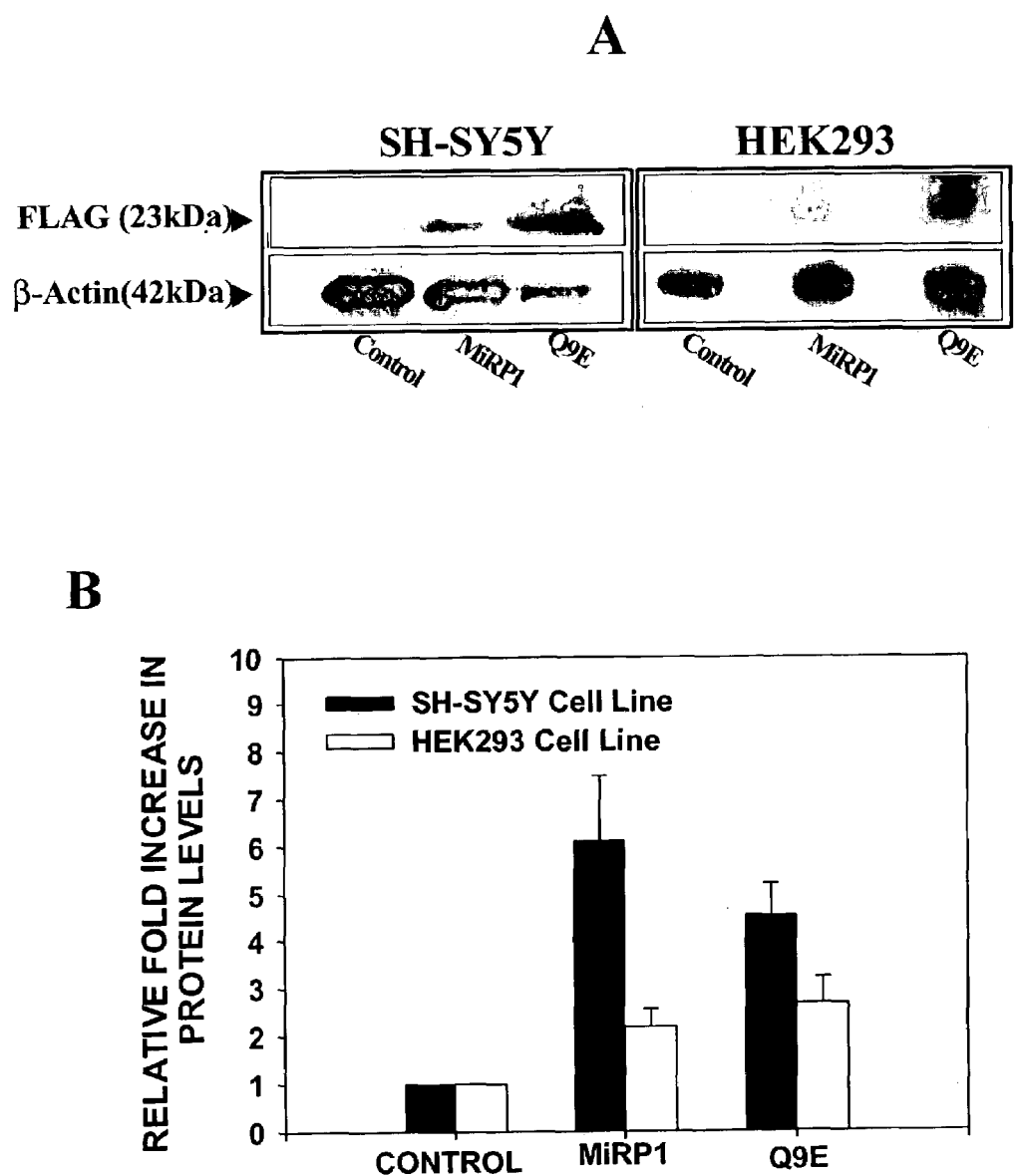
FIG. 12: Western blot analyses of wild type hMiRP1 and Q9E-hMiRP1, each with a C-terminus FLAG epitope in transfected (A) HEK293 cells and SH-SY5Y cells. The arrows indicate the 23kDa FLAG tag and the 43kDa β-actin loading control. (B) Densitometric analysis of western blots documented hMiRP1 and Q9E-h-MiRP1 in HEK293 and SH-SY5Y cells. All data were normalized to β-actin loading control. Results are expressed as the ratio hMiRP1/β-actin for each cell type (AU: arbitrary units). Levels of hMiRP1- and Q9E-hMiRP1 FLAG-tagged protein were significantly elevated compared to control in all cases ($p<0.05$).
Figure 13:
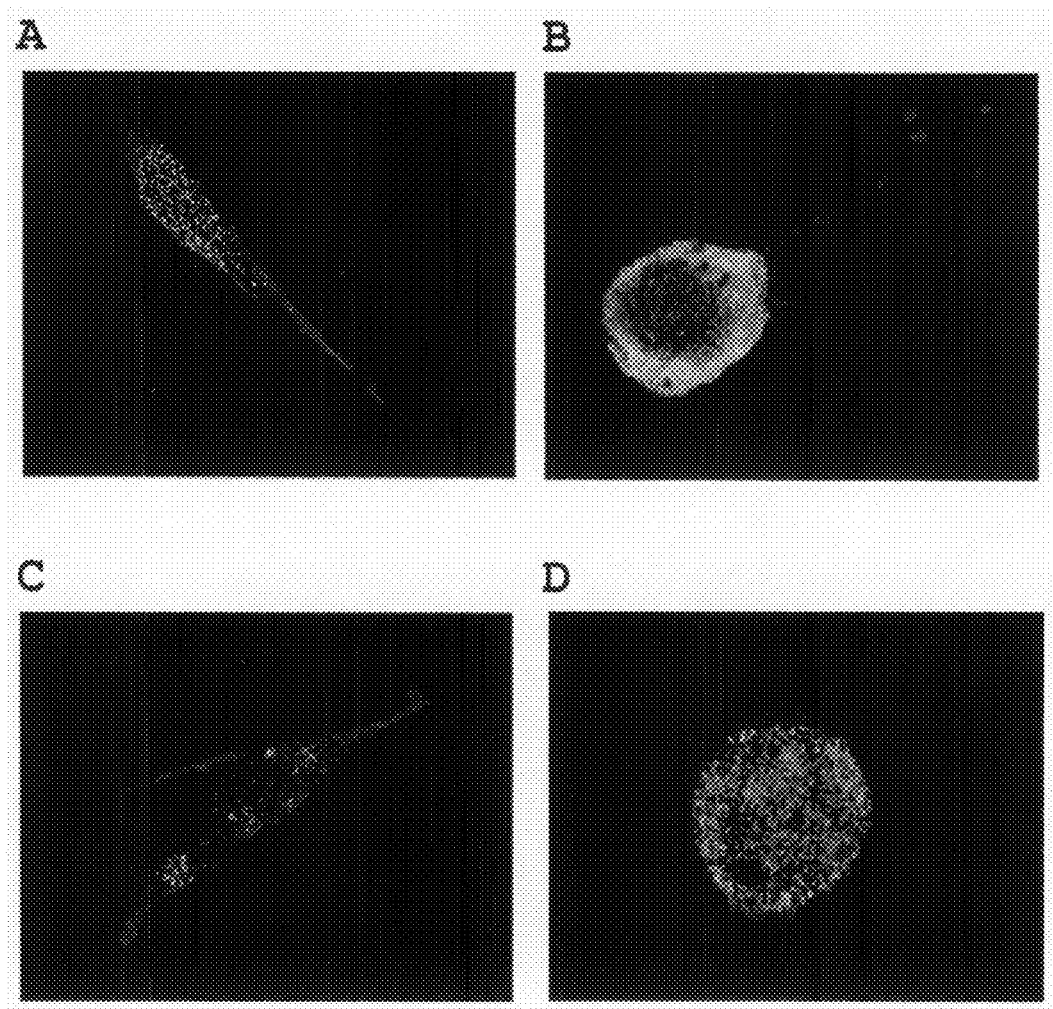
FIG. 13: SH-SY5Y and HEK293 cells stably expressing green fluorescent protein (GFP) and FLAG-tagged hMiRP1 or Q9E-hMiRP1. Confocal fluorescent microscopy demonstrates GFP expressing cells with green cytoplasm (green=FITC) with anti-FLAG localization of wild type hMiRP1 in the cell membrane using rhodamine-labeled anti-FLAG antibody for both cell types (A) SH-SY5Y and (B) HEK293, indicating ion channel localization to the cell membrane. Moreover, in Q9E-hMiRP1 over-expressing cells (C) SH-SY5Y and (D) HEK293 cells anti-FLAG (rhodamine) immunocytofluoresence demonstrates cell membrane localization comparable to A & B. (original magnification 400×).

Western blot analyses based on FLAG immuno-detection of over-expressed hMiRP1 and Q9E-hMiRP1 proteins in stably transfected HEK293 and SH-SY5Y cells are shown in FIGS. 12A and 12B. Antibodies directed against the FLAG epitope at the carboxy terminus of each gene were used to probe for hMiRP1 and Q9E-hMiRP1 mutant proteins. The anti-FLAG antibody recognizes a single band including the FLAG peptide with an apparent molecular mass of 23 kDa, indicating the presence of either hMiRP1 or Q9E-hMiRP1 protein in the stably transfected cells (FIG. 12A); these bands are absent in untransfected cell extracts. The blots were also probed with a β-actin (42 kDa) antibody as a loading control. In the four stable cell lines, densitometry confirmed the significant (p<0.05) overexpression of transgene versus controls (FIG. 12B).

Figure 10:
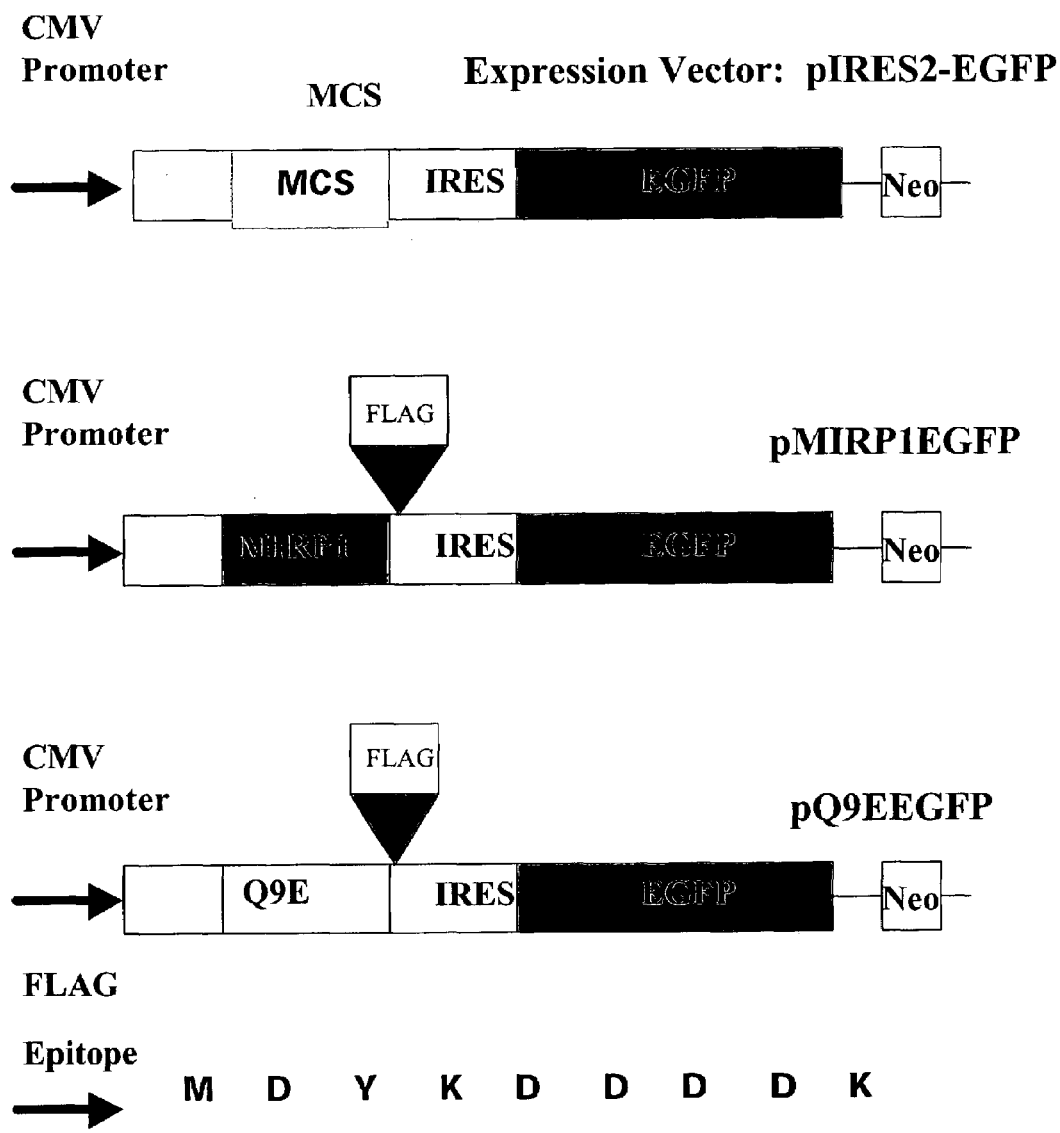
FIG. 10: Schematic diagram of pIRES2-EGFP expression vector. The pIRES2-EGFP expression vector (Clontech) possesses an internal ribosome entry site (IRES) of the encephalomyocarditis virus (ECMV) that is located between the multiple cloning site (MCS) and the enhanced green fluorescent protein (EGFP) coding region. Therefore, this enables the translation of either hMiRP1 or Q9E-hMiRP1 and EGFP. The genes of interest, either hMiRP1 or Q9E-hMiRP1, were subcloned into the multiple cloning site utilizing restriction endonucleases SACI and BAMHI. A FLAG epitope (SEQ ID NO: 1) was attached at the carboxy terminus of both hMiRP1 and Q9E-hMiRP1 to facilitate anti-FLAG immunodetection methods.

Transfection and Immunocytochemistry Studies with hMiRP1 and Q9E-hMiRP1 Plasmids: Successful Transmembrane Localization of the Expressed Transgenes Transfections with the bicistronic vectors were demonstrated by the expression pattern of GFP (see vector diagram, FIG. 10), which was found throughout the cytoplasm of the cells (FIGS. 13A-D). We studied the cellular localization of hMiRP1 protein tagged at its C terminus with a FLAG epitope in wild type and Q9E-hMiRP1 by immunostaining of transfected HEK293 and SH-SY5Y cells followed by fluorescent confocal microscopy. Mock-transfected cells from each cell line showed no detectable immunofluorescence staining (data not shown). In both SH-SY5Y and HEK293 cells transfected with wild type hMiRP1, (FIGS. 13A&13B respectively), fluorescent confocal microscopy demonstrated that rhodamine-labeled anti-FLAG fluorescence was predominantly localized to the plasma membrane, with faint cytoplasmic expression. In addition, SH-SY5Y and HEK293 cells transfected with Q9E-hMiRP1 (FIGS. 13C and 13D respectively), also display comparable anti-FLAG immunofluorescence predominantly in the plasma membrane.

Q9E-hMiRP1 and hMiRP1 Electrophysiology Studies: Proof of Concept

Figure 14:
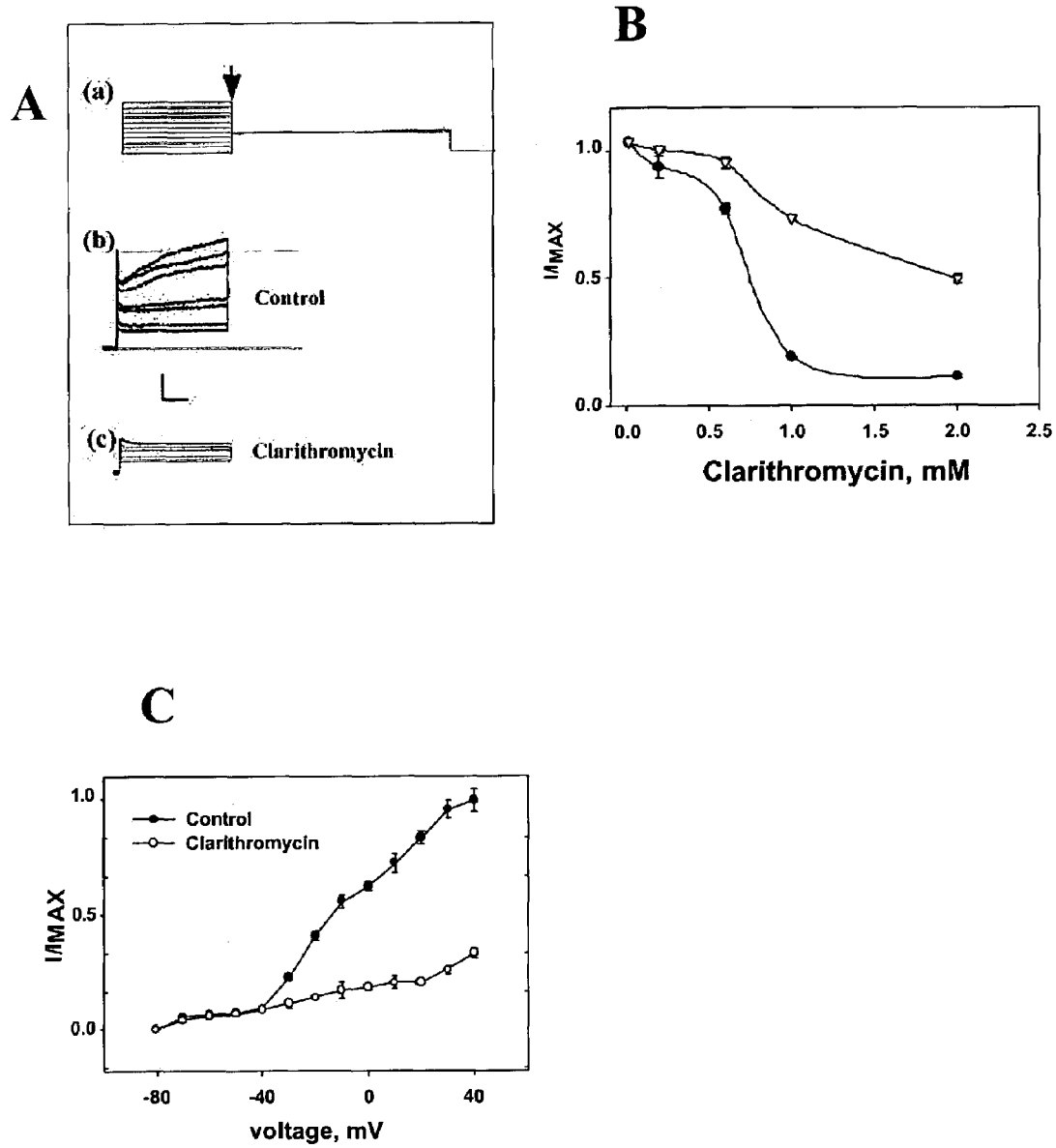
FIG. 14: Electrophysiological properties associated with stable expression of Q9E-hMiRP1 (mutant) and wild type hMiRP1 in transfected HEK293 cells. Q9E-hMiRP1 expressing cells show the hypothetically predicted increased sensitivity to blockade by clarithromycin compared to hMiRP1 overexpressing cells. (A): Raw current traces from a typical HEK293 cell overexpressing Q9E-hMiRP1; (a) Illustrates the protocol, that begins by holding at −80 mV, and sampling steady-state activation; this is followed by prepulse increases in voltage for 3 seconds (s) from −80 to 40 mV in 10 mV steps, followed by a test pulse for 6 s to −100 mV; the interpulse interval was 5 s (b) Q9E-hMiRP1 in the absence of clarithromycin produces outward potassium currents (Control); however, in the presence of clarithromycin (c) there is a substantial diminution of potassium currents. Scale bars, 50 pA (y) and 0.5 s (x), (B) Current (I)-dose relationships at equilibrium with diminished I/I max with increasing doses of clarithromycin after activation at +20 mV; filled circles: Q9E-hMiRP1 stable cells; open triangles: hMiRP1 stable cells. (C) Current-voltage (mV) relationships as determined in (A) for Q9E-hMiRP1 stable cells, mean±SEM for groups of 4 cells in the absence (filled circles) or presence (open circles) of 1.0 mM clarithromycin, which blocked increases in I/I max with increased voltages.

These experiments were conducted to confirm that plasmid transfection with our bicistronic FLAG-tagged Q9E-MiRP1 vector results in electrophysiologic effects comparable to those previously observed for this channel mutation (Abbott et al, 1999). HEK293 cells over-expressing Q9E-hMiRP1 demonstrated the hypothetically predicted reduced peak outward currents (FIG. 14A) in the presence of clarithromycin in whole cell voltage clamp studies. The clarithromyin effect was many-fold greater in the Q9E-hMiRP1 cells than that noted in cells transfected with the wild type hMiRP1 (FIG. 14B). The dose of clarithromycin causing half block of the peak outward currents for channels formed with wild-type hMiRP1 was approximately 2.0 mM (FIG. 14B). However, for Q9E-hMiRP1 overexpressing cells, the dose leading to half blockade of peak outward currents was less than 1.0 mM (FIG. 14B). Furthermore, cells over-expressing Q9E-hMiRP1 demonstrated reduced $I/I_{MAX}$ only as the prepulse potential became more positive (FIG. 14C). This is consistent with the observations of Abbott et al (1999), and is comparable to the mechanism of action of class III antiarrhythmic agents (Spector et al., 1996).

Characterization of DNA-AntiDNA Antibody-Cationic Lipid Heteroplexes (DA C): Cell Culture and in Vivo Results DAC formed stable nanospheres by a self-assembly process when formulated by first combining plasmid DNA and anti-DNA antibody, followed by vortexing with cationic lipid. Particle sizing by differential light scattering revealed DAC heteroplexes to be 370±10 nm in diameter (FIG. 15A). These DAC demonstrated a relatively stable size and charge over a one week incubation period at pH 7.4 in phosphate buffered saline at 37° C. (FIG. 15A). By comparison, DC lipoplexes also formed detectable nanoparticles, 254±37 nm in diameter, and had a more electropositive zeta potential (−8.9±5.5 vs. −15.3±4.5 mV for DAC). Extraction of DNA from DAC accounted for 28.5±1.5% of the total initial DNA in DAC formulations (FIG. 15B). However, without antibody (DC), only 13.6±0.8% (p=0.002 vs. DAC) of the same amount of DNA was retained in DC formulations with the identical amount of starting DNA (FIG. 15B).

Cell culture transfection experiments were carried out with A10 cells as a model system. Confocal microscopy studies utilizing red fluorescent labeled anti-DNA antibody in A10 cell cultures 48 hours after transfection revealed that anti-DNA antibody in DAC was in both the cytoplasm and nuclei (FIG. 15C). When DNA was omitted from the formulation, the fluorescent anti-DNA antibody combined with cationic lipid was also capable of entering nuclei (data not shown), thus indicating that nuclear entry may be facilitated by the specific anti-DNA antibody used in these studies. Furthermore, under the same conditions, rhodamine-labeled nonspecific IgM remained in the cytoplasm (data not shown). Confocal microscopy, utilizing rhodamine-labeled DNA and BODIPY-labeled cationic lipid, demonstrated that DAC were present throughout the cytoplasm and nuclei of A10 cells at 48 hours, with lipid-DNA co-localization (FIG. 15D). By comparison, DNA-cationic lipid complexes (DC) had far less DNA entry into the cytoplasm of A10 cells, and rare observations of nuclear entry by DNA (FIG. 15E). Flow cytometry studies of A10 cells exposed to either DAC or DC containing FITC-labeled DNA (FIG. 15F) demonstrated more than 4 fold greater uptake with DAC than with DC (88% vs. 21% respectively) with mean channel intensities of 38.1±1.1 vs. 1.97±0.04 (p<0.001).

DAC markedly increased the level of trans-gene expression in A10 cells (FIG. 16A), with more than a five-fold increase in transfection compared to DC complexes (FIG. 16B) as determined by cell count (FIG. 16C). Control formulations consisting of GFP DNA combined with anti-DNA antibody, or GFP DNA and lipid combined with non-specific IgM, resulted in no enhancement of transfection. Flow cytometry studies were used to confirm the magnitude of the differences between DAC and other transfection formulations (FIG. 16D). GFP expression was 6.9-fold higher in DAC-transfected A10 cell cultures compared to DC, with a 6-fold higher intensity of expression per cell, than observed with DC.

Pig myocardial injection studies were used to investigate gene transfer efficiency of DAC compared to control plasmid DNA formulations, including naked-DNA (D), DNA plus anti-DNA antibody (DA), and DNA-cationic lipid (DC). As shown in FIG. 17A, DAC resulted in a three-fold or greater increase in transfection, compared to other formulations. Fluorescent microscopy studies demonstrated the pattern of expression of GFP using DAC to be widespread, and relatively uniform (FIG. 17B), compared to the more focal and limited expression pattern seen with the various control formulations (eg. FIG. 17C). Immunohistochemistry studies using an anti-GFP antibody confirmed the extent of GFP transfection with DAC (data not shown; see FIG. 18 for GFP-immunohistochemistry).

In Vivo Expression of hMiRP1 and Q9E

Using the just described in vivo approach a series of pigs were subjected to atrial myocardial injections with DAC preparations using either the Q9E-hMiRP1 or hMiRP1 plasmids with retrieval after 7 days. Uniform and site-specific localization of GFP expression within the myocardium was observed for both vector preparations (FIGS. 18A and 18B), and was confirmed with GFP immunohistochemistry (FIGS. 18C&D), indicating that in vivo transfection with both the wild type and Q9E-hMiRP1 bicistronic plasmids was successful. Morphometry studies revealed that more than 15% of regional cardiac myocytes were transfected with either plasmid in the DAC formulations (FIG. 18F), similar to observations made with GFP-plasmid DNA incorporated into DAC (FIG. 17A). Anti-FLAG immunohistochemistry with fluorescent confocal microscopy confirmed the cell membrane localization of the Q9E-hMiRP1 transgene (FIG. 18G), as well as over-expression of the wild type (hMiRP1) construct (data not shown).

The constructs were also functional in vivo. FIG. 19 is a graph showing the changes in monophasic action potential duration following clarithromycin infusion in pigs treated with Q9E-hMirp1 and wt hMirp1.

DISCUSSION

The present studies demonstrate the use of a disease associated ion channel mutation as a therapeutic gene. The working hypothesis of these studies was that a Q9E-hMiRP1 vector could be used to mimic class III anti-arrhythmic effects, limiting these effects to a specific area of the atrial myocardium to hypothetically disrupt regional re-entrant arrhythmia pathways. This hypothesis was supported by the present results demonstrating the following necessary components: 1) Over-expression of Q9E-hMiRP1 documented by both RT-PCR and Western analyses; 2) Membrane localization of the over expressed channels; 3) Electrophysiologic responsiveness with diminished $I_{Kr}$, as predicted, in response to clarithromycin administration; these electrophysiologic effects are comparable to those of class III anti-arrhythmic agents. 4) Furthermore, we demonstrated that our bicistronic-FLAG tagged Q9E-hMiRP1 vector resulted in comparable electrophysiologic effects and clarithromycin responsiveness as observed by others over-expressing Q9E-hMiRP1 using less complex vector constructs (Abbott et al, 1999), thus indicating the potential suitability of our vector design for future in vitro and in vivo electrophysiologic studies. 5) Initial in vivo studies have also shown both Q9E expression, cell membrane localization and electrophysical functioning in pig atrial myocardium.

We also investigated the gene transfer potential of a complex multi-component formulation (heteroplex) composed of plasmid DNA, a cationic lipid moiety, and an anti-DNA antibody. Specifically, our investigations have focused on anti-DNA antibodies in a plasmid-based gene transfer vehicle, because native anti-DNA antibodies have been shown to accumulate in the nuclei of post-mitotic cells (Alarcon-Segovia et al., 1978). Therefore, we successfully demonstrated that the association of DNA with anti-DNA antibody prior to the complexation with cationic lipids could enhance transfection efficacy both in vitro and in vivo, primarily via preferential cellular and nuclear uptake of the heteroplex in comparison with the comparable (DC) lipoplex. Several mechanisms may be responsible for the preferential uptake of DAC. Zack et al., (1996) showed that DNA-antibody binding by itself might trigger anti-DNA antibody internalization either directly, or via the interaction with an unrecognized membrane determinant. This mechanism may be operative as well in the case of DAC heteroplexes. Furthermore, it has been shown that nuclear accumulation of anti-DNA antibody is a function of the amount of DNA complexed to the antibody (Avrameas et al., 2001). Thus, we have found variation in DNA delivery between production lots of antibody (data not shown), which necessitate re-optimization in each case for full implementation of the transfection amplification mediated by anti-DNA antibodies. Once formulated, however, the heteroplexes demonstrate robust physical characteristics (see FIG. 15A).

Q9E-MiRP1 transfection plus clarithromycin was the model therapeutic approach investigated in these studies, because of comparable mechanisms of action to Class III anti-arrhythmics, that also result in diminished potassium channel currents (Roden, 1998). Therefore, the $I_{Kr}$ response of transgene Q9E-hMiRP1 to clarithromycin demonstrated in the present studies could potentially be used to control regional atrial reentrant arrhythmia activity. This strategy is also attractive since the electrophysiologic effects of over-expressed Q9E-hMiRP1 can be modulated with variable dosing of clarithromycin or its analogues. Additionally, other potassium channel mutations such as the dominant negative HERG mutation, A561V (Sanguinetti et al., 1996), should also yield promising results as candidate gene therapy constructs.

We specifically chose to carry out our in vivo transfection studies using atrial myocardial injections rather than ventricular for several reasons. Since we selected a LQTS mutation as a potential therapeutic vector, we were mindful of the potential occurrence of life threatening ventricular arrhythmias as an untoward effect, that could occur due to overexpression of a LQTS gene in the ventricular myocardium (Leenhardt et al., 2000). It is far less likely that atrial overexpression of a LQTS mutation could lead to life threatening proarrhythmia activity. Similarly, class III anti-arrhythmia agents are associated with a risk of torsades des pontes or even more severe ventricular arrhythmias (Roden 1998). Thus, since Q9E-hMiRP1 with clarithromycin mimics class III effects (Abbott et al., 1999), we were also concerned that ventricular overexpression of this particular gene could present a risk of torsades des pontes, and thus this was also part of the rationale for our initial studies focusing on atrial transfection.

CONCLUSION

The present studies have demonstrated the feasibility of Q9E-hMiRP1 plasmid vectors for site specific anti-arrhythmia gene therapy studies. We have successfully produced human stable cell lines overexpressing Q9E-hMiRP1 that demonstrate membrane localization of the overexpressed mutant channel (Q9E-hMiRP1) with clarithromycin responsiveness in agreement with Abbott et al., (1999). Using an anti-DNA antibody heteroplex gene delivery system, we have also demonstrated that efficient in vivo delivery of Q9E-hMiRP1 vectors can be achieved in porcine atrial myocardium.

EXAMPLE 5

Delivery of RGT Using Mesenchymal Stem Cells

This Example describes materials and methods for providing a sustained, and permanent means of treating potentially fatal cardiac arrhythmias based on Reverse Gene Therapy (RGT) contained within a stem cell system. While the treatment of arrhythmias is exemplified herein, delivery of reverse gene therapy constructs goes far beyond arrhythmia-treatment strategies, and may be used to advantage in tissue engineering and organ regeneration approaches, as well as in localized tissue repair and site specific, but essentially permanent local gene therapy. As set forth herein, RGT is defined as the therapeutic utilization of a pathological disease, which manifests a distinctive phenotype as an effective and beneficial measure for treatment of another pathological disease. Our previous work describes the use of gene vectors for reverse gene therapy. The use of stem cells or other appropriate cells, modified with the gene program of interest to establish a permanent tissue and/or organ modification with a reverse gene therapy strategy is proposed herein. As discussed above in the previous Example, the missense mutation, Q9E-hMiRP1, which is responsible for one form of long QT syndrome (LQTS), was chosen as our candidate RGT gene. Q9E-hMirp1 is an ancillary subunit of the delayed rectifier potassium channel HERG. Upon exposure to the antibiotic, Clarithromycin (Biaxin), the channel functions abnormally in regards to a substantial diminution of inward rectifier currents and therefore functions in a similar manner to Class III anti-arrhythmia agents such as ibutilide. Our previous studies have demonstrated that ibutilide is effective in preventing re-entrant atrial flutters. As a result of the similar mechanism of action between ibutilide and Q9E-hMirp1, we propose that over-expression of Q9E-hMirp1 in a site-specific and local delivery system in the atrium of an animal model will lead to a permanent treatment for re-entrant atrial flutter. RGT measures will be executed via the local delivery system of rat mesenchymal stem cells (RMSC) in a site-specific manner.

As a local delivery system, genetically modified mesenchymal stem cells offer several advantages. In vivo studies have shown that myogenic mesenchymal stem cells that are directly injected into the myocardium leads to their differentiation into cardiomyocytes. Extensive studies demonstrating the myogenic potential of mesenchymal stem cells into cardiomyocytes have been performed in various animal models, including murine and porcine models.

Thus, rat mesenchymal stem cells that have been genetically modified to over-express the mutant form of wild type Mirp1, Q9E-hMirp1 were generated. The stable integration of the Q9E mutant gene within the genome of rat mesenchymal stem cells will provide a means for constitutive expression of the protein encoded by the construct. Injection of this stable RMSC-Q9E cell line into the right atrium of an experimental animal model will stimulate the cells to differentiate into functioning cardiomyocytes that express the mutantQ9E. Administration of clarithromycin will stress the mutant ion channel to alter the underlying pro-arrhythmic nature of the myocardium. Class III anti-arrhythmic drugs delay cardiac repolarization, and subsequently refractoriness. As a consequence of refractoriness being prolonged and conduction unaltered, reentrant arrhythmias should be highly suppressed by overexpression of Q9E in RMSC.

Although Class III anti-arrhythmic drugs and antihistamines are used to treat atrial fibrillations and allergies, respectively, they have adverse side affects that can be fatal. These medications can induce pro-arrhythmic effects in otherwise healthy individuals by their ability to cause acquired long QT syndrome. Such effects manifest as excessive delays in repolarization and polymorphic ventricular tachyarrhythmias, often presenting as torsades de pointes. $I_{KR}$ blocking class III agents cause TdP by mimicking the congenital long QT syndrome caused by mutations in the HERG gene or its functional regulatory subunit, Mirp1 that encode for $I_{KR}$. Drugs such as antiarrhythmics, antihistamines and certain antibiotics, prolong the QT interval and cause TdP by blocking cardiac K+ channels in general and selectively blocking the rapidly activating delayed rectifier channel $I_{KR}$.

In addition to being useful for therapeutic intervention, the development of stable mesenchymal stem cells that express the Q9E mutation and can differentiate into functioning cardiac myocytes, provides an excellent screening system for identifying specific drugs that may prolong the ventricular AP and influence distinctive polymorphic ventricular tachycardia, termed TdP and sudden death. Such an approach should effectively limit the frequency of this important complication by identifying those patients in which the administration of class III drugs should be avoided.

In summary, we describe the novel creation of a myogenic overexpressing Q9E cell line that can differentiate into cell lines of various origins including an array of mesodermal tissues such as bone, and cartilage, and cardiomyocytes.

Shown in FIG. 20 are confocal micrographs demonstrating co-imaging of green fluorescent protein and rhodamine immunofluorescence (anti-FLAG to localize Q9E-hMiRP1) in rat mesenchymal stem cells. The membrane localization of both Q91E-hMiRP1 and wild type MiRP1 in the cell membrane of GFP positive cells is shown by anti-FLAG rhodamine immunofluorescence. Transgenes were introduced into the RMSC using the methods set forth in Example 4.

Site-specific gene therapy with cell-based delivery of the gene program of interest could be used in virtually all of the previously described methods for reverse gene therapy. Moreover this approach is ideally suited for facilitating reverse gene therapy in a tissue engineering setting. Furthermore, auto-transplantation with reverse gene therapy provides another major new dimension, using the patients own progenitor cells as vehicles to deliver reverse gene therapy. In this approach, stem cells would be harvested from a patient of interest, cultured in vitro, modified with a reverse therapy vector, and re-injected or reimplanted into the patient in a site-specific manner. Methods for obtaining human stem cells for such purposes are known to the skilled person and have been previously described. See U.S. Pat. No. 6,387,367 and RE 37,978 which is a reissue of U.S. Pat. No. 6,015,671. I The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

References for Example 4

ABBOTT, G. W., SESTI, F., SPAWSKI, I., BUCK, M. E, LEHMANN, M. H., TIMOTHY, K. W., KEATING, M. T., GOLDSTEIN, S. A. N. (1999). hMiRP1 forms potassium channels with HERG and is associated with cardiac arrhythmia. *Cell*. 97: 175-187.

ALARCON-SEGOVIA D., RUIZ-ARGUELLES, A., FISHBEIN, E. (1978). Antibody to nuclear ribonucleoprotein penetrates live human mononuclear cells thru $F_c$ receptors. *Nature*. 5 (271): 67-69.

ANTZELEVITCH, C., SUN, Z. Q., Yan, G. X. (1996). Cellular and ionic mechanisms underlying erythromycin-induced long QT intervals and torsades de pointes. *J. Am. Coll. Cardiol*. 28: 1836-1848.

AVRAMEAS, A., TERNYNCK, T., NATO, F., BUTTIN, G., AVRAMEAS, S. (1998). Polyreactive anti-DNA monoclonal antibodies and a derived peptide as vectors for the intracytoplasmic and intranuclear translocation of macromolecules. *Proc. Natl. Acad. Sci. USA*. 95:5601-5606.

AVRAMEAS, A., TERNYNCK, T., NATO, F., BUTTIN, G., AVRAMEAS, S. (1999). Efficient gene delivery by a peptide derived from a monoclonal anti-DNA antibody. *Bioconj. Chem.* 10: 87-93.

AVRAMEAS, A., GASMI, L., BUTTIN, G. (2001). DNA and heparin alter the internalization process of anti-DNA monoclonal antibodies according to patterns typical of both the charged molecule and the antibody. *J. Autoimmun.* 11: 383-391.

CARMRLIET, E., (1992). Voltage-and time-dependent block of the delayed K+ current in cardiac myocytes by dofetilide. *J. Pharmacol. Exp. Ther.* 262: 809-817.

CRENSHAW, B. S., WARD, S. R., GRANGER, C. B., STEBBINS, A. L., TOPOL, E. J., AND CALIFF, R. M. (1997). Atrial fibrillation in the setting of acute myocardial infarction: the GUSTO-I experience. *J. of the Amer. Coll. Of Cardiol.*, 30, 406-413.

DALEAU, P., LESSARD, E., GROLEAU, M. F., TURGEON, J. (1995). Erythromycin blocks the rapid component of the delayed rectifier potassium current and lengthens repolarization of guinea pig ventricular myocytes. *Circulation.* 91: 3010-3016.

DONAHUE, K. J., HELDMAN, A. W., FRASIER, H., MCDONALD, A. D., MILLER, J. M., RADE, J. J., ESCHENHAGEN, T., MARBAN, E. (2000). Focal modification of electrical conduction in the heart by viral gene transfer. *Nature Medicine.* 6(12): 1395-1398.

DRICI, M. D., KNOLLMANN, B. C., WANG, W. X., and Woosley, R. L. (1998). Cardiac actions of erythromycin: influence of female sex. *JAMA.* 280: 1774-1776.

FLAKER, G. C., BLACKSHEAR, J. L., MCBRIDE, R., KRONMAL, R. A., HALPERIN, J. G., AND HART, R. G. (1992). Antiarrhythmic drug therapy and cardiac mortality in atrial fibrillation. *J. of the Amer. Coll. Of Cardiol.*, 20: 527-532.

FICHER, E., OBEJERO-PAZ, C. A., ZHAO, S., BROWN, A. (2002). The binding site for channel blockers that rescue misprocessed human long QT syndrome type 2 ether-a-gogo-related gene (HERG) mutations. *J. Biol. Chem.* 277(7): 4989-4998.

JURKIEWICZ, N. K., SANGUINETTI, M. C. (1993). Rate-dependent prolongation of cardiac action potentials by a methanesulfonanilide class III antiarrhythmic agent: specific block of rapidly activating delayed rectifier K+ current by dofetilide. *Circ. Res.* 72: 75-83.

KANNEL, W., CUPPLES, A., D'AGOSTINO, R. (1987). Sudden death risk in overt coronary heart disease: the Framingham Study. *Am. Heart J.* 113: 799.

KANNEL, W. B., WOLF, P. A., BENHAMIN, E. J., and LEVY, D. (1998). Prevalence, incidence, prognosis, and predisposing conditions for atrial fibrillation-population-based estimates. *Am. J. of Cardiol.*, 82 (suppl. 8A), N2-N8.

KLUGHERZ, B. D., JONES, P. L., CUI, X., CHEN, W., MENEVEAU, N. F., DEFLICE, S., CONNOLLY, J., WILENSKY, R. L., LEVY, R. J. (2000). Gene delivery from a DNA controlled-release stent in porcine coronary arteries. *Nat Biotechnol* 18(11):1181-1184.

KRAFTE, D. S., VOLBERG, W. A. (1994). Voltage-dependence of cardiac delayed rectifier block by methanesulfonamide class III anti-arrythmic agents. *J. Cardiovasc. Pharmacol.* 349: 602-610.

KREMERS, M. S. (1988). The premise, promise, and perils of the prevention of lethal ventricular tachyarrhythmias. *Am J. Med. Sci.* 296 (3): 202-220.

LEE, K. L., JIM, M. H., TANG, S. C., and TAI, Y. T., (1998). QT prolongation and torsades de pointes associated with clarithromycin. *Am. J. Med.* 10: 395-396.

LEENHARDT, A., DENJOY, I., MAISON-BLANCHE, P., GUICHENEY, P., COUMEL, P. (2000). Present concepts of congenital long QT syndrome. *Arch Mal Coeur Vaiss.* 93: 17-21.

LEES-MILLER, J. P., DUAN, Y., TENG, G. Q., THORSTAD, K., AND DUFF, H. J. (2000). Novel gain-of-function mechanism in K+ channel-related long-QT syndrome: altered gating and selectivity in the HERG N629D mutant. *Circ. Res.* 86: 507-513.

LEVY, R. J., SONG, C., TALLAPRAGADA, DEFELICE, S., HINSON, J. T., VYAVAHARE, N., CONNOLLY, J., RYAN, K., LI, Q. (2001). Tethered adenovirus gene delivery using matrices with immobilized antiviral IgG. *Gene Ther.* 8: 659-667.

MARBAN, E. (2002). Cardiac channelopathies. *Nature.* 415: 213-218.

MOUNSEY, P. J., BCH, B. M., DIMARCO, J. P., (2000). Dofetilide. *Circulation.* 102: 2665-2670.

NATTEL, S., "Class III Drugs: Amidarone, Bretylium, Ibutilide, and Sotalol." In: Zipes, D. P., Jalife, J. (Eds.), *Cardiac Electrophysiology: From Cell to Bedside.* Philadelpia: W.B. Saunders Co., 2000.

RATHORE, S.S., BERGER, A. K., WEINFURT, K. P., SCHULMAN, K. A., OETGEN, W. J., GERSH, B. J., AND SOLOMON, A. J. (2000). Acute myocardial infraction complicated by atrial fibrillation in the elderly. Prevalence and outcomes. *Circulation*, 101, 969-974.

REIFFEL, J. A., REITER, M. J., BLITZER, M. (1998). Antiarrhythmic drugs and devices for the management of ventricular tachyarrhythmia in ischemic heart disease. *Am. J. of Cardiol.* 82 (4A):311-401. Review.

ROCKMAN, H. A., KOCH, W. J., LEFKOWITZ, R. J. (2002). Seven-transmembrane-spanning receptors and heart function. *Nature.* 415: 206-12. Review.

RODEN, D. M. (1998). Taking the idio out of idiosyncratic-predicting torsades de pointes. *Pacing Clin. Electrophysiolol.* 21: 1029-1034.

SANGUINETTI, M. C., JURKIEWICZ, N. K., SCOTT A., SIEGEL, P. K. (1991). Isoproterenol antagonizes prolongation of refractory period by the class III antiarrhythmic agent E-4031 in guinea pig myocytes. Mechanism of action. *Circ Res.* 68(1): 77-84.

SANGUINETTI, M. C., CURRAN, M. E., SPECTOR, P. S., KEATING, M. T. (1996). Spectrum of HERG K+ channel dysfunction in an inherited cardiac arrhythmia. *Proc. Nati. Acad. Sci. U.S.A.* 93: 2208-2212.

WANG J., FENG, J., NATTEL, S. (1994). Class III antiarrhythmic drug action in experimental atrial fibrillation. Differences in reverse use dependent effectiveness between d-sotalol and the new antiarrhythmic drug ambasilide. *Circulation.* 90(4): 2032-2040.

YANASE, K., SMITH, R. M., PUCCETTI A., JARETT, L., MADAIO, M. P. (1997). Receptor-mediated cellular entry of nuclear localizing anti-DNA antibodies via myosin 1. *J. Clin. Invest.* 100(1): 25-31.

ZACK, D. J., STEMPNIAK, M., WONG, A. L., TAYLOR C., WEISBART, R. H. (1996). Mechanisms of cellular penetration and nuclear localizastion of an anti-double strand DNA autoantibody. *J. Immunol.* 157(5): 2082-2088.

ZHOU, Z., GONG, Q., JANUARY, C. T. (1999). Corrective of defective protein trafficking of a mutant HERG potassium channel in human long QT syndrome. Pharmacological and temperature effects. *J. Biol. Chem.* 1999 274(44): 31123-31126.

What is claimed is:

1. A method of alleviating reentry atrial flutter in an affected animal cell or tissue, said method comprising locally delivering to a cardiac cell or tissue a reverse gene therapy vector, said vector comprising a promoter operably linked with a nucleic acid encoding Q9E-hMirp1, wherein activity of said Q9E-hMirp1 is modulated via administration of clarithromycin, whereby delivery of said reverse gene therapy vector to the affected cardiac cell or tissue and administration of clarithromycin alleviates the reentry atrial flutter.

2. The method of claim 1, wherein said reverse gene therapy vector is selected from the group consisting of naked DNA, a plasmid, a condensed nucleic acid, and a virus vector comprising a nucleic acid.

3. The method of claim 2, wherein said condensed nucleic acid comprises a DNA molecule and a polycationic condensing agent.

4. The method of claim 3, wherein said polycationic condensing agent is selected from the group consisting of poly-L-lysine and $Ca^{2+}$ ions.

5. The method of claim 1, wherein said reverse gene therapy vector is delivered to the afflicted cell in a form selected from the group consisting of a particle comprising said vector, a microparticle comprising said particle, a nanoparticle comprising said vector, an implantable device having a surface coated with a matrix comprising said vector, and a bulk material comprising said vector.

6. The method of claim 5, wherein said implantable device comprises an electrode located in close proximity to a myocardial tissue of the animal.

7. The method of claim 6, wherein the myocardial tissue is right atrial myocardium.

8. The method of claim 1, wherein said cardiac cell is a myocardial cell.

9. The method of claim 8, wherein said myocardial cell is a right atrial myocardium cell.

* * * * *

UNITED STATES PATENT AND TRADEMARK OFFICE
CERTIFICATE OF CORRECTION

PATENT NO.        : 7,282,489 B2                                    Page 1 of 1
APPLICATION NO.   : 10/422551
DATED             : October 16, 2007
INVENTOR(S)       : Robert J. Levy and Denise Y. Burton It is certified that error appears in the above-identified patent and that said Letters Patent is hereby corrected as shown below:

On Title Page, Item (22), Date Filed
    Please delete "Jul. 31, 2003" and insert therefor --Apr. 24, 2003--.

On Title Page, Related U.S. Application Data
    Please insert: Item
        --(60)   Provisional application No. 60/374,840, filed on Apr. 24, 2002.--.

Signed and Sealed this

Ninth Day of December, 2008

JON W. DUDAS
*Director of the United States Patent and Trademark Office*

SEQUENCE LISTING

<160> NUMBER OF SEQ ID NOS: 12

<210> SEQ ID NO 1
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 1

Met Asp Tyr Lys Asp Asp Asp Asp Lys
 1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 2

Asp Tyr Lys Lys Asp Asp Asp Asp Lys
 1               5

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
accatgtcta ctttatccat t                                             21

<210> SEQ ID NO 4
<211> LENGTH: 42
<212> TYPE: DNA
<213> ORGANISM: Artificial Sequence
<220> FEATURE:
<223> OTHER INFORMATION: Primer

<400> SEQUENCE: 4
cttatcgtcg tcatccttgt aatcggggga cattttgaac cc                      42

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
ggacattgtt gccatcaacg ac                                            22

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
atgagccctt ccacgatgcc aaag                                          24

```
<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
ttatccaatt tcacacagaa c                                              21

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
caaaagacgg caatatggt                                                 19

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
ttatccaatt tcacagagaa c                                              21

<210> SEQ ID NO 10
<211> LENGTH: 15
<212> TYPE: DNA
<213> ORGANISM: Artificial Sequence
<220> FEATURE:
<223> OTHER INFORMATION: Primer

<400> SEQUENCE: 10
acaccggcct tattc                                                     15

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
accacagtcc atgccatcac                                                20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
tccaccaccc tgttgctgta                                                20
```